(12) United States Patent
Le Buanec et al.

(10) Patent No.: US 8,372,388 B2
(45) Date of Patent: *Feb. 12, 2013

(54) METHOD FOR PREPARING A STABLE TNF-α VACCINE

(75) Inventors: Hélène Le Buanec, Paris (FR); Daniel Zagury, Paris (FR)

(73) Assignee: Neovacs, Paris (FR)

( * ) Notice: Subject to any disclaimer, the term of this patent is extended or adjusted under 35 U.S.C. 154(b) by 447 days.

This patent is subject to a terminal disclaimer.

(21) Appl. No.: 11/135,660

(22) Filed: May 24, 2005

(65) Prior Publication Data

US 2006/0013800 A1    Jan. 19, 2006

Related U.S. Application Data

(63) Continuation-in-part of application No. 10/527,975, filed as application No. PCT/FR03/02733 on Sep. 16, 2003, now Pat. No. 7,972,603.

(30) Foreign Application Priority Data

Sep. 16, 2002    (FR) ...................... 02 11455

(51) Int. Cl.
A61K 39/385    (2006.01)
(52) U.S. Cl. ............. 424/85.1; 424/195.11; 424/198.1; 424/194.1; 530/351
(58) Field of Classification Search .................. None
See application file for complete search history.

(56) References Cited

U.S. PATENT DOCUMENTS

| | | | |
|---|---|---|---|
| 5,008,116 A | | 4/1991 | Cahn |
| 6,093,045 A | * | 7/2000 | Hoff ............... 439/357 |
| 6,093,405 A | | 7/2000 | Zagury et al. |
| 6,340,461 B1 | | 1/2002 | Terman |
| 6,455,045 B1 | * | 9/2002 | Zagury et al. ....... 424/184.1 |
| 6,878,370 B1 | * | 4/2005 | Zagury et al. ........ 424/85.1 |
| 7,022,482 B2 | * | 4/2006 | Zagury et al. ............ 435/6 |
| 2002/0098203 A1 | | 7/2002 | Gustavsson et al. |
| 2004/0028647 A1 | * | 2/2004 | Zagury et al. ........ 424/85.1 |

FOREIGN PATENT DOCUMENTS

| | | |
|---|---|---|
| FR | 2635532 | 2/1990 |
| WO | WO 9101146 A1 | 2/1991 |
| WO | WO 9627389 A1 | 9/1996 |
| WO | WO 9846642 A1 * | 10/1998 |
| WO | WO 9957981 A1 | 11/1999 |
| WO | WO 0003732 A1 | 1/2000 |
| WO | WO 0211759 A1 * | 2/2002 |
| WO | WO 0222164 A1 | 3/2002 |

OTHER PUBLICATIONS

Bizzini et al., Cell Mol Biol (Noisy-le-grand). May 1995;41(3):351-6, Abstract Only.*
Antigen Design and Sera Purification, Sigma Genosys, 2006.*
Stedman's Medical Dictionary, 27th Ed., 2000. Lippincott, Williams & Wilkins.*
Le Buanec et al., Biomed & Pharmacother. Feb. 2000; 54:41-4.*
Musselli et al., J Cancer Res Clin Oncol. Oct. 2001: 127(Suppl 2):R20-R26.*
Le Buanec et al., Biomed & Pharmacother. Feb. 2000; 54:41-4).*
Shirakawa et al, "VEGF121-specific monoclonal antibodies, hybridomas producing them, and determination of VEGF using the antibodies," Chemical Abstracts Service, 1999, XP00224246.
Kim et al., "Comparison of the effect of different immunological adjuvants on the antibody and T-cell response to immunization with MUCI-KLH and GD3-KLH conjugate cancer vaccines," Vaccine 18, (2000), pp. 597-603, XP002242468.

* cited by examiner

*Primary Examiner* — Cherie M Stanfield
(74) *Attorney, Agent, or Firm* — Young & Thompson

(57) ABSTRACT

A stable immunogenic product for the induction of antibodies against one or more antigenic proteins in a subject, characterized in that it comprises proteinaceous immunogenic heterocomplexes which are formed by associations between (i) antigenic protein molecules and (ii) proteinaceous carrier molecules and in that less than 40% of the antigenic proteins (i) are linked to the proteinaceous carrier molecules (ii) by a covalent bond.

20 Claims, 19 Drawing Sheets

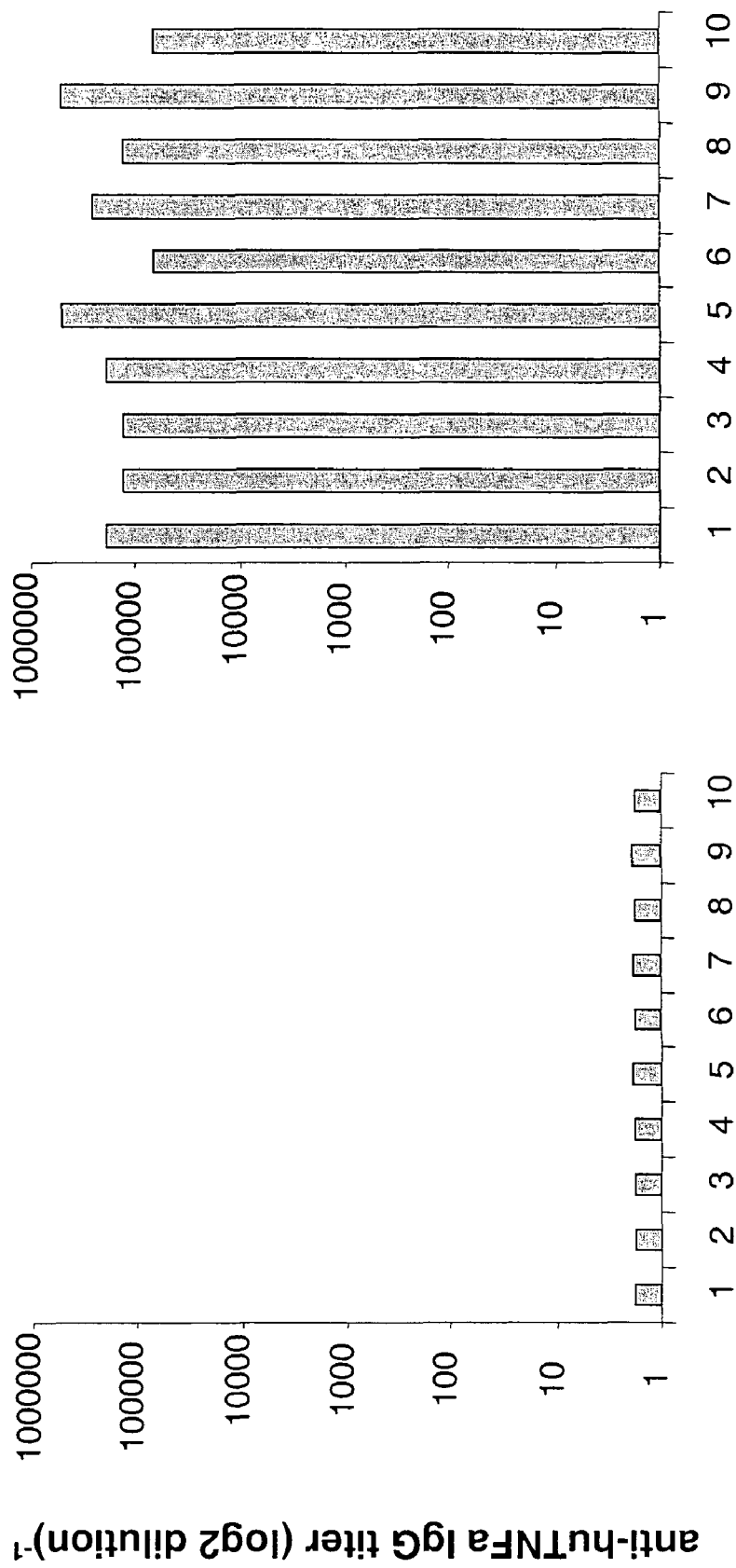

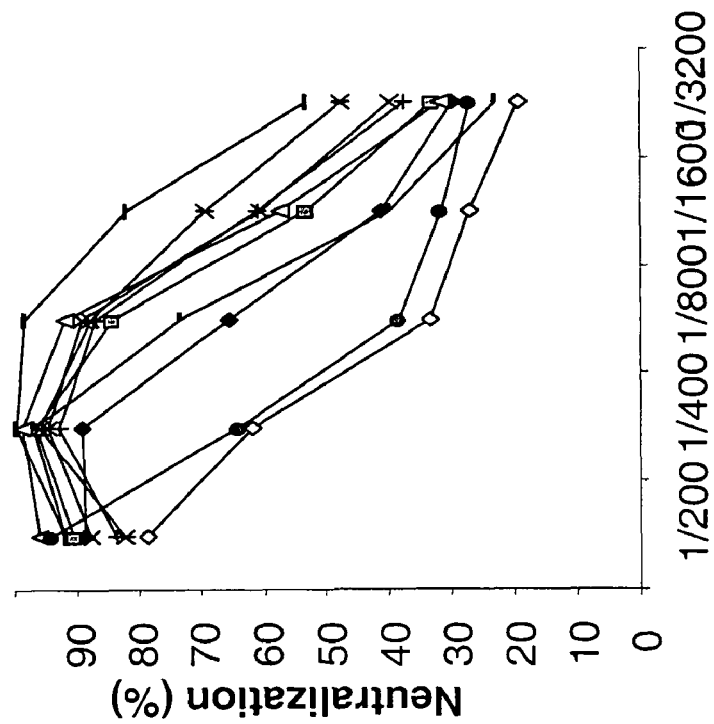
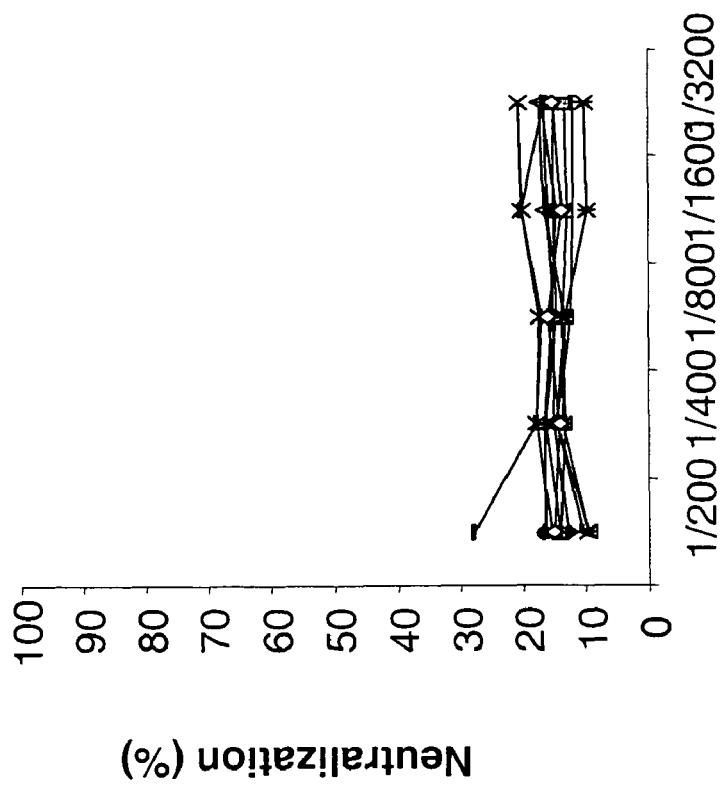
Figure 15B
Figure 15A

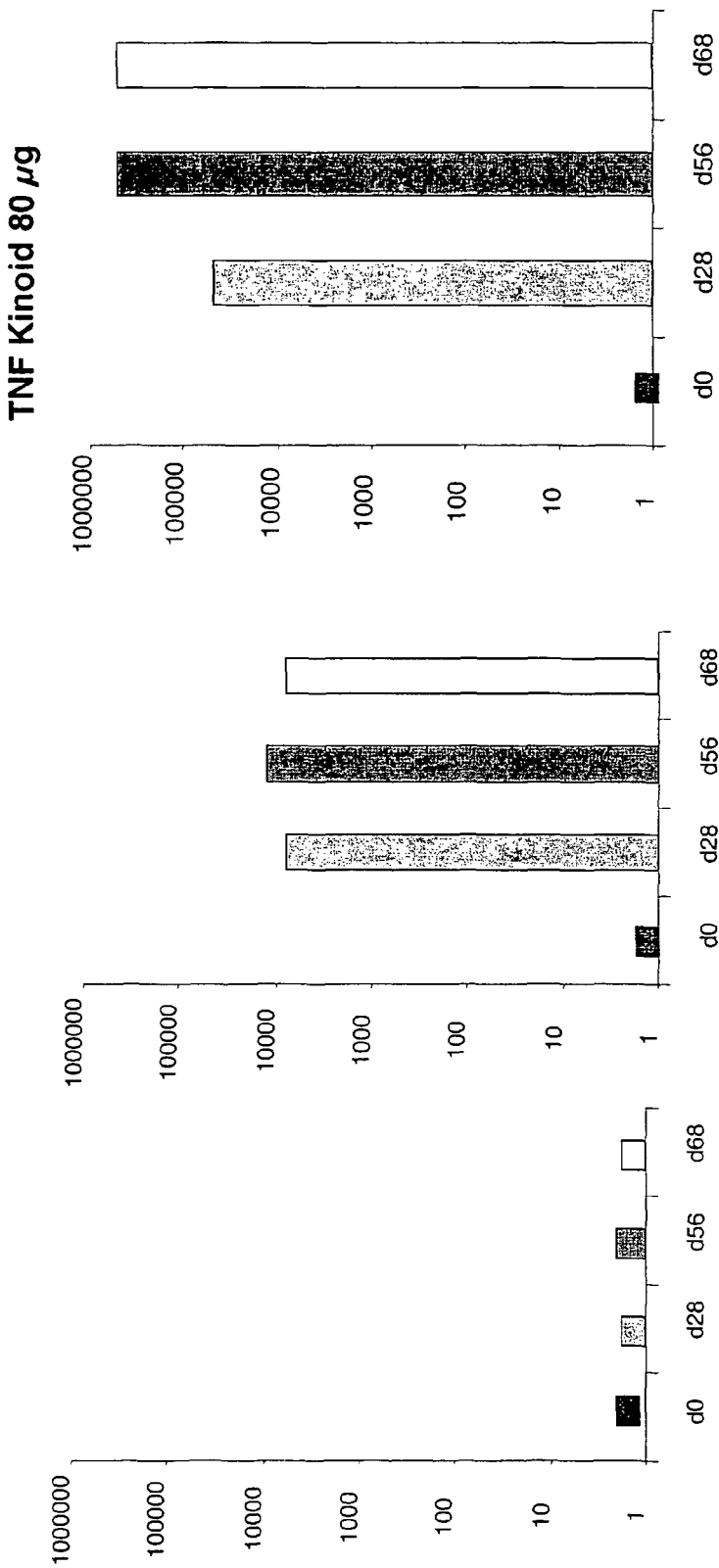

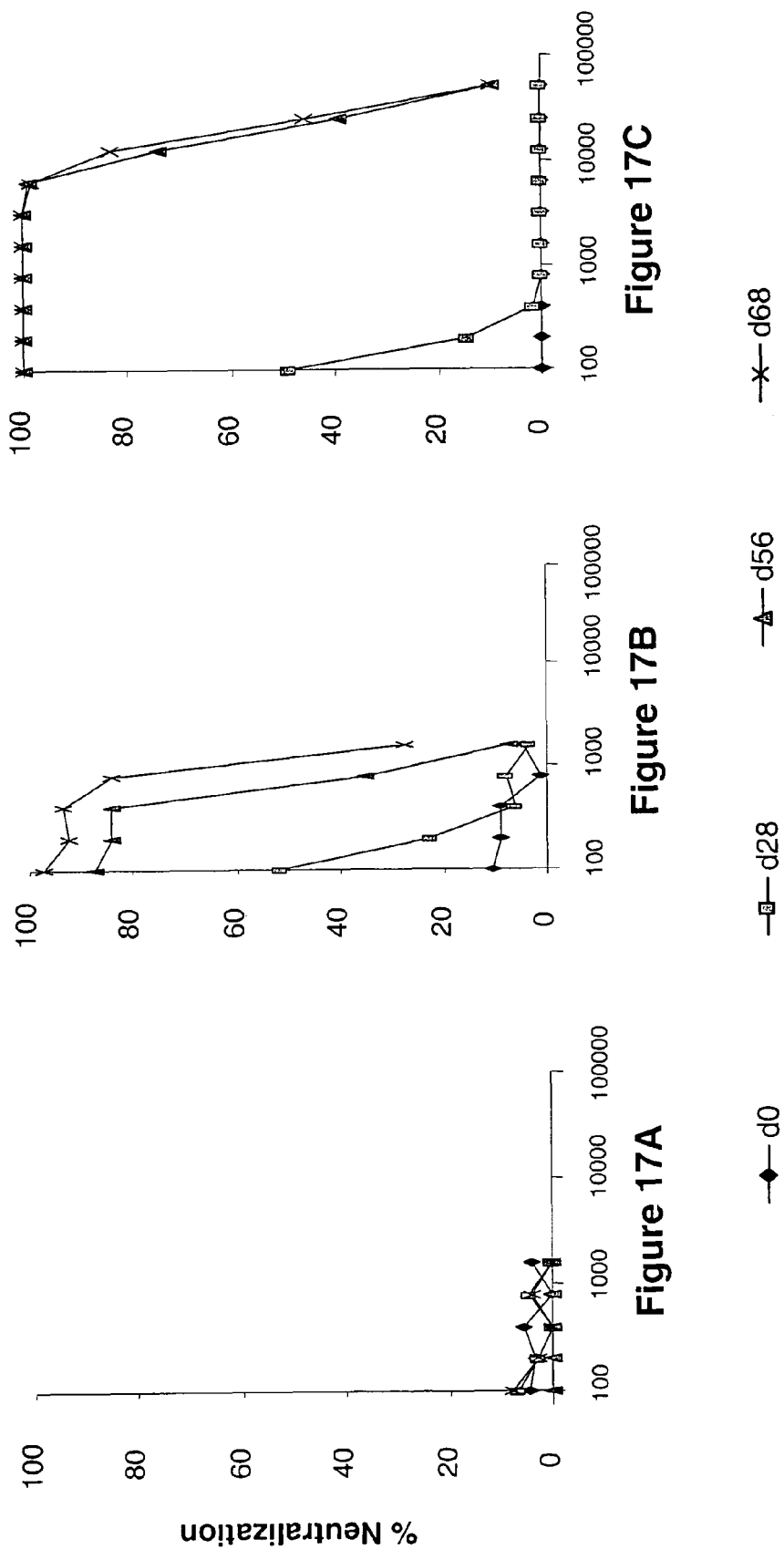

anti-huTNFa IgG titer (log2 dilution)$^{-1}$

METHOD FOR PREPARING A STABLE TNF-α VACCINE

CROSS-REFERENCE TO RELATED APPLICATIONS

The present patent application is a continuation-in-part of application Ser. No. 10/527,975, filed Mar. 15, 2005 now U.S. Pat. No. 7,972,603, which is a nationalization of International application No. PCT/FR03/002733, filed Sep. 16, 2003, and published in French, both of which are incorporated herein by reference in their entireties.

BACKGROUND OF THE INVENTION

1. Field of the Invention

The present invention relates to stable immunogenic products comprising immunogenic protein heterocomplexes for obtaining a humoral immune response with production of specific antibodies raised against one ore more antigens, in particular against a "self" antigen, as well as their use in the field of vaccines.

2. Related Art

Obtaining a high level antibody response from a given antibody, in an individual, is an object commonly sought, whether the antigen is a "foreign" antigen or a "self" antigen.

However, the problem of a good recognition of the antigen against which an antibody response is being sought, in an individual, should be solved in a number of cases, more particularly (a) when the antigen of interest behaves like a "hapten", i.e. a low molecular mass chemical structure which is little or not immunogenic under a free form, but that, once fixed on a high molecular mass molecule, is able to induce the production of specific antibodies of such a hapten, and (b) when the antigen of interest is a self protein, i.e. a protein being naturally produced in the individual, for which there exists an immune tolerance due to the deletion of corresponding lymphocyte T clones, during the development of the immune system.

In order to cause, or increase, the recognition of an antigen of interest by B cells, various immunogenic constructions were developed in the state of the art.

A first immunogenic construction form comprises a covalent coupling of the antigen of interest on a carrier molecule, the carrier molecule bringing structures recognized by the auxiliary T lymphocytes ("T helper" cells), in association with class II molecules of the Histocompatibility Major Complex (HMC), and activating the auxiliary T lymphocytes then producing various cytokins, amongst which IL-2, said cytokins activating in turn the specific B cell clones of the antigen of interest. The specific B cells of the antigen of interest, once activated, multiply and produce antibodies specific to the antigen of interest, which is the objective being sought. Generally, such a type of immunogenic constructions comprises products of the covalent chemical coupling between the antigen of interest and the carrier molecule, which, after purification and removal steps of the non coupled products, are final products with a well defined chemical structure.

The first form of an immunogenic construction is for example illustrated by the article by Richard and al. describing the preparation of products of the covalent coupling between IL-9 and ovalbumin (Proc. Natl. Acad. Sci. USA, Vol. 97(2): 767-772). It is also illustrated in such U.S. Pat. No. 6,340,461 (Terman) which discloses coupling products between one or more copies of an antigen of interest, against which a specific antibody response is being sought in an individual, and a carrier molecule consisting in a "Superantigen". The antigen of interest is coupled exclusively covalently to the carrier molecule, for example, by means of glutaraldehyde (also called "pentanedial"), the non-covalently coupled products being removed in order to obtain a chemically well-defined final product.

Optionally, the product from the covalent coupling between the antigen of interest and the superantigen could be prepared in the form of a polymer of said coupling product, for example, through a non covalent bond of the monomeric coupling products between one another, through ionic interactions, adsorption interactions as well as biospecific interactions. For example, the monomeric coupling products could form complexes with highly positively or negatively charged molecules, through salt bridges produced in low ionic strength conditions. Larges complexes of monomeric coupling products are prepared using charged polymers such as poly(L-glutamic acid) or poly(L-lysine) polymers. According to another embodiment of a monomeric coupling product polymer, the exclusively covalent coupling products between the antigen of interest and the superantigen could be adsorbed or coupled non covalently at the surface of microparticles, such as latex beads or other hydrophobic polymers.

A second embodiment of such immunogenic constructions commonly called "MAP" structure (for "Multi-Antigenic Protein") generally have the form of a protein backbone comprised of a linear or branched, poly(lysine) polymer, onto which one or more antigens of interest are covalently bound.

A third embodiment of such immunogenic constructions consists in microparticles onto which fixed the antigen(s) of interest is/are bound. Various forms of antigen carrier microparticles are known.

For example, iscomes (for "immunostimulating complexes") are known comprised of an antigenic complex and an adjuvant, the QuilA compound.

Liposomes are also known having the same drawbacks as the iscomes, i.e. more particularly some toxicity and immunological side effects, due to their lack of purity.

Biodegradable microparticles are also known such as lactic acid and glutamic acid polymers (Aguado and Lambert, 1992, Immuno. Biol., Vol. 184: 113-125) as well as starch particles (U.S. Patent Application 2002/0098203—Gutavsson et al.), in the polymeric matrix of which antigens of interest are trapped. Such particles release the antigen under their soluble form during the degradation of the polymeric matrix.

Particles have also been disclosed exclusively comprised of hybrid recombinant proteins, as disclosed in French Patent Application FR 2,635,532 (Thiollais et al.).

Porous microspheres are also known wherein the antigens are immobilized within micropores through captation or physical coupling, as disclosed in the U.S. Pat. No. 5,008,116 (Cahn).

However, the various solutions suggested in the state of the art share in common at least one technical inconvenient related to their preparation method, i.e. the loss of a high proportion of the antigenic material of interest, due to a necessary step for removing the non coupled or non adsorbed antigens.

Moreover, while the prior art techniques allow to provide an association between the low molecular mass antigen of interest with a carrier molecule, they are generally not adapted to coupling a high molecular mass antigen of interest, for example, of more than 10 kDa, with the carrier molecule, because, in particular, of steric hindrances preventing coupling a high number of molecules of antigens of interest having a high molecular mass with an identical carrier molecule.

Finally, most if not all the known peptide antigenic constructions encompass in their structure a single carrier molecule, which is a technical inconvenient when the objective is to induce a preventive or therapeutic immune response both against the antigen of interest and the carrier molecule itself.

There is therefore a need in the state of the art for improved immunogenic constructions allowing for the production of a high level of antibodies specific to an antigen of interest in an individual where such a humoral immune response is sought, being less expensive, simple to prepare and able to be synthesized reproducibly.

SUMMARY OF THE INVENTION

The present invention provides new immunogenic constructions allowing the solution of various technical problems encountered with the immunogenic constructions as known in the prior art and allowing the meeting of the above-described various technical needs.

The object of the invention is to provide a stable immunogenic product for inducing antibodies raised against one or more antigenic proteins in a subject, characterized in that it comprises protein immunogenic heterocomplexes consisting of associations between (i) antigenic protein molecules and (ii) carrier protein molecules and in that less than 40% of the antigenic proteins (i) are covalently linked to carrier protein molecules (ii).

Another object of the invention is also an immunogenic product comprising stable protein immunogenic heterocomplexes for inducing antibodies raised against one or more antigenic proteins in a subject, each heterocomplex comprising (i) a plurality of antigenic proteins, linked to a (ii) carrier protein molecule, characterized in that less than 40% of the antigenic proteins (i) are covalently linked to carrier protein molecules (ii).

Preferably, the immunogenic heterocomplex making up the immunogenic product according to the invention comprises 5 to 50 antigenic proteins (i) for one carrier protein molecule (ii), preferably 20 to 40 antigenic proteins (i) for one carrier protein molecule (ii).

Preferably, the covalent bonds between one or more antigenic proteins (i) and the carrier protein molecules (ii) occur by means of a functional binding chemical agent.

It is meant under antigenic molecule of interest, any protein comprising one or more B epitopes of a native antigenic protein against which the production of antibodies is being sought. Said antigenic molecule of interest can consist in the native protein itself or a protein derivate of the native protein, such as a peptide fragment of the native protein, as well as any biologically inactivated form of the native protein obtained through chemical, physical treatment or genetic mutation. The antigenic molecule of interest could also consist in a homo-oligomer or a homo-polymer of the native protein as well as a homo-oligomer or a homo-polymer of a peptide fragment of the native protein. The antigenic protein of interest could also consist in a hetero-oligomer or a hetero-polymer comprising a combination of several distinct peptide fragments initially included in the native protein.

According to the general embodiment of an immunogenic product according to the invention, the carrier protein molecule (ii) is an immunogenic protein inducing the production of T helper lymphocytes and/or of cytotoxic T lymphocytes raised against cells having at their surface said carrier protein molecule or any peptide being derived therefrom, in association with presenting molecules of the Major Histocompatibility Complex (MHC), respectively of class I and/or class II. The carrier protein molecule (ii) could also be an immunogenic protein inducing both the production of T helper lymphocytes and the production of antibodies by B lymphocytes raised against the carrier protein.

According to an embodiment of a particular interest, the immunogenic product is characterized in that the carrier protein molecule (ii) is an immunogenic protein inducing the production of T cytotoxic lymphocytes raised against cells having at their surface said carrier protein molecule or any peptide being derived therefrom, in association with molecules of the Major Histocompatibility Complex (MHC) class I.

The preferred immunogenic products according to the invention are selected amongst immunogenic products comprising the following heterocomplexes, wherein the antigenic proteins (i), on the one hand, and the protein carrier molecule (ii), on the other hand, are respectively:

a) (i) IL-4 and (ii) KLH;
b) (i) alpha interferon and (ii) KLH;
c) (i) VEGF and (ii) KLH;
d) (i) IL-10 and (ii) KLH;
e) (i) alpha interferon and (ii) gp 160 of VIH1
f) (i) IL-4 and (ii) the Bet v 1 allergenic antigen; and
g) (i) VEGF and (ii) the papillomavirus E7 protein;
h) (i) the inactivated VIH1 Tat protein and (ii) the VIH1 gp120 protein.
i) (i) an IgE isotype human antibody and (ii) the inactivated VIH1 Tat protein;
j) (i) the ricin β fragment and (ii) KLH.

The invention also relates to a composition, more particularly, a pharmaceutical composition, an immunogenic composition or a vaccine composition, characterized in that it comprises an immunogenic product such as hereinabove described.

It also relates to a method for preparing an immunogenic product according to any one of claims 1 to 16, characterized in that it comprises the following steps of:

a) incubating the antigenic proteins (i) and the carrier molecule (ii) in a molar ratio (i):(ii) ranging from 10:1 to 50:1 in the presence of a binding chemical; and b) collecting the immunogenic product comprising immunogenic heterocomplexes being prepared in step a).

Other objects, features, and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 5A relates to mice immunized with murine VEGF. FIG. 5B relates to mice immunized with the immunogenic product comprising KLK-VEGF heterocomplexes. FIG. 5C illustrates control mice injected with Freund's Incomplete Adjuvant (FIA).

FIGS. 14A and 14B illustrate the humoral response in mice immunized respectively with (A) KLH alone or (B) a stable immunogenic product manufactured as disclosed in Example 35. Abscissa: individuals; Ordinate: IgG anti-TNFa antibody titers.

FIGS. 15A and B illustrate the anti-TNFa neutralizing activity of the serum antibodies produced by mice immunized respectively by (A) KLH alone or (B) a stable immunogenic product manufactured as disclosed in Example 35. Each curve corresponds to the blood serum form one mouse. Abscissa: percent neutralization of the TNFa activity; Ordinate: serum dilution.

FIGS. 16A, 16B, and 16C illustrate the humoral response of Rhesus macaques immunized respectively with (A) KLH alone, (B) 20 μg of) a stable immunogenic product manufactured as disclosed in Example 35, and (C) 80 μg of a stable immunogenic product manufactured as disclosed in Example 35. Abscissa: Days after first injection; Ordinate: IgG anti-TNFa antibody titers.

FIGS. 17A, 17B, and 17C illustrates the anti-TNFa neutralizing activity of the serum antibodies produced by Rhesus macaques immunized respectively with (A) KLH alone, (B) 20 μg of a stable immunogenic product manufactured as disclosed in Example 35, and (C) 80 μg of a stable immunogenic product manufactured as disclosed in Example 35. Abscissa: percent neutralization of the TNFa activity; Ordinate: serum dilution.

DETAILED DESCRIPTION OF THE PREFERRED EMBODIMENTS

Figure 1:
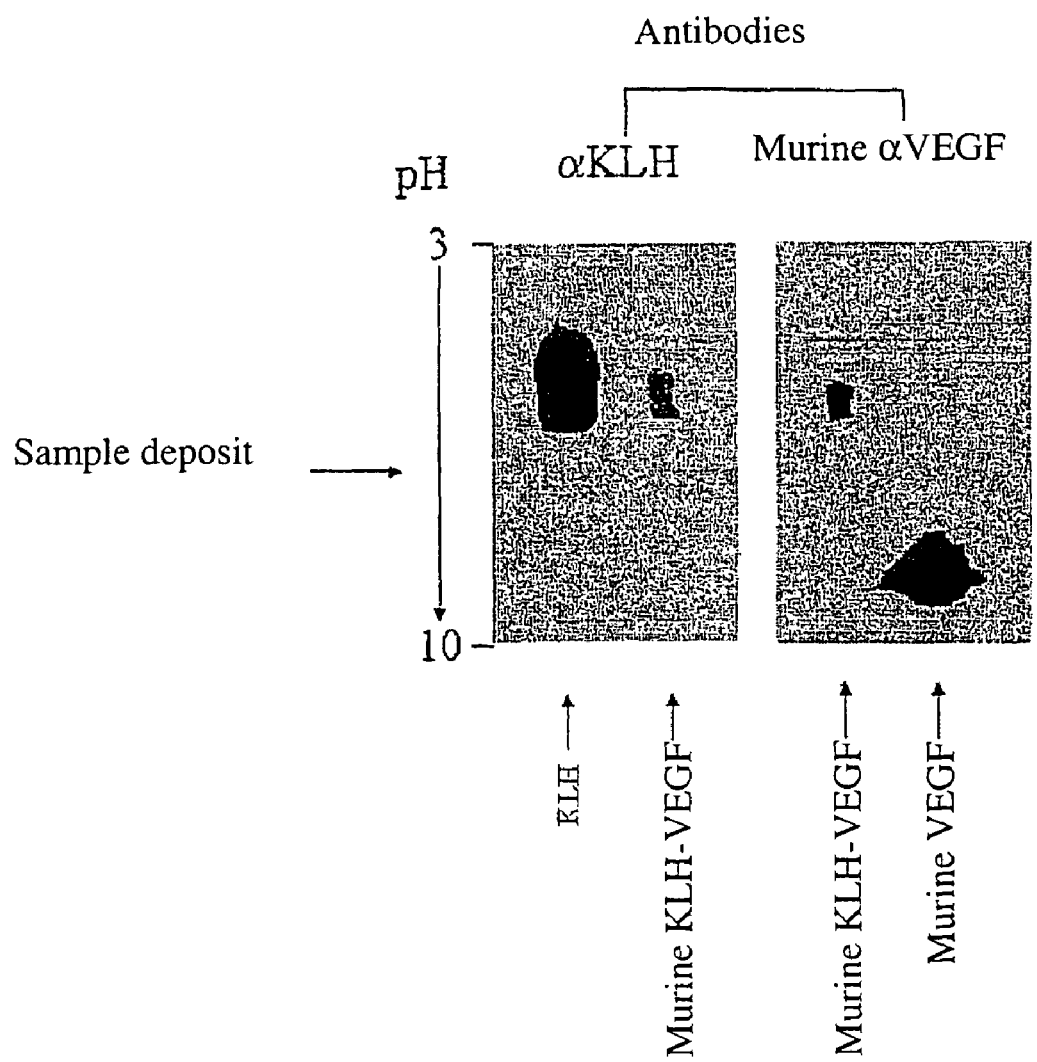
FIG. 1 illustrates the characterization of the immunogenic product comprising murine KLH-VEGF heterocomplexes through isoelectrofocusing in an agarose gel followed by the emergence of proteins through immuno-blotting ("Western Blot").

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The invention provides new immunogenic constructions inducing a high level of production of antibodies specific to an antigen of interest, in an individual.

The Immunogenic Protein Heterocomplexes According to the Invention

It has been shown according to the invention that the production of a high level of antibodies specific to an antigen of interest could be obtained, in an individual, through the immunization of such an individual with an immunogenic product where said antigen of interest is associated with a carrier protein molecule, the association between said antigen of interest and said carrier protein being partially covalent and partially non covalent.

More specifically, it has been shown according to the invention that an excellent antibody response raised against an antigen of interest is obtained when an individual is being immunized with a stable immunogenic product comprising protein heterocomplexes, wherein the heterocomplexes comprise stable associations between antigen of interest and said carrier protein molecule and wherein only a low proportion of such associations is due to a covalent bond between the antigen of interest and the carrier protein molecule, the other associations between the antigen of interest and the carrier protein molecule being produced by weak bonds, ionic interactions, hydrogen bonds, Van der Waals forces, etc.

In particular, it has been shown according to the invention that an optimum antibody response is reached when, in a stable immunogenic product such as described hereinabove, less than 40% of the molecules of the antigen of interest are covalently linked to the carrier protein molecules. According to the invention, an antigenic molecule of interest is covalently linked to a carrier protein molecule by "one" covalent bond means that said molecule of antigen of interest is covalently linked, chemically, to said carrier protein molecule, by at least one covalent bond, i.e. optionally by two covalent bonds or more.

The percentage of carrier protein molecules and of antigenic protein proteins of interest linked between one another through covalent bonds in an immunogenic product of the invention can be easily checked by the man of the art.

For example, determining the percentage of antigenic molecules of interest linked to the carrier protein molecules through a covalent link in an immunogenic product of the invention could be made using the following steps of:

(i) submitting said immunogenic product in solution to denaturing and reducing conditions;

(ii) performing a size exclusion chromatography step with the product as obtained at the end of step (ii) during which the various protein components with decreasing molecular mass are successively eluted from the size exclusion chromatography support;

(iii) measuring the amount of antigen of interest linked through a covalent bond to the carrier molecule in the eluate fraction containing the protein components with the highest molecular mass;

(iv) comparing the amount of antigen of interest measured in step (iii) with the total amount of antigen of interest initially included in the starting immunogenic product.

In step (i) of the method for determining the above-described covalent link percentage, incubating a given amount (in number of moles or in weight) of the immunogenic product of the invention under denaturing and reducing conditions leads to a disassociation of the weak bonds between the various protein components not linked between one another through a covalent bond.

Amongst preferred denaturing conditions there is the presence of urea, for example, in the final 8M concentration, or the presence of SDS, for example, in the 1% final concentration in total weight of the solution containing the immunogenic product. Amongst preferred reducing conditions there is the presence of β-mercaptoethanol, for example in the 5% final concentration of the total volume of the solution containing the immunogenic product.

In step (ii) of the method for determining the percentage of molecules of antigen of interest and molecule of carrier protein linked between one another through covalent bonds, the size exclusion chromatography support is selected by the man of the art according to his technical general knowledge. For example, the man of the art could make use of chromatographic supports as marketed by the Pharmacia Corporation under the "Superdex 75™" and "Superdex 200™" trademarks.

In step (ii), the molecular fraction corresponding to the carrier molecule covalently linked to the molecules of antigen of interest is eluted first, before the eluate fraction(s) containing the antigen of interest under a free form. The antigen of interest being eluted under a free form corresponds to the fraction of the antigen of interest, which was not covalently linked to the carrier molecule, within the starting immunogenic product. It is on the high molecular mass protein fraction that occurs the measurement of the amount of the antigen of interest covalently linked to the carrier protein molecule, for example, in an immuno-enzyme test, in a radioimmunologic test or in an immunofluorescence test, either direct or indirect ("sandwich"), using antibodies specific to the antigen of interest and which do not have any immunologic reaction crossed with the carrier protein molecule.

In step (iii), the amount of the antigen of interest covalently linked with the carrier protein molecule, being measured as described hereinabove, is compared with the initial amount of the antigen of interest being included in the given amount (in number of moles or in weight) of the starting immunogenic product and the percentage of the antigen of interest is thereby calculated, which is covalently linked to the carrier protein molecule, in the immunogenic product of the invention.

The percentage of carrier protein molecules and of antigenic protein proteins of interest linked between one another through covalent bonds, in an immunogenic product of the invention, can be easily checked by the man of the art, making use of a second method comprising the following steps of:

a) immobilizing on a support of specifically antibodies raised against the carrier protein;

b) bringing into contact the antibodies raised against the carrier protein, which were immobilized on the support in step a), with a known amount of molecules of the immunogenic product to be tested comprising said carrier protein and an antigenic protein of interest;

c) removing the molecules of the immunogenic product which are not linked to the anti-carrier protein antibodies immobilized in step a), by means of a buffering aqueous solution comprising one ore more protein denaturing agents;

d) d1) bringing into contact (i) immunogenic complexes formed in step c) between the immobilized anti-carrier protein antibodies and the molecules of the immunogenic product with (ii) antibodies specifically raised against the carrier protein;

d2) separately from step d1), bringing into contact the immunogenic complexes formed in step c) between the immobilized anti-carrying protein antibodies and the molecules of the immunogenic product with (ii) antibodies specifically raised against the antigenic protein of interest;

e) e1) quantifying the antibodies added in step d1) having been linked to the carrier protein;

e2) quantifying the antibodies added in step d2) having been linked to the antigenic protein;

f) calculating the ratio between:

(i) the amount of anti-carrier protein bound antibodies measured in step e1); and (ii) the amount of anti-carrier protein bound antibodies measured in step e2), said ratio consisting in the proportion of carrier protein molecules and antigenic protein molecules of interest being linked between one another through covalent bonds, within the starting immunogenic product.

In step c) of the above described method, the use of an aqueous washing solution containing one or more protein denaturing agents leads to a denaturation of the immunogenic product linked to the anti-carrier protein antibodies, resulting in the release, in the washing solution, of antigenic protein molecules of interest which are not covalently linked to the carrier protein molecules. Therefore, in step d2) of the method, only the antigenic protein molecules of interest being covalently linked to the carrier protein molecules are quantified.

Preferably, the denaturing buffering solution used in step c) contains a surfactant such as Tween®20, in a final concentration of 0.1% v/v.

in steps d1) and d2), the amounts of bound antibodies are preferably measured through incubating antigen-antibodies complexes formed at the end of each of said steps with a new antibody being labeled through a detectable molecule, respectively:

(i) in step d1), a new antibody directed against an the anti-carrier protein antibody and labeled with a detectable molecule;

(ii) in step d2), a new antibody directed against an antibody anti-antigenic protein of interest and labeled with a detectable molecule.

The detectable molecule is indiscriminately either a radioactive molecule, a fluorescent molecule or an enzyme. As an enzyme, peroxydase could more particularly be used, its presence being revealed through colorimetry, after incubation with the ortho-phenylenediamine (OPD) substrate.

A detailed protocol of the above-mentioned method is described in the examples.

By way of illustration, it has been shown according to the invention, using the first or the second above described quantification methods that:

in the immunogenic product comprising heterocomplexes between the KLH carrier molecule and human alpha interferon molecules, from 3 to 8% of the alpha interferon molecules are covalently linked to the KLH carrier protein molecule;

in the immunogenic product comprising the heterocomplexes between the KLH carrier protein molecule and murine IL-4 molecules, about 11% of the IL-4 molecules are covalently linked to the KLH carrier protein molecule.

Obviously, depending on the preparations, the percentage of molecules of antigenic protein of interest covalently linked to the carrier protein molecules could significantly vary. However, in all cases, such a percentage is always lower than 40%.

The object of the invention is to provide a stable immunogenic product for inducing antibodies raised against one or more antigenic proteins in a subject, characterized in that it comprises protein immunogenic heterocomplexes comprising associations between (i) antigenic protein molecules and (ii) carrier protein molecules and in that less than 40% of the antigenic proteins (i) are covalently linked to carrier protein molecules (ii).

Another object of the invention is also to provide an immunogenic product comprising stable protein immunogenic heterocomplexes for inducing antibodies raised against one or more antigenic proteins in a subject, each heterocomplex comprising (i) a plurality of antigenic proteins, linked to a (ii) carrier protein molecule, characterized in that less than 40% of the antigenic proteins (i) are covalently linked to carrier protein molecules (ii).

Most preferably, the antibodies with their production being induced by the immunogenic product of the invention comprise "neutralizing" or "blocking" antibodies. A "neutralizing" or a "blocking" antibody is defined, according to the invention, as an antibody the binding of which on the native protein blocks the biological activity of such a native protein, which is an important objective being sought by the invention, when the native protein against which the antibodies are raised has a deleterious biological activity for the organism, within the targeted pathological context of an individual to be treated, for example, when the native protein has an angiogenic activity, an immunosuppressive activity, as well as an allergenic activity, more particularly an interleukin-4 production inducing activity.

A "carrier protein molecule", included in the immunogenic product of the invention, means any protein or peptide being at least 15 amino acids long, whatever its amino acid sequence, and which, when partially covalently being associated to the molecules of the antigen of interest for forming protein heterocomplexes making up the immunogenic product of the invention, allows for a large number of molecules of the antigen of interest to be presented to the B lymphocytes.

According to a first aspect, the carrier protein molecule consists in one protein or one peptide being at least 15 amino acid long, or also an oligomer of such a peptide, comprising one or more auxiliary T epitopes ("helper") able to activate auxiliary T lymphocytes ("T helper") of the host organism for producing cytokins, including interleukin 2, such cytokins, in turn, activating and inducing the proliferation of B lymphocytes, which, after maturation, will produce antibodies raised against the antigenic protein (i).

According to a second aspect, a carrier protein molecule consists in one protein or one peptide being at least 15 amino acid long, or also an oligomer of such a peptide, comprising besides one or more auxiliary T epitopes ("helper"), as described in the above-mentioned first aspect, one or more cytotoxic T epitopes, able to induce a cell immune response through the production of cytotoxic T lymphocytes specific of the carrier protein molecule, such lymphocytes being able to specifically recognize cells expressing on their surface said carrier protein or any peptide being derived therefrom, in association with class 1 Histocompatibility Major Complex (HMC) molecules. If need be, the carrier protein molecule consists in one oligomer of one protein or one peptide, further comprising besides one or more T helper epitopes, one or more above defined cytotoxic T epitopes.

According to a third aspect, a carrier protein molecule consists in one protein or one peptide being at least 15 amino acid long, as well as one oligomer of such a peptide, comprising besides one or more auxiliary T epitopes ("helper") as defined in the first aspect, one or more B epitopes, able to induce the production of antibodies by lymphocytes raised against the carrier protein.

In some embodiments, the carrier protein, besides its T helper, used for activating an antibody response against the antigen of interest, could also activate a cytotoxic response against cells carrier peptides of the carrier and/or stimulate an antibody response against such a carrier protein molecule.

The carrier protein molecule could also consist in a homo-oligomer or a homo-polymer of the native protein, from which it is derived, as well as a homo-oligomer or a homo-polymer of a peptide fragment of the native protein, from which it is derived. The antigenic protein of interest could also consist in a hetero-oligomer or a hetero-polymer comprising a combination of several distinct peptide fragments initially included in the native protein from which it is derived.

As used herein, the expression "antigenic protein" means any protein or any peptide being at least 10 amino acid long, including a hapten peptide, able to be specifically recognized by receptors for the antigens expressed by the B lymphocytes of a host organism, whether human or animal, more particularly a mammal, such antigenic protein, once included in an immunogenic product of the invention, stimulating the production of antibodies recognizing said antigenic protein.

It is meant under "antigenic protein" any protein comprising one or more B epitopes of the native antigenic protein against which the production of antibodies if being sought. Said antigenic molecule of interest could consist in the native protein itself or a protein derivate of the native protein, such as a peptide fragment of the native protein, as well as any biologically inactivated form of the native protein obtained through chemical, physical treatment or genetic mutation. The antigenic molecule of interest could also consist in a homo-oligomer or a homo-polymer of the native protein as well as a homo-oligomer or a homo-polymer of a peptide fragment of the native protein. The antigenic protein of interest could also consist in a hetero-oligomer or a hetero-polymer comprising a combination of several distinct peptide fragments initially included in the native protein.

In an immunogenic product according to the invention, advantageously, less than 30% and preferably less than 20% of antigenic proteins (i) are covalently linked to the carrier protein molecules (ii).

In an immunogenic product according to the invention, advantageously, at least 1%, and preferably at least 2%, of the antigenic proteins (i) are covalently linked to the carrier molecules (ii).

It has been shown that an immunogenic product according to the invention, such as hereinabove defined, is stable in an aqueous solution. The stability of an immunogenic product of the invention is more particularly characterized in that said immunogenic product has its own isoelectric point, distinct from the isoelectric point of at least one of its protein components, respectively the antigenic protein (i) and the carrier protein molecule (ii), and in that it therefore migrates according to a distinct protein strip from at least one of its protein strips respectively corresponding to both protein components making it up in isoelectrofocusing trials.

It has also been shown, through immunoblotting trials ("Western blot"), that the immunogenic product of the invention migrates in an electrophorese gel, under non denaturating conditions, according to a single protein strip, which illustrates the fact that said immunogenic product has the form of a homogeneous population of soluble protein constructions.

Moreover, it has been shown that the antigenic protein (i) as well as the protein molecule (ii) included under the form of protein heterocomplexes in the immunogenic product of the invention were both recognized by antibodies specifically recognizing each of such proteins. Thus, the immunogenic product according to the invention comprises the antigenic protein (i) and the carrier protein molecule (ii) in their native structure. Such a technical feature of the immunogenic product according to the invention is particularly advantageous for inducing an immune response against native antigens, i.e. an efficient and truly protective immune response of the host organism. It has been more particularly shown that an immunogenic product according to the invention induces, in the host organism to which it is administered, the induction of a strong efficient humoral response against native antigens, associated to the production of neutralizing or blocking antibodies, towards the deleterious biological activity of such native antigens.

It has been shown according to the invention, with various antigens of interest, that the humoral immune response obtained using an immunogenic product such as defined hereinabove, was 10 to 1000 times higher than the humoral immune response obtained with the administration of a conventional covalent conjugate between the antigen of interest and the carrier protein molecule.

Preferably, in an immunogenic heterocomplex included in the immunogenic product of the invention, the plurality of antigenic proteins (i) is made up of a plurality of specimens of a single antigenic protein.

Thus, according to a most preferred embodiment, the immunogenic product of the invention is implemented for obtaining specific antibodies raised against a single antigen of interest.

It has also been shown according to the invention that an immunogenic product comprising immunogenic heterocomplexes such as hereinabove defined, is particularly well adapted to the immunization of an individual, through the production of antibodies, against a "self antigen" of interest, i.e. against a protein being naturally produced by said individual, for which there exists a tolerance of the immune system, in particular an at least partial deletion of auxiliary lymphocyte T clones (T helper cells) specifically recognizing said antigen.

In other words, the presentation of the "self" antigen to the cells of said individual's immune system, under the form of an immunogenic product comprising immunogenic heterocomplexes of the invention, allows to "break" the tolerance of the individual's immune system towards such an antigen. Without wishing to be bound to any theory, the Applicant believes that the opportunity to obtain a high level of antibody response against a "self" antibody is due to the presence within the heterocomplex of numerous epitopes of the "auxiliary T" type (or T helper) carried by the carrier protein molecule, activating the auxiliary T lymphocytes, and the various cytokins produced by the activated auxiliary T lymphocytes, including IL-2, allows to promote some activation of the B cells to "self" antigens present in the latent state within the organism, and to thereby break the immune tolerance of B cells to "self" antigens.

Thus, according to a preferred embodiment, the immunogenic product of the invention is characterized in that the antigenic proteins (i) consists in a plurality of specimens of a protein being normally recognized as a self protein by the cells of said subject's immune system.

As the major proportion, more than 60%, of associations between the antigen of interest and the carrier protein molecule, occurs through non covalent interactions, there exists no other theoretical limitation in the number of molecules of the antigen of interest associated with a single carrier protein molecule, than the steric availability of the molecules of the antigen of interest to such a carrier molecule. In particular, the number of molecules of the antigen of interest associated to a single carrier protein molecule is not limited by the number of chemically reactive functions carried by the carrier molecule allowing for creating covalent links with a plurality of molecules of the antigen of interest. Consequently, the only physical limitation seems to be the number of sites of the carrier protein molecule (ii) available to the antigenic protein (i).

For the same reasons, the size of the antigen of interest to be associated to the carrier protein molecule is not either strictly limited, the antigen of interest consequently being able to consist in full proteins of at least 10 kDa, such as the various cytokins, as IL-4, IL-10, VEGF as well as the alpha interferon.

Moreover, even for the antigens of interest consisting in full proteins with a molecular mass higher than 10 kDa, an immunogenic heterocomplex of the invention can comprise an association of several antigens of interest on a single carrier molecule, if the size of the carrier molecule makes it possible.

When the carrier protein molecule has a small size, for example a size lower than 10 kDa, or even lower than 5 kDa, the Applicant believes, without wishing to be bound to any theory, that the partially covalent associations between the antigen of interest and said carrier protein, forming the protein heterocomplexes included in the immunogenic product of the invention, allow for such a conformation of heterocomplexes that both the antigen of interest and the carrier protein molecule are available to receptors of the immune system cells.

This is even an additional technical advantage provided to the immunogenic product comprising heterocomplexes such as hereinabove defined, as the presentation to B lymphocytes of a plurality of specimens on one single carrier molecule, included in the heterocomplex, enhances the "capping" phenomenon through "cross-linking" of receptors of the B cell recognizing the antigen, contributing to the activation of the B cell receiving, in addition, activation signals coming from cytokins produced by the activated auxiliary T lymphocytes activated by means of auxiliary T epitopes carried by carrier protein molecule.

Thus, according to a most preferred embodiment of the immunogenic product, the latter comprises 5 to 50 antigenic proteins (i) for one carrier protein molecule (ii), preferably 20 to 40 antigenic proteins (i) for one carrier protein molecule (ii).

The number of molecules of the antigen of interest on one single carrier protein molecule respectively depends on the size of the carrier molecule and on the size of the molecule of the antigen of interest. The bigger the carrier molecule is and offers a large association surface with the antigen of interest, the more the immunogenic heterocomplex will comprise, for one single of the carrier molecules it contains, a higher number of specimens of the molecule of the antigen of interest. Similarly, the more reduced the size of the molecule of the antigen of interest is, the larger the number of specimens will be of the molecule of the antigen of interest on the same carrier molecule.

By way of illustration, it has been shown according to the invention that when the carrier protein molecule is KLH, 20 to 40 molecules of IL-4, IL-10, alpha interferon or VEGF are associated to each carrier molecule.

It has been shown that the solubility of the immunogenic product in an aqueous solution varies with the modification of the balances mastering the molecular interactions within heterocomplexes, more particularly the electrochemical balances depending on the so-called "weak" (non covalent) links as well as the respective concentrations in antigenic proteins and the carrier protein molecule, as well as with the conditions of ionic strength, pH and temperature.

Preferably, the covalent bonds between one or more antigenic proteins (i) and the carrier protein molecule (ii) occur by means of a bifunctional bonding chemical agent.

Such a chemical agent could be cyanogen bromide, glutaraldehyde, carbodiimide, or succinic anhydride.

As for carbodimides, the following compounds could be used: 1-cyclohexyl-3-(2-morpholinyl-(4-ethyl)carbodiimide (CMC), 1-ethyl-3-(3-dimethyaminopropyl)carbodiimide (EDC) and 1-ethyl-3-(4-azonia-4,4-limethylpentyl)carbodiimide, 1-cyclohexyl-3-(2-morpholinyl-(4-ethyl)-carbodiimide, (1-ethyl-3-(3-dimethyaminopropyl carbodiimide (EDC) and 1-ethyl-3-(4-azonia-4,4-dimethylpentyl)carbodiimide.

As homo-bifunctional coupling agents, the following compounds could be used:

N-hydroxysucciinimide, dithiobis (succinimidylpropionate) esters, disuccinimidyl suberate, and disuccinimidyl tartrate; bifunctional imidoesters dimethyl adipimidate, dimethyl pimelimidate, and dimethyl suberimidate;

reagents with a sulphydryl, 1,4-di-[3'-(2'-pyridyledithio) propionamido]butane, bismaleimidohexane, and bis-N-maleimido-1,8-octane;

bifunctional halides of the aryl type and 4,4'-difluoro-3,3'-dinitrophenylsulfone;

SMCC (succinimidyl-4-(N-maleimidomethyl)cyclohexane-1-carboxylate);

SIAB (N-succinimidyl(4-iodoacetyl)aminobenzoate);

SMPB (succinimidyl-4-(p-maleimidophenyl)butyrate);

GMBS (N-(.gamma.-maleimidobutyryloxy)succinimide ester);

MPBH (4-(4-N-maleimidophenyl) hydrazide butyric acid);

M2C2H (4-(N-maleimidomethyl)cyclohexane-1-carboxyl-hydrazide);

SMPT (succinimidyloxycarbonyl-alpha-methyl-alpha-(2-pyridyl-dithio)toluene); and SPDP (N-succinimidyl 3-(2-pyridyldithio)propionate).

Preferably, the bonding chemical agent to be used comprises at least two reactive aldehyde functions.

Most preferably, the bonding chemical agent is glutaraldehyde.

After the product comprising protein heterocomplexes has been formed through a coupling of carrier protein molecules with antigenic proteins with the use of the bonding chemical agent, the resulting product could be stabilized by means of a protein stabilizing agent, such as formaldehyde, able to create intrachain bonds.

The immunogenic products comprising immunogenic heterocomplexes of the invention have the form of microparticles soluble in solution, in particular in an aqueous solution, their average size varying depending on (i) the size of the carrier protein molecule, (ii) the size and the number of antigenic proteins associated to one single carrier protein molecule and (iii) the number of carrier molecules associated to the antigenic proteins present in a heterocomplex particle.

It has been found that the heterocomplex microparticles described in the examples have an average size ranging from 100 nm to 300 nm.

Most preferably, an immunogenic product comprising immunogenic protein heterocomplexes of the invention exclusively comprises carrier molecules associated to antigenic proteins, with the exclusion of any other material. More particularly, a heterocomplex of the invention does not comprise any other polymeric, proteinaceous or non proteinaceous material, other than the carrier and antigenic proteins characterizing it.

Recently, ZAGURY D et al. (2001, Proc. Nail. Acad. Sci. USA. 98(14):8024-8029), in a bibliographical study, suggested to induce an anti-cytokin immunity in patients in order to counteract the abnormal production in such pathologies of some cytokins, including interleukins, lymphokins, monokins, interferons, physiologically acting in the tissues, locally as a factor of programmed cell proliferation, differentiation, or death.

The above-mentioned authors state that the strategies of vaccine therapy were, until now, exclusively focused on the antigenic aggressor, whether it is a micro-organism, a cell or an allergen, but never attempted to fight the deregulation of cytokins induced under the effect of the aggressor. Said authors suggest an anti-cytokin vaccination as a prior step to a conventional vaccination having as an aim to neutralize or block the immunotoxic effect of the stroma, and to allow for the normal occurrence of the immune reaction adapted towards the antigenic aggressor.

Moreover, the Applicant's prior work, mentioned in the International Application published under WO 00/03732, showed that in the case of ATL leukemia, the neck of the uterus cancer and the Kaposi sarcoma, respectively, three proteins are involved in a local immunosuppression at the level of tumors or HIV1 infected cells:

the HTLV1 virus Tax protein,
the papillomavirus E7 protein, and
the V1H-1 virus Tat protein.

The Applicant also stated that some of such immunosuppressive proteins, such as the HIV1 Tat protein and the HPV E7 protein (Strains 16 and 18) also have activating effects on vascular endothelial cells.

They therefore suggested developing anti-cancer or antiviral vaccines comprising a detoxicated immunogenic compound derivate of a protein coming from cancer cells, from virus infected cells or stroma immune cells, initially immunosuppressive and/or angiogenic with a local action, as, for example, a protein derived from the H1V1 virus Tat protein, the HTLV1 virus Tax protein, papillomavirus E7 protein as well as a mannan-depending lectin under an inactivated form.

Now, it has been shown according to the invention that the immunogenic product comprising immunogenic heterocomplexes such as hereinabove defined allows for the induction of a strong antibody response against the various above-mentioned deleterious antigenic molecules.

According to a first aspect, in the immunogenic heterocomplex of the invention, the antigenic protein(s) (i) consist(s) in cytokins naturally produced by said subject.

Preferably, the antigenic protein(s) (i) is/are selected from interleukin-4, alpha interferon, gamma interferon, VEGF, interleukin-10, alpha TNF, beta TGF, interleukin-5 and interleukin-6.

According to a second aspect, the antigenic protein(s) (i) making up an immunogenic heterocomplex of the invention is/are immunosuppressive or angiogenic proteins, or proteins derived from immunosuppressive or angiogenic proteins.

Preferably, the antigenic protein(s) (i) is/are selected amongst a papillomavirus E7 protein, the VIH 1 virus Tat protein, the HTLV 1 or HTLV 2 virus Tax protein, and the self p53 protein.

According to a third aspect, the antigenic protein(s) (i) making up an immunogenic heterocomplex according to the invention is/are proteins being toxic at a low dose to man or to a non human mammal. These are more particularly various proteins being lethal to man at a dose lower than 1 mg, lower than 100 µg, lower than 10 µg, even lower than 1 µg. These are predominantly toxic proteins able to be used for manufacturing so-called "biological" weapons, such as ricin, botulic toxins, *staphylococcus* enterotoxins, as well as an anthrax toxic protein (EF, LF, PA).

The carrier protein molecule (ii) included in an immunogenic protein heterocomplex of the invention could be a carrier molecule conventionally used in immunology, such as KLH, ovalbumin, bovine serum albumin (BSA), toxoid tetanos, B cholera toxin, etc.

Moreover, in an immunogenic product of the invention, the protein carrier molecule could be selected so as to induce or stimulate, besides the production of T helper lymphocytes, a cytotoxic and/or humoral immune response against itself, and its counterpart of native protein in the host organism, respectively through the activation of cytotoxic T lymphocytes and of B lymphocytes specific to such a carrier molecule.

Such a particular embodiment of an immunogenic product of the invention is particularly useful when there is simultaneously sought an efficient antibody response against an immunosuppressive or angiogenic deleterious protein, more particularly, for producing neutralizing or blocking antibodies, and a cell immune response generated by cytotoxic T lymphocytes raised against cells having at their surface the native antigen associated to Major Histocompatibility Complex (MHC) class I molecules, for example, an antigen of a pathogen, such as the VIH1 virus or a papillomavirus, or an antigen specifically expressed in cancer cells such as CEA, p53, Di12, etc.

Thus, according to this particular embodiment, the immunogenic product of the invention is characterized in that the carrier protein molecule (ii) is an immunogenic protein inducing, besides the production of T helper lymphocytes, the production of cytotoxic T lymphocytes raised against cells having at their surface said carrier protein molecule, or any peptide being derived therefrom, in association with Major Histocompatibility Complex (MHC) class I molecules and/or the production of antibodies by B lymphocytes raised against the carrier protein.

Thus, immunogenic products comprising immunogenic heterocomplexes of the invention are efficient immunologic means for the active therapeutic vaccination of an individual, whether a human mammal or a non human mammal, against a large variety of pathologies.

Illustrative examples of such immunogenic heterocomplex compositions contained in an immunogenic product according to the invention for preventing or treating, through an active therapeutic vaccination, various pathologies are mentioned hereinafter.

a) For Preventing or Treating AIDS:

Carrier protein molecule (ii): gp 120, gp 160, p24, p17, nef or Tat proteins of HIV1 virus, detoxicated or stabilized if required, immunogenic fragments of such proteins as well as an immunogenic protein being derived therefrom (Zagury et al., 1998).

The mimotope gp120 protein could also be used as described by Fouts et al. (2000) and by Fouts et al. (2002).

Antigenic protein (i): Tat, IFNα, IL10 and TGFβ proteins, detoxicated if required, immunogenic fragments of such proteins, or an immunogenic protein being derived therefrom.

b) For Preventing or Treating the Neck of Uterus Cancer:

Carrier protein molecule (ii): papillomavirus L1, L2 and E7 proteins, preferably a papillomavirus from strain 16 or 18, detoxicated or stabilized if required, immunogenic fragments of such proteins as well as an immunogenic protein being derived therefrom (Le Buanec et al., 1999).

Antigenic protein (i): E7, IFNα, IL10, TGFβ, TNFα and VEGF proteins, detoxicated or stabilized if required, immunogenic fragments of such proteins as well as an immunogenic protein being derived therefrom.

c) For Preventing or Treating ATL Leukemia Induced by the HTLV1 or 2 Viruses:

Carrier protein molecule (ii): gp61 and HTLV1 or 2 virus Tax proteins, detoxicated if required, immunogenic fragments of such proteins as well as an immunogenic protein being derived therefrom (Cowan et al., 1997; Mori et al., 1996).

Antigenic protein (i): Tax, IL10, IFNα or TGFβ, TNFα, VEGF proteins, detoxicated if required, immunogenic fragments of such proteins as well as an immunogenic protein being derived therefrom.

d) For Preventing or Treating Colon Cancer:

Carrier protein molecule (ii): CEA and p53 proteins, detoxicated if required, immunogenic fragments of such proteins as well as an immunogenic protein being derived therefrom (Zusman et al., 1996)).

Antigenic protein (i): IFNα, TGFβ, IL10, FasL and VEGF proteins, detoxicated if required, immunogenic fragments of such proteins as well as an immunogenic protein being derived therefrom.

e) For Preventing or Treating Breast Cancer:

Carrier protein molecule (ii): Di12 protein, immunogenic fragments of such a protein as well as an immunogenic protein being derived therefrom (Yoshiji et al., 1996).

Antigenic protein (i): IFNα, TGFβ, IL10, FasL and VEGF proteins, detoxicated if required, immunogenic fragments of such proteins as well as an immunogenic protein being derived therefrom.

f) For Preventing or Treating Pancreas Cancer:

Carrier protein molecule (ii): CaSm protein, detoxicated if required, immunogenic fragments of such proteins as well as an immunogenic protein being derived therefrom.

Antigenic protein (i): VEGF and TNFα proteins, detoxicated or stabilized if required, immunogenic fragments of such proteins as well as an immunogenic protein being derived therefrom.

g) For Preventing or Treating Prostate Cancer:

Carrier protein molecule (i): OSA and ETS2 proteins, detoxicated or stabilized if required, immunogenic fragments of such proteins as well as an immunogenic protein being derived therefrom. (Sementchenko V I et al., 1998).

Antigenic protein (i): IL6 and TGFb proteins, detoxicated or stabilized if required, immunogenic fragments of such proteins as well as an immunogenic protein being derived therefrom (Adler et al., 1999).

h) For Preventing or Treating Some Allergies:

Carrier protein molecule (ii): it is selected amongst molecular allogens, such as Bet v 1 (birch-tree pollen), Der p 1 (acarid) and Fel d 1 (cat) proteins, their immunogenic peptide fragments as well as an immunogenic protein being derived therefrom. The Bet v 1 antigen is described more particularly by Ferreira et al. (1993), the Der p 1 antigen is described, in particular, by Tovey et al. (1981) and the Fel d 1 antigen is described, more particularly by Morgensterm et al. (1991)

Antigenic protein (i): it induces the production of neutralizing or blocking antibodies raised against the IL4 cytokin factor, being mainly produced by T lymphocytes of Th2 type, orienting the humoral immune response towards the production of IgE isotype antibodies. According to another embodiment, the antigenic protein (i) induces the production of neutralizing or blocking antibodies against the IL5 cytokin factor, being mainly produced by T lymphocytes of Th2 type.

According still another embodiment, preventing allergy could occur by means of an immunogenic product inducing an antibody response against the main basophil granulation effector, i.e. IgE isotype antibodies. For this purpose, the invention provides an immunogenic product comprising (i) an IgE isotype human antibody and (ii) the VIH1 inactivated Tat protein.

i) For the Prevention Against Lethal Proteins Used in Biological Weapons

Also, an immunogenic product according to the invention could be used for immunizing individuals against numerous toxic products used, in particular, in chemical and biological weapons, as for example, ricin.

Amongst the most toxic proteins against which an immunization, mainly through the production of antibodies, is being sought, botulic toxins, ricin, *staphylococcus* enterotoxins, *Clostridium perfringens* toxins and anthrax toxic proteins.

Generally speaking, for producing an immunogenic product according to the invention, wherein the antigenic protein (i) is a highly toxic protein of the above-mentioned type, a previously detoxicated protein is used under the form of a toxoid. For detoxicating the protein, before its use for producing an immunogenic product according to the invention, various methods could be used, and preferably one of the following methods consisting in:

a) treating the native toxic protein by glutaraldehyde;

b) treating the native toxic protein through the combined action of formol and glutaraldehyde; or c) if need be, through chemical modification of His and Tyr groups by means of appropriate reagents, for example, through carboxymethylation of such amino acid residues.

For preventing the lethal action of toxins originating from *Bacillus anthracis*, as proteins, antigenic proteins (i), a detoxicated protein originating from an anthrax protein selected amongst EF ("Edema Factor"), LF ("Lethal Factor") and PA ("Protective Antigen") proteins are used preferably.

For preventing the lethal actions of proteins originating from *Clostridium perfringens*, as the antigenic protein (i), a detoxicated protein originating from the Epsilon toxin of *Clostridium perfringens* are preferably used.

For preventing the lethal action of toxins originating form *Clostridium botulinum*, as antigenic proteins (i), a detoxicated protein originating from a botulic toxin selected amongst A, B, C, D, E, F and G toxins being naturally synthesized in the form a single 150 kDa polypeptide chain as well as the Hc fragment of such botulinic toxins, said fragment Hc having a molecular mass of approximately 50 kDa, are preferably used.

For producing inactivated botulic toxins, the man of the art could use techniques known per se, more particularly those used for preparing the anterior vaccine compositions, such as those described by Fiock et al. or by Siegel et al. (Fiock, M. A., Cardella, M. A., Gearinger, N. F., J. Immunol., 1963, 90, 697-702; Siegel, L. S., J. Clin. Microbiol., 1988, 26, 2351-2356).

For preventing the lethal action of toxins originating from ricin seed (*Ricinus communis*), as the antigenic protein (i), a detoxicated protein originating from the ricin toxin, preferably the β fragment of ricin, is preferably used.

Thus, the invention also provides an immunogenic product comprising (i) the β fragment of ricin and (ii) the KLH protein.

For purifying ricin, the man of the art could use any known technique, such as those described by Osborne et al., Kabat et al. or Kunnitz et al. (Osborne, T. B., Mendel, L B. and Harris, J. F.: Amer. J. Physiol., 1905, 14, 259-269; Kabat, E. A. Heidelberger, M. and Bezer, A. E.: J. Biol. Chem., 1947, 168, 629-; Kunnitz, M. and McDonald, M.: J. Gen. Physiol., 1948, 22, 25-Moulé, Y.: Bull. Soc. Chim. Biol., 1951, 33, 1461-1467). He could also make use of the affinity chromatography purification techniques described by Tomila et al., Nicolson et al. or Olsnes et al. (Tomila, M., Kurokawa, T., Onozaki, K. et al.,: Experientia, 1972, 28, 84-85; Nicolson, G. L. and Blaustein, J.: J. Biochim. Biophys. Acta, 1972, 266, 543-547; Olsnes, S., Salvedt, E. and Pihl, A.: J. Biol. Chem., 1974, 249, 803-810). The ricin A and B chains could be purified as described by Hedge et al. (Hedge, R. and Podder, S. K.: Eur. Biochem., 1998, 254, 596-601).

For preventing the lethal action of toxins originating from *staphylococcus* and more particularly from *Staphylococcus aureus*, as the antigenic protein (i), a detoxicated protein originating from a toxin selected amongst SEA ("Staphylococcal Enterotoxin A"), SEB ("Staphylococcal Enterotoxin B"), SEC ("Staphylococcal Enterotoxin C"), SED ("Staphylococcal Enterotoxin D"), SEE ("Staphylococcal Enterotoxin E"), SEG ("Staphylococcal Enterotoxin G"), SEH ("Staphylococcal Enterotoxin H"), SEI ("Staphylococcal Enterotoxin I") and TSST-1 ("Toxic Shock Syndrome Toxin-1") is preferably used.

The above listed enterotoxins could be prepared by the man of the art by means of techniques described in the listed work below, relating to the description of each of such toxins.

SEA is synthesized in the form of a precursor enterotoxin with 257 amino acids (Huang, I.Y., Hughes, J. L, Bergdoll, M. S. and Schantz, E. J. J. Biol. Chem. 1987, 262, 7006-7013). The mature toxin with a molecular mass equal to 27,100 Da derives from the precursor toxin through the loss of a N-terminal hydrophobic leader sequence with 24 amino acid residues (Betley, M. J. and Mekalanos, J. J. J. Bacteriol., 1998, 170. 34-41). SEA exists under 3 different isoforms through their IP.

The SEB precursor protein comprises 267 amino acids (Mr=31,400 Da) with a N-terminal signal peptide with 27 amino acids. Its binding site to the receptor of T cells ("T-Cell Receptor" or "TCR") encompasses the shallow cavity, whereas the class II MHC molecule is fixed on an adjacent site (Kappler, J. W., Herman, A., Clements, J. and Marrack, P.: J. Exp. Med., 1992, 175, 387-396; Papageorgiu, A. C., Trauter, H. S. and Acharya, K. R. J. Mol. Biol., 1998, 277, 61-79; Soos, J. M. and Johnson, H. M. Biochem. Biophys. Res. Commun., 1994, 201, 596-602).

SEC possesses 3 antigenically distinct sub-types: SEC 1, SEC 2 et SEC 3. The precursor proteins contains 267 amino acid residues (Houde, C. J., Hackett, S. P. and Bohach, G. A. Mol. Gen. Genet., 1990, 220, 329-333) with a signal peptide with 27 amino acid residues (Bohach, G. A. and Schlievert, P. M.: Infect. Immun., 1989, 57, 2243-2252).

SED is made up of 258 amino acid residues with a signal peptide of 30 amino acid residues. Its three-dimension structure is similar to the structure of other bacterial superantigens.

SEE having a 26,000 Da molecular mass have 81% of AA sequence homology with SEA.

SEG is made up of 233 amino acid residues (Munson, S. H., Tremaine, M. T., Betley, M. J. and Welch, R. A.: Infect. Immun., 1998, 66, 3337-3348).

SEH has a 27,300 Da molecular mass (Su, Y. C. and Wong, A. C.: Aplil. Environ. Microbiol., 1995, 61, 1438-1443). It does not have any crossed immunologic reaction with other enterotoxins.

SEI has a sequence comprising 218 amino acid residues. This is the toxin with the lowest homology level with other enterotoxins SEJ made up of 269 amino acid residues has a high AA sequence homology with SEA, SEE and SED (64-66%).

Preferably, an immunogenic product according to the invention comprises, in combination, several antigenic proteins (i) each derived from an above-mentioned toxic protein, for example, 2, 3, 4 or 5 antigenic proteins (i) each derived from an above listed toxic protein.

For example, an immunogenic product according to the invention for preparing a vaccine composition intended for preventing the toxicity of *staphylococcus* enterotoxins preferably comprises 2, 3, 4 or 5 antigenic proteins (i) each derived from a *staphylococcus* enterotoxin.

According to a particular embodiment of an immunogenic product according to the invention, wherein the antigenic protein(s) (i) is/are derived from highly toxic proteins for man; the carrier protein is the KLH protein.

Thus, according to a first particular aspect of an immunogenic product of the invention, wherein the carrier protein molecule both induces the production of auxiliary T lymphocytes ("T helper"), of cytotoxic T lymphocytes and of B lymphocytes specific to the carrier protein molecule, said carrier protein molecule (ii) is selected amongst the papillomavirus L1, L2, and E7 proteins.

Thus, according to a second particular aspect of an immunogenic product of the invention, wherein the carrier protein molecule induces, in addition to the production of auxiliary T lymphocytes ("T helper"), the differentiation of cytotoxic T lymphocytes and of B lymphocytes specific to the carrier protein molecule, said carrier protein molecule (ii) is selected amongst the HIV1 virus gp160, p24, p17, Nef and Tat proteins.

Thus, according to a third particular aspect of an immunogenic heterocomplex of the invention, wherein the carrier protein molecule both induces the production of auxiliary T lymphocytes ("T helper"), of cytotoxic T lymphocytes and of B lymphocytes specific to the carrier protein molecule, said carrier protein molecule (ii) is selected amongst CEA, p53, Di12, CaSm, OSA and ETS2 proteins.

According to a fourth particular aspect of an immunogenic product of the invention, wherein the carrier protein molecule induces, in addition to the differentiation of auxiliary T lymphocytes ("T helper"), the production of antibodies raised against the carrier protein molecule, said carrier protein molecule (ii) is selected amongst Bet v 1, Der p 1 and Fel d 1 proteins.

In an immunogenic product according to the invention, the immunogenic protein heterocomplexes are selected amongst the following heterocomplexes, where the antigenic proteins (i), on the one hand, and the protein carrier molecule (ii), on the other hand, are respectively:

a) (i) IL-4 and (ii) KLH;
b) (i) alpha interferon and (ii) KLH;
c) (i) VEGF and (ii) KLH;
d) (i) IL-10 and (ii) KLH;
e) (i) alpha interferon and (ii) gp 160 of VIH1;
f) (i) IL-4 and (ii) the Bet v 1 allergenic antigen; and
g) (i) VEGF and (ii) the papillomavirus E7 protein;
h) (i) the inactivated VIH1 Tat protein and (ii) the VIH1 gp120 protein;
i) i) an IgE isotype human antibody and (ii) the inactivated VIH1 Tat;
j) (i) the ricin β fragment and (ii) KLH.

Method for Preparing an Immunogenic Product Comprising Immunogenic Protein Heterocomplexes of the Invention Another object of the invention is also a method for preparing an immunogenic product comprising the hereinabove defined immunogenic heterocomplexes, characterized in that it comprises the following steps of:

a) incubating the antigenic proteins (i) and the carrier molecule (ii) in a molar ratio (i):(ii) ranging from 10:1 to 50:1 in the presence of a binding chemical agent;

b) collecting the immunogenic product comprising immunogenic heterocomplexes being prepared in step a).

Preferably, the binding chemical agent is glutaraldehyde.

Most preferably, the method is further characterized in that step a) is followed by a stabilizing step of the product comprising the immunogenic heterocomplexes by formaldehyde, prior to step b) for recovering the heterocomplexes.

Preferably, when glutaraldehyde is used as the binding chemical agent, it is present in the coupling reaction medium in a final concentration ranging between 0.002M and 0.03M, advantageously between 0.02M and 0.03M, preferably in a final concentration of 0.026M.

The coupling reaction with glutaraldehyde advantageously occurs for 20 minutes to 60 minutes, preferably 30 minutes, at a temperature ranging from 20 to 25° C.

After the coupling step, the excess glutaraldehyde is removed, for example, through dialysis by means of a dialysis membrane with a 3 kDa cutoff threshold. The dialysis step advantageously occurs at 4° C. in a buffer adjusted to pH 7.6.

For stabilizing the product comprising the protein heterocomplexes as prepared in step a), said product could be treated in solution by the formaldehyde, for example, by formaldehyde in a final concentration of 3 mM. The stabilization reaction is advantageously performed for 12 to 48 hours, preferably between 20 and 30 hours, and most preferably, for 24 hours. The stabilization reaction using the formaldehyde is advantageously stopped through the addition of glycine, preferably in a 0.1M concentration, for 1 hour and at a temperature ranging from 20 to 25° C.

Most preferred method for preparing a stable immunogenic product comprising immunogenic protein heterocomplexes comprising TNFa and a carrier protein.

The inventors have found that the general method disclosed above in the present specification, when applied to heterocomplexes comprising TNFa and a carrier protein, should be carried out according to the most preferred embodiments that are detailed hereunder.

Thus, a further object of the present invention consists of a method for preparing a stable immunogenic product comprising antigenic heterocomplexes of TNFa and a carrier protein, comprising the steps of:

a) providing a liquid solution containing TNFa;

b) adding one or more antioxidant compounds to said liquid solution containing TNFa of step a);

c) adding a carrier protein to the liquid solution obtained at the end of step b), so as to obtain a liquid mixture of TNFa and said carrier protein;

d) adding glutaraldehyde to the liquid mixture obtained at the end of step c), so as to partially covalently conjugate TNFa molecules to said carrier protein and obtain heterocomplexes between TNFa and said carrier protein;

e) removing glutaraldehyde and free molecules of both TNFa and said carrier protein from the solution obtained at the end of step d), so as to obtain a liquid solution containing purified heterocomplexes between TNFa and said carrier protein;

f) adding formaldehyde to the liquid solution obtained at the end of step e), and maintaining the presence of formaldehyde for a period of time ranging from 48 hours to 240 hours;

g) adding glycine to the heterocomplexes between TNFa and said carrier protein obtained at the end of step f), and h) removing formaldehyde and glycine from the liquid solution obtained at the end of step g), so as to obtain a liquid solution containing stabilized heterocomplexes between TNFa and said carrier protein; and By performing the method described above, the resulting stable immunogenic products are endowed with increased ability to induce the production of antibodies that neutralize native TNFa, when administered to a mammal in combination with one or more immunoadjuvant compounds.

Thanks to the combined steps of the method according to the invention, the final stable immunogenic product is obtained with a high reproducibility.

Notably, it has been found that the immunogenic activity of the stable immunogenic products prepared by performing the method according to the invention was very reproducible, from one preparation batch to another.

As shown in the examples 37-40 herein, the stable immunogenic products prepared by performing the most preferred method above are devoid of detectable TNFa biological activity, both in vitro and in vivo, since the LD50 dose is greater than 400 ng/ml, as expressed in TNFa concentration.

Also, it is shown herein that beyond the induction of high anti-TNFa antibody titers, the stable immunogenic products prepared by performing the most preferred method above induce the production of highly neutralizing anti-TNFa antibodies having a neutralizing capacity NC50 of more than 1/1000.

Further, it has also been shown that the stable immunogenic products prepared by performing the most preferred method above can be safely administered to mammals, since these products do not induce any adverse side effect, and particularly no inflammation nor any alteration of the organs such as heart, lungs, liver and spleen even when administered in an amount of 4000 times the Single Human Therapeutic Dose (SHTD).

Additionally, the stable immunogenic products prepared by performing the most preferred method above induce a strong production of anti-TNFa neutralizing antibodies, specifically of the IgG isotype, in Rhesus macaques, which shows that these stable immunogenic products are able to break immunological tolerance for endogenously produced proteins and induce an effective vaccination leading to neutralization of TNFa, which vaccination is able to prevent deleterious effects of over-production of TNFa in all pathological situations wherein TNFa is involved.

It has been further shown that the stable immunogenic products prepared by performing the most preferred method above are able to effectively vaccinate mammals against TNFa-induced arthritis. Still further, it has been shown that these stable immunogenic products are able to prevent and/or treat TNFa-induced arthritis when used alone, with no need to complement the preventive or curative treatment with any additional anti-arthritis active ingredient, like methotrexate.

Without wishing to be bound by any particular theory, the applicant believes that the specific combination of steps a) to h) allows preserving the spatial conformation of the TNFa starting product while enhancing exposure of the important antigenic epitopes of TNFa to the solvent, so as to maximize an efficient presentation of the TNFa antigen to the immunocompetent cells, when it is administered to a mammal.

Without wishing to be bound by any particular theory, the applicant also believes that the specific combination of steps a) to h) allows both a high structural and chemical stabilization of the final immunogenic product. Such specific features of the resulting stable immunogenic products obtained by the method should allow the preparation of vaccine compositions that are also very stable during a long time of storage.

Further, it has been found that the method of the invention allows the preparation of a final stable immunogenic product that is endowed with no residual biological activity of the TNFa starting product. Notably it has been found that the ED50 of the TNFa starting product was of about 10 pg/mL, whereas the final stable immunogenic product obtained by the method has an ED50 value of more than 50 ng/mL. In the same time, the final stable immunogenic product is endowed with a high immunogenicity.

At step a), TNFa consists of a native TNFa selected from the group consisting of mouse TNFa, rat TNFa, rabbit TNFa and human TNFa. Preferably, TNFa consists of human TNFa.

In certain embodiments of the method according to the invention, step b) comprises the following steps:

b1) adding one or more antioxidant compounds to said liquid solution containing TNFa of step a); and b2) adding, to the liquid solution obtained at the end of step b1); one or more compounds that induce exposition to the solvent of the hydrophobic portions of TNFa;

It has been found according to the invention that adding one or more antioxidant compounds, at step b) or at step b1), reduces loss of immunogenicity of TNFa.

Preferably, at step b), or at step b1) depending of the embodiment of the method, the antioxidant compounds are selected from the group consisting of EDTA, acetyl cysteine, ascorbic acid, ascorbyl glucoside, calcium ascorbate, sodium ascorbate, disodium ascorbyl sulfate, magnesium ascorbate, magnesium ascorbyl phosphate, caffeic acid, and cysteine.

In certain embodiments of the method, step d) comprises the following steps:

d1) adding glutaraldehyde to the liquid mixture obtained at the end of step c), so as to partially covalently conjugate TNFa molecules to said carrier protein and obtain heterocomplexes between TNFa and said carrier protein; and d2) adding one or more antioxidant compounds to the heterocomplexes between TNFa and said carrier protein obtained at the end of step d1);

The antioxidant compounds used at step d2) are preferably the same as those used in step b), or step b1).

At step h), formaldehyde and glycine are removed from the solution obtained at the end of step g), so as to obtain a purified stable immunogenic product comprising heterocomplexes between TNFa and said carrier protein.

At the end of step h), the stable immunogenic product is obtained under the form of a translucent colorless liquid solution that is practically free of any visible particles.

In certain embodiments, said method may also comprise a further step i) of freezing the solution obtained at the end of step h).

In certain other embodiments, said method may also comprise a further step i) of lyophilizating the solution obtained at the end of step h), so as to obtain a white powder that can be stored for a long period of time before use.

In preferred embodiments of step a), TNFa concentration ranges from 0.1 mg/mL to 50 mg/mL, and even more preferably ranges from 0.5 mg/mL to 10 mg/mL.

In preferred embodiments of step b), when the antioxidant compound consists of EDTA, final EDTA concentration ranges from 1 mM to 10 mM.

Advantageously, EDTA is added as a buffer solution having a pH ranging from 7 to 8.5, more preferably from 7.5 to 8.1.

At step b2) the one or more compounds that induce exposition to the solvent of the hydrophobic portions of TNFa is most preferably DMSO.

In preferred embodiments of step b2), when the compound that induces exposition to the solvent of the hydrophobic portions of TNFa consists of DMSO, then final DMSO concentration ranges from 5% v/v to 20% v/v.

Advantageously, step b2) is carried out for a period of time ranging from 10 min to 50 min, more preferably from 20 min to 40 min.

In preferred embodiments of step c), the molar ratio of TNFa to said carrier protein ranges from 5:1 to 100:1, and even more preferably ranges from 20:1 to 80:1. In the most preferred embodiments of step c), the molar ratio of TNFa to said carrier protein ranges from 30:1 to 70:1.

In preferred embodiments of step d), final glutaraldehyde concentration ranges from 0.05% w/w to 0.5% w/w.

Advantageously, step d2) is carried out for a period of time ranging from 30 min to 60 min, more preferably from 40 min to 50 min.

In preferred embodiments of step d2), when the antioxidant compound consists of EDTA, then final EDTA concentration ranges from 1 mM to 10 mM.

In preferred embodiments of step e), glutaraldehyde is removed by performing a dialysis or by performing an ultrafiltration with diafiltration, or by performing Tangential Flow Filtration (TFF), as shown in the examples herein.

When dialysis is performed, a dialysis membrane with a cut-off threshold of 6 to 8 KDa is preferably used.

In certain embodiments, the dialysis step comprises one or more sub-steps, typically three sub-steps. Preferably, dialysis comprises two identical sub-steps performed with the working buffer (100 mM phosphate, 150 mM NaCl at pH 7.8, EDTA mM), which are followed by the third sub-step performed with PBS buffer.

Usually, the dialysis step is performed with a conventional buffer solution, such as a Phosphate Buffer Saline solution (PBS), against 200 to 400 times the volume of the liquid solution containing the heterocomplexes between TNFa and the carrier protein, wherein the TNFa are partly covalently conjugated to the carrier protein which is used.

When ultrafiltration with diafiltration is performed, a filtering membrane with a cut-off threshold of 10 000 Kda is preferably used, it being understood that the heterocomplexes between TNFa and the carrier protein are found in the ultrafiltration retentate. Usually, the liquid used for diafiltration consists of a buffer solution, such as a Phosphate Buffer Saline solution (PBS). Usually, the diafiltration is performed three times with an equal volume of said buffer solution.

In preferred embodiments of step f), the final concentration of formaldehyde ranges from 1% w/w to 10% w/w, and even more preferably ranges from 2% w/w to 5% w/w.

In further preferred embodiments of step f), the presence of formaldehyde is maintained during a period of time ranging from 96 hours to 192 hours.

It has been found according to the invention that maintaining the presence of formaldehyde with the heterocomplexes for a time period of less than 96 hours led to a final immunogenic compound that was significantly less stable with time, when compared with a stable immunogenic compound obtained according to the preferred embodiments of the method according to the invention.

On the other hand, it has been found according to the invention that maintaining the presence of formaldehyde with the heterocomplexes for a time period of more than 192 hours led to a final immunogenic compound that was highly stable but with a significantly lowered ability to induce antibodies having a high neutralizing activity against native TNFa.

More preferably, at step f), the presence of formaldehyde is maintained during a period of time ranging from 120 hours to 168 hours.

Most preferably, at step f), the presence of formaldehyde is maintained during a period of time ranging from 130 hours to 150 hours.

In preferred embodiments of step g), formaldehyde is removed by performing a dialysis or by performing an ultrafiltration with diafiltration.

Advantageously, step f) is carried out at a temperature ranging from 30° C. to 42° C., more preferably from 35° C. to 39° C.

The conditions for dialysis or ultrafiltration with diafiltration that are used in step h) are usually the same as those previously defined for step e) above.

In preferred embodiments of step g), final glycine concentration ranges from 0.01 M to 10 M, and even more preferably ranges from 0.05 M to 2 M.

Advantageously, when carrying out step g) the pH of the liquid solution is adjusted to a pH ranging from 6.8 to 7.8, more preferably from 7.0 to 7.6, for example by using a base such as NaOH.

In preferred embodiments of step h), formaldehyde and glycine are removed by performing a dialysis or by performing an ultrafiltration with diafiltration.

The conditions for dialysis or ultrafiltration with diafiltration that are used in step h) are usually the same as those previously defined for step e) above.

At step h), formaldehyde and glycine may be removed by performing a step of dialysis, a step of ultrafiltration with dispersion or a step of tangential Flow Filtration (TFF), as shown in the examples herein.

According to the method of the invention, a wide diversity of carrier proteins known to the one skilled in the art may be used at step c). The carrier protein should bear sufficient helper T-cell epitopes so as to activate T-helper and B cells and induce these cells to release enough IL-1 and IL-2 to induce the expansion of the B cell clones that will produce the neutralizing anti-TNFa antibodies.

A "carrier protein molecule", included in the stable immunogenic product of the invention, means any protein or peptide being at least 15 amino acids long, whatever its amino acid sequence, and which, when partially covalently being associated to the molecules of TNF a for forming protein heterocomplexes making up the immunogenic product of the invention, allows for a large number of molecules of TNFa to be presented to the B lymphocytes.

According to a first aspect, the carrier protein molecule consists of one protein or one peptide being at least 15 amino acid long, or also an oligomer of such a peptide, comprising one or more auxiliary T epitopes ("helper") able to activate auxiliary T lymphocytes ("T helper") of the host organism for producing cytokines, including interleukin 2, such cytokins, in turn, activating and inducing the proliferation of B lymphocytes, which, after maturation, will produce antibodies raised against the antigenic protein (i).

According to a second aspect, a carrier protein molecule consists of one protein or one peptide being at least 15 amino acid long, or also an oligomer of such a peptide, comprising besides one or more auxiliary T epitopes ("helper"), as described in the above-mentioned first aspect, one or more cytotoxic T epitopes, able to induce a cell immune response through the production of cytotoxic T lymphocytes specific of the carrier protein molecule, such lymphocytes being able to specifically recognize cells expressing on their surface said carrier protein or any peptide being derived therefrom, in association with class 1 Histocompatibility Major Complex (HMC) molecules. If need be, the carrier protein molecule consists in one oligomer of one protein or one peptide, further comprising besides one or more T helper epitopes, one or more above defined cytotoxic T epitopes.

According to a third aspect, a carrier protein molecule consists in one protein or one peptide being at least 15 amino acid long, as well as one oligomer of such a peptide, comprising besides one or more auxiliary T epitopes ("helper") as defined in the first aspect, one or more B epitopes, able to induce the production of antibodies by lymphocytes raised against the carrier protein.

In some embodiments, the carrier protein, besides its T helper, used for activating an antibody response against the antigen of interest, could also activate a cytotoxic response against cells carrier peptides of the carrier and/or stimulate an antibody response against such a carrier protein molecule.

The carrier protein molecule could also consist in a homo-oligomer or a homo-polymer of the native protein, from which it is derived, as well as a homo-oligomer or a homo-polymer of a peptide fragment of the native protein, from which it is derived. The antigenic protein of interest could also consist in a hetero-oligomer or a hetero-polymer comprising a combination of several distinct peptide fragments initially included in the native protein from which it is derived.

Examples of protein carriers which may be used when performing the method according to the invention include the Diphtheria and Tetanus toxoids (DT, DT CRM197, other DT mutants, e.g. position Glu-148, etc. [see, e.g., U.S. Pat. No. 4,709,017, WO93/25210, WO95/33481, etc.] and TT (and TT fragment C) respectively), Keyhole Limpet Haemocyanin (KLH), OMPC from *N. meningitidis*, and the purified protein derivative of Tuberculin (PPD).

The function of the carrier is to provide cytokine help in order to enhance the immune response against TNFa. A non-exhaustive list of carriers which may be used in the present invention include: Keyhole limpet Haemocyanin (KLH), serum albumins such as bovine serum albumin (BSA), inactivated bacterial toxins such as tetanus or diphtheria toxins (TT and DT), or recombinant fragments thereof (for example, Domain 1 of Fragment C of TT, or the translocation domain of DT), or the purified protein derivative of tuberculin (PPD).

In an embodiment of the method, the carrier is Protein D from *Haemophilus influenzae* (EP 0 594 610 B1). Protein D is an IgD-binding protein from *Haemophilus influenzae* and has been patented by Forsgren (WO 91/18926, granted EP 0 594 610 B1). In some circumstances, for example in recombinant immunogen expression systems it may be desirable to use fragments of protein D, for example Protein D ⅓.sup.rd (comprising the N-terminal 100-110 amino acids of protein D (WO 99/10375; WO 00/50077)).

Thus, in preferred embodiments of the method, said carrier protein is selected form the group consisting of diphtheria toxoid (DT) and mutants thereof, Tetanus toxoid (TT), Keyhole Limpet Haemocyanin (KLH), and the purified protein derivative of Tuberculin (PPD), OMPC from *N. meningitidis*, the purified protein derivative of Tuberculin (PPD), bovine serumalbumin (BSA) and Protein D from *Haemophilus influenzae.*

Most preferably, said carrier protein consists of Keyhole Limpet Haemocyanin (KLH).

The present invention also relates to a method for preparing a vaccine composition comprising the steps of:

a) preparing a stable immunogenic product comprising antigenic heterocomplexes of TNFa by performing the method of any one of claims 1 to 22; and b) combining said stable immunogenic product comprising antigenic heterocomplexes of TNFa prepared at step a) with one or more immunoadjuvants.

This invention also pertains to a stable immunogenic product comprising antigenic heterocomplexes of TNFa and a carrier protein which has one or more of the following technical features:

i) it possesses a molecular weight ranging from 50 kDa to 8 Mda, with about 30% of the total protein amount having a molecular weight lower than 1 MDa;

ii) it exhibits a molar ratio of TNFa to said carrier protein ranging from 40:1 to 60:1;

iii) it induces the production of anti-TNFa antibodies having a TNFa neutralizing capacity (NC50) of more than 1/1000.

By way of illustration, it has been shown according to the invention, using the first or the second above described quantification methods that: in the immunogenic product comprising heterocomplexes between the KLH carrier molecule and human TNFa molecules, less than 40% of the TNFa molecules are covalently linked to the KLH carrier protein molecule.

The Compositions Comprising an Immunogenic Product Comprising Immunogenic Protein Heterocomplexes of the Invention Another object of the present invention is also to provide a composition comprising an immunogenic product such as hereinabove defined.

The invention also relates to a pharmaceutical composition comprising a protein immunogenic product such as hereinabove defined.

Another object of the invention is an immunogenic composition characterized in that it comprises, as the active ingredient, an immunogenic product as hereinabove defined, in association with one or more physiologically compatible excipients.

It also relates to a vaccine composition characterized in that it comprises, as the active ingredient, an immunogenic product as hereinabove defined, in association with one or more physiologically compatible excipients.

Depending on the target objectives, systemic adjuvants or mucosal adjuvants are being used. For example, a mucosal adjuvant is preferably used for preventing the epithelial tissue cancers and preferably systemic adjuvants are used for preventing or treating virus infections such as HIV1 and HTLV1 as well as for preventing or treating allergies.

Amongst systemic adjuvants, those of the IFA type are preferably used (Incomplete Freund's Adjuvant), as well as calcium phosphate or alumina hydroxide.

Amongst mucosal adjuvants, those preferably used are like B chloratoxin (CTB) or a mutant of the LT toxin (LTμ).

According to a particular aspect, an immunogenic composition according to the invention also comprises one or more immuno-stimulating agents, in combination with an immunity adjuvant, such as for example, the CpG immuno-stimulating agent well known in the state of the art.

It has indeed been shown according to the invention that the use of the CpG adjuvant, and more particularly the CpG adjuvant wherein the intra-chain bonds between nucleotides consist in phosphorothioate bonds to stimulate the simultaneous production of IgG and IgA isotype antibodies, after a systemic administration.

It also relates to a mucosal or systemic vaccine, characterized in that it comprises, as the active ingredient, an immunogenic product such as hereinabove defined, in association with one or more excipients, including physiologically compatible adjuvants.

The immunogenic compositions or the vaccines according to the present invention are useful for example in the treatment, both curative and preventive, of cancers, more particularly, of cancers induced by viruses such, as for example, the ATL (Acute T cell leukemia) caused by the HTLV1, or the neck of uterus cancer caused by the papillomavirus, as well as the Burkitt lymphoma as well as the Kaposi sarcoma caused by the viruses from the herpes family, respectively the Epstein-Barr (EBV) and the HHV8 as well as in treatment of AIDS or for preventing or treating allergic reactions.

The immunogenic products according to the invention could be used as follows.

To a patient, is administered, under a form adapted to the systemic or mucosal administration, an immunogenic product comprising immunogenic protein heterocomplexes according to the present invention, for example, intranasally, in a sufficient amount to be therapeutically efficient, to a subject in need of such a treatment. The dose to be administered could range for example from 10 to 1000 μg intranasally, once a week for 2 months and then, given the transitory character of the antibody response directed against the antigen of interest, periodically depending on the serum antibody rate, for example, once every 2 to 6 months.

Two or more different immunogenic products could be administered in one single preparation for inducing neutralizing antibodies in all the deleterious functional sites should one single molecule not carry all the active sites of the overproduced toxin or cytokin which is to be neutralized.

As for drugs, the immunogenic products of the invention could be incorporated into pharmaceutical compositions adapted for an administration through the systemic route or an administration through the mucosal route, including the oromucosal route, more particularly, the intranasal route, the oral route and the vaginal route. The administration could be performed in one single dose or a dose repeated once or several times after some time interval.

This is why the present application has also as an object a pharmaceutical, curative, or preventive composition, characterized in that it comprises as an active ingredient, one or more immunogenic products such as hereinabove defined. The immunogenic product could be packaged alone or mixed with an excipient or a mixture of pharmaceutically acceptable excipients such as an adjuvant. Amongst the excipients adapted for the intranasal or oral route, are particularly to be selected the capryl caproyl macrogol glycerides as Labrasol® from the GATTEFOSSE corporation or alumina hydroxide (Alhydragel, Superfos, Denmark).

For the oral administration according to the invention, the active ingredient will be associated to a mucosal immunity adjuvant, such as a CT, LT or CTB mutant.

Galenic forms are particularly well suited, as described by Boyaka et al. "Strategies for mucosal vaccine development" in Am. J. Trop. Med. Hyg. 60(4), 1999, pages 35-45. Are also to be mentioned gastro resistant, more particularly bioadhesive microgranules, such as described by Rojas et al. in Pharmaceutical Research, vol. 16, no 2, 1999, page 255.

Under the particular implementing conditions, an abovementioned vaccine pharmaceutical composition will be selected, characterized in that it comprises a mucosal immunity adjuvant, such a CT mutant (cholera toxin) or a LT mutant E. coli labile enterotoxin).

Under other particular implementing conditions, a vaccine pharmaceutical composition will be selected, characterized in that it contains an adjuvant absorbing the active ingredient, such as alumina hydroxide or gold particles.

Another object of the present invention is a method for preparing a composition as described hereinabove, characterized in that are mixed, using methods known per se, the active immunogenic product(s) with the acceptable excipients, including pharmaceutical acceptable ones and if need be, with a systemic or mucosal immunity adjuvant.

Under preferred implementing conditions of the abovementioned method, bioadhesive and gastroresistant microgranules are prepared for the digestive route containing the immunogenic active ingredients and, if need be, the adjuvants.

Most Preferred Embodiments of a Vaccine Composition According to the Invention.

To prepare the vaccine composition above, the stable immunogenic product obtained by the method according to the invention is adjusted to an appropriate concentration, optionally combined with a suitable vaccine adjuvant, and packaged for use.

As used herein, the term "adjuvant" refers to its ordinary meaning of any substance that enhances the immune response to an antigen with which it is mixed. Adjuvants useful in the present invention include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (*Bacillus* Calmette-Guerin) and *Corynebacterium parvum* are potentially useful adjuvants Any adjuvant known in the art may be used in the vaccine composition above, including oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), Biostim™ (e.g., 01K2), the "Iscoms" of EP 109 942, EP 180 564 and EP 231 039, aluminum hydroxide, saponin, DEAE-dextran, neutral oils (such as miglyol), vegetable oils (such as arachis oil), liposomes, Pluronic.RTM. polyols, the Ribi adjuvant system (see, for example GB-A-2 189 141), or interleukins, particularly those that stimulate cell mediated immunity. An alternative adjuvant consisting of extracts of *Amycolata*, a bacterial genus in the order Actinomycetales, has been described in U.S. Pat. No. 4,877,612. Additionally, proprietary adjuvant mixtures are commercially available. The adjuvant used will depend, in part, on the recipient organism. The amount of adjuvant to administer will depend on the type and size of animal. Optimal dosages may be readily determined by routine methods.

Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polyanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," Sem. Hematol., 30:3-15 (1993).

The adjuvant properties of saponin have been long known, as has its ability to increase antibody titres to immunogens. As used herein, the term "saponin" refers to a group of surface-active glycosides of plant origin composed of a hydrophilic region (usually several sugar chains) in association with a hydrophobic region of either steroid or triterpenoid structure. Although saponin is available from a number of diverse sources, saponins with useful adjuvant activity have been derived from the South American tree Quillaja saponaria (Molina). Saponin from this source was used to isolate a "homogeneous" fraction denoted "Quil A" (Dalsgaard, K., (1974), Arch. Gesamte Virusforsch. 44:243).

Dose-site reactivity is a major concern for both the veterinary and human use of Quil A in vaccine preparations. One way to avoid this toxicity of Quil A is the use of an immunostimulating complex (known as an ISCOM™, an abbreviation for Immuno Stimulating COMplex). This is primarily because Quil A is less reactive when incorporated into immunostimulating complexes, because its association with cholesterol in the complex reduces its ability to bind to cholesterol in cell membranes and hence its cell lytic effects. In addition, a lesser amount of Quil A is required to generate a similar level of adjuvant effect.

The immunomodulatory properties of the Quil A saponins and the additional benefits to be derived from these saponins when they are incorporated into an immunostimulating complex have been described in various publications, e.g. Cox and Cox, J. C. and Coulter, A. R. Advances in Adjuvant Technology and Application in Animal Parasite Control Utilising Biotechnology, Chapter 4, Editor Yong, W. K. CRC Press (1992); Cox, J. C. and Coulter, A. R. (1997) Vaccine, 15(3):248-256; Cox, J. C. and Coulter, A. R. (1999) BioDrugs 12(6):439-453; Dalsgaard, (1974) (supra); Morein et al., (1989) "Immunostimulating complex (ISCOM)", In "Vaccines: Recent Trends and Progress". G. Gregoriadis, A. C. Allison and G. Poster (Eds). Plenum Press, New York, p. 153; Australian Patent Specifications Nos. 558258, 589915, 590904 and 632067.

Classic ISCOMs are formed by combination of cholesterol, saponin, phospholipid, and immunogens, such as viral envelope proteins. ISCOM matrix compositions (known as ISCOMATRIX™) are formed identically, but without viral proteins. ISCOMs appear to stimulate both humoral and cellular immune responses. ISCOMs have been made with proteins from various viruses, including HSV-1, CMV, EBV, hepatitis B virus (HBV), rabies virus, and influenza virus see for example, I. G. Barr et al., Adv. Drug Delivery Reviews, 32:247-271 (1998). It has been observed that where naked DNA or polypeptides from infectious agents are poorly immunogenic when given by themselves, inclusion within ISCOMs has increased their immunogenicity. Various proteins formulated with ISCOMs have been shown to induce CTL, mainly in rodent models. Berzofsky, (1991), Biotechnol. Ther. 2:123-135; Hsu et al., (1996), Vaccine 14:1159-1166; Lipford et al., (1994), Vaccine 12:73-80; Mowat et al., (1991), Immunology 72:317-322; Osterhaus et al., (1998), Dev. Biol. Stand. 92:49-58; Rimmelzwaan et al., (1997), J. Gen. Virol. 78 (pt. 4):757-765; Sambhara et al., (1998), J. Infect. Dis. 177:1266-1274; Sambhara et al., (1997), Mech. Aging Dev. 96:157-169; Sjolander et al., (1997), Vaccine 15:1030-1038; Sjolander et al., (1998), J. Leukoc. Biol. 64:713-723; Takahashi et al., (1990), Nature 344:873-875; Tarpey et al., (1996), Vaccine 14:230-236; Trudel et al., (1987), Vaccine 10: 107-112; Verschoor et al., (1999), J. Virol. 73:3292-3300; Villacres-Eriksson, (1995), Clin. Exp. Immunol. 102:46-52; Zugel et al., (1995), Eur. J. Immunoll. 25:451-458.

Association between a stable immunogenic product obtained by the method of the invention and an adjuvant is thought to be important for optimal induction of immune responses. A number of studies have been done which confirm this hypothesis including work with virosomes and ISCOMs™ (Ennis, F. A., Crux, J., Jameson, J., Klein, M., Burt, D. and Thipphawong, J. 1999. Virology 259: 256-261, Zurbriggen, R., Novak-Hofer, I., Seelig, A. and Gluck, R. (2000), Progress in lipid Research 39: 3-18, Voeten, J. T. M., Nieuwkoop, N. J., Lovgren-Bengtsson, K., Osterhaus, D. M. E. and Rimmelzwaan, G. F. 2000. Euro J 1 mm (Submitted)). Typically association between ISCOM™ and antigen has been achieved by incorporation of amphipathic antigens into the ISCOM™ structure during formation (Morein, B., B. Sundquist, S. Hoglund, K. Dalsgaard, and A. Osterhaus. 1984. Nature 308:457). Incorporation was by hydrophobic interactions. More recently methods to associate antigens with a preformed protein-free immunostimulating complex (ISCOMATRIX™) utilizing chelating and electrostatic interactions have been developed (International Patent Applications Nos. PCT/AU98/00080-WO 98/36772, and PCT/AU00/00110).

In certain embodiments of a vaccine composition according to the invention, said vaccine composition comprises, as pharmaceutical excipients, one or more charged inorganic carriers. Examples of charged organic carriers which are adjuvants suitable for use in the present invention include, but are not limited to, saponin, saponin complexes, any one or more components of the immunostimulating complex of saponin, cholesterol and lipid known as ISCOMATRIX™ (for example the saponin component and/or the phospholipid component), liposomes or oil-in-water emulsions. (The composition and preparation of ISCOMATRIX™ is described in detail in International Patent Application Number PCT/SE86/00480, Australian Patent Numbers 558258 and 632067 and European Patent Publication No. 0 180 564, the disclosures of which are incorporated herein by reference). Further examples of adjuvants include, but are not limited to, those detailed in the publications of Cox and Coulter, 1992, 1997 and 1999. It should be understood that the subject organic carrier may be naturally occurring or it may be synthetically or recombinantly derived.

The vaccine compositions may also include further adjuvants to enhance effectiveness of the composition. Suitable adjuvants include, but are not limited to: (1) aluminum salts (alum), such as aluminum hydroxide, aluminum phosphate, aluminum. sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles, (b) SAF, containing 10% Squalene, 0.4% Tween 80, 5% pluronic-blocked polymer, and thr-MDP (see below) either microfluidized into a submicron emulsion or vortexed to generate a large particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.); (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12, etc), interferons (e.g. gamma interferon), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63, LT-R72, CT-S109, PT-K9/G129; see, e.g. WO 93/13302 and WO 92/19265; (7) other substances that act as immunostimulating agents to enhance the effectiveness of the composition; and (8) microparticles with adsorbed macromolecules, as described in International Patent Application No. PCT/US99/17308. Alum and MF59 are preferred.

As mentioned above, suitable muramyl peptides include, but are not limited to, N-acetyl-muramyl-L-threonyl-D-isoglutamine (thr-MDP), N-acetyl-normauramyl-L-alanyl-D-isoglutamine (nor-MDP), N-acetylmuramyl-L-alanyl-D-isoglutaminyl-L-alanine-2-(1'-2'-dipalmitoyl-s-n-glycero-3-hydroxyphosphoryloxy)-ethylamine (MTP-PE), etc.

Further adjuvants for inducing a mucosal or a systemic response against an immunogenic compound according to the invention may be those that are described in the book of Vogel et al. (Vogel F. R., Powell M. F. and Alving C. R., "A compendium of vaccine adjuvants and excipients"; $2^{nd}$ Edition; Vogel F. R. and Powell M F, 1995, "A summary compendium of vaccine adjuvants and excipients. In: Powell M F, Newman M J eds. "Vaccine design: the subunit and adjuvant approach". New York: Plenum publishing, 1995: 141-228).)

Generally, adjuvants that may be comprised in a vaccine composition according to the invention encompass, without being limited to:

(i) Gel-type adjuvants, such as aluminum hydroxide or aluminum phosphate (Glenny A T et al., 1926; J Pathol Bacteriol; Vol. 29: 38-45; Gupta R K and Siber G R, 1994; Biologicals; Vol. 22: 53-63);

(ii) Microbial adjuvants, such as:

DNA CpG motifs (Chu R S et al., 199; J Exp Med; Vol. 186: 1623-1631); Monophosphoryl lipid A (Schneerson R et al., 1991; J Immunol; Vol. 147: 2136-2140); Cholera toxin (Holmgren J et al., 1993; Vaccine; Vol. 11: 1179-1184; Okahashi N et al., 1996; Infect Immun; Vol. 64: 1516-1525);

*E. coli* heat-labile toxin (Lycke N et al., 1992; Eur J Immunol; Vol. 22: 2277-2281; de Haan L et al., 1996; Vaccine; Vol. 14: 260-266; Chong C et al., 1998. Vaccine; Vol. 16: 732-740);

Pertussis toxin (Roberts M et al., 1995; Infect Immun; Vol. 63: 2100-2108; Mu H H and Sewell W A, 1994; Immunology; Vol. 83: 639-645);

Muramyl dipeptide (Ellouz F et al.; 1974; Biochem Biophys Res Commun; Vol. 59: 1317-1325); Cohen L Y et al., 1996; Cell Immunol; Vol. 169: 75-84);

(iii) Oil-emulsion and emulsifier-based adjuvants, such as:

Freund's incomplete adjuvant (Dhiman N et al., 1997; Med Microbiol Immunol (Berlin); Vol. 186: 45-51; Putkonen P et al., 1994; J Med Primatol; Vol. 23: 89-94);

MF59 (Dupuis M et al., 1998; Cell Immunol; Vol. 186: 18-27; Kahn J O et al., 1994; J infect Dis; Vol. 170: 1288-1291; Ott G et al., 1995; Vaccine. Vol. 13: 1557-1562);

SAF (Allison A C; 1998; Dev Biol Stand; Vol. 92: 3-11; Gupta R K et al., 1993; Vaccine; Vol. 11: 293-306; Byars N E et al., 1994; Vaccine; Vol. 12: 200-209);

(iv) Particulate adjuvants, such as:

Immunostimulatory Complexes (ISCOMs) (Putkonen P et al., 1994; J Med Primatol; Vol. 23: 89-94; Gupta R K et al., 1993; Vaccine; Vol. 11: 293-306; Sjolander A et al., 1997; Cell Immunol; Vol. 177: 69-76);

liposomes (Richards R L et al., 1998; Infect Immun; Vol. 66: 2859-2865; Fernandes I et al., 1997; Mol Immunol; Vol. 34: 569-576);

biodegradable microspheres (Men Y et al., 1996; Vaccine; Vol. 14: 1442-1450; Shahin R et al., 1995; Infect Immun; Vol. 63: 1195-1200;

saponins (QS-21) (Newman M J et al., 1992; J Immunol; Vol. 148: 2357-2362; Neuzil K M et al., 1997; Vaccine. Vol. 15: 525-532);

(v) Synthetic adjuvants, such as:

nonionic block copolymers (Hunter R L et al., 1994; AIDS Res Hum Retroviruses; Vol. 10 (Suppl 2); S95-S98; Newman M J et al., 1997; Mech Ageing dev; Vol. 93: 189-203);

muramyl peptide analogues (Cohen L Y et al., 1996; Cell Immunol; Vol. 169: 75-84; Fast D J and Vosika G J, 1997; Vaccine; Vol. 15: 1748-1752; Bahr G M et al., 1995; Int J Immunopharmacol; Vol. 17: 117-131);

polyphosphazene (Payne L G et al., 1998; Vaccine; Vol. 16: 92-98);

synthetic polynucleotides (Johnson A G, 1994; Clin Microbiol Rev; Vol. 7: 277-289; Harrington D G et al., 1979; Infect Immun; Vol. 24: 160-166); and (vi) cytokines, such as:

IFN-g (Odean M J et al., 1990; Infect Immun; Vol. 58: 427-432);

Interleukin-2 (Nunberg J et al., 1989; Proc Natl Acad Sci USA; Vol. 86: 4240-4243);

Interleukin-12 (Luis C et al., 1994; Science; Vol. 263: 235-237; Bliss J et al., 1996; J Immunol; Vol. 156: 887-894; Jankovic D et al., 1997, J Immunol; Vol. 159: 2409-2417).

A further aspect of the present invention therefore relates to the use of a stable immunogenic product or of a vaccine composition as defined above to induce an immune response in a mammal including a humoral immune response wherein antibodies that neutralize the immunosuppressive, apoptotic or angiogenic properties of the native cytokine.

A further object of the invention consists of a method for inducing the production of antibodies that neutralize the activity of native TNFa in a mammal, comprising a step of administering to said mammal (i) a vaccine composition according to claim 23 or (ii) a stable immunogenic product comprising antigenic heterocomplexes of TNFa and a carrier protein according to claim 24 together with one or more immunoadjuvants.

The vaccine compositions optionally may include vaccine-compatible pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of *theobroma*.

A vaccine composition according to the invention may also further one or more pharmaceutically acceptable carriers and/or diluents, such carriers include any carrier that does not itself induce the production of a response harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art.

The vaccine compositions according to the invention may typically also contain diluents, such as water, saline, glycerol, ethanol, etc. Additionally, auxiliary substances, such as wetting or emulsifying agents, pH buffering substances, and the like, may be present in the compositions.

Suitable preparations of the vaccines of the present invention include injectables, either liquid solutions or suspensions. Solid forms suitable for solution in, or suspension in, a liquid pharmaceutically acceptable carrier prior to injection may also be prepared. The vaccine preparation may be emulsified. Additional substances that can be included in a product for use in the present methods include, but are not limited to one or more preservatives such as disodium or tetrasodium salt of ethylenediaminetetracetic acid (EDTA), merthiolate, and the like.

The vaccine compositions optionally may include vaccine-compatible pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of *theobroma*.

The vaccine compositions can be packaged in forms convenient for delivery. The compositions can be enclosed within a capsule, caplet, sachet, cachet, gelatin, paper, or other container. These delivery forms are preferred when compatible with entry of the immunogenic composition into the recipient organism and, particularly, when the immunogenic composition is being delivered in unit dose form. The dosage units can be packaged, e.g., in tablets, capsules, suppositories or cachets.

The forms suitable for injectable use include sterile aqueous solutions (where water soluble) or dispersions and sterile powders for the extemporaneous preparation of sterile injectable solutions or dispersions. They must be stable under the conditions of manufacture and storage and must be preserved against the contaminating action of microorganisms such as bacteria and fungi. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active immunogenic compound according to the invention is suitably protected, it may be orally administered, for example, with an inert diluent or with an assimilable edible carrier, or it may be enclosed in hard or soft shell gelatin capsule, compressed into tablets, or incorporated directly with the food of the diet. For oral therapeutic administration, the active immunogenic compound according to the invention may be incorporated with excipients and used in the form of ingestible tablets, buccal tablets, troches, capsules, elixirs, suspensions, syrups, wafers, and the like. Such vaccine compositions and preparations should contain at least 1% by weight of active immunogenic compound. The percentage of the compositions and preparations may, of course, be varied and may conveniently be between about 5 to about 80% of the weight of the unit. The amount of active immunogenic compound in such therapeutically useful vaccine compositions is such that a suitable dosage will be obtained. Preferred vaccine compositions or preparations according to the present invention are prepared so that a dosage unit form contains between about 0.1 g and 2000 mg of active immunogenic compound.

A vaccine composition according to the invention suitable for oral administration may also be prepared under the form of a liquid solution, including a liquid aerosol formulation.

The liquid aerosol formulations contain the immunogenic product and a dispersing agent in a physiologically acceptable diluent. The dry powder aerosol formulations of the present invention consist of a finely divided solid form of the immunogenic product and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art. In a particular embodiment, the mass median dynamic diameter will be 5 micrometers or less in order to ensure that the drug particles reach the lung alveoli [Wearley, L. L., Crit. Rev. in Ther. Drug Carrier Systems 8:333 (1991)].

Systems of aerosol delivery, such as the pressurized metered dose inhaler and the dry powder inhaler are disclosed in Newman, S. P., (Aerosols and the Lung, Clarke, S. W. and Davia, D. editors, pp. 197-22) and can be used in connection with the present invention.

The vaccine compositions according to the invention may be administered to the subject to be immunized by any conventional method including, e.g., by oral, intravenous, intradermal, intramuscular, intramammary, intraperitoneal, or subcutaneous injection; by oral, transdermal, sublingual, intranasal, anal, or vaginal, delivery. The treatment may consist of a single dose or a plurality of doses over a period of time.

The present invention is further illustrated by the following examples.

EXAMPLES

Examples of Heterocomplex Preparations

Example 1

Preparation of Murine KLH-VEGF Heterocomplex 0.58 mg of KLH protein is dissolved in 0.5 ml of 10 mM phosphate buffer, pH 8.5. To this solution is added 1 mg of murine VEGF dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses, each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 24 hours. Then the reaction is blocked by the addition of final 0.1 M glycine for 1 hour at room temperature.

The mixture is finally dialyzed under the same conditions as the previously performed dialysis.

Example 2

Human KLH-VEGF Heterocomplex

Such a heterocomplex is the active ingredient of a vaccine able to mainly induce in the vaccine the production of antibodies neutralizing the human VEGF.

0.58 mg of KLH protein is dissolved in 0.5 ml of 10 mM phosphate buffer, pH 8.5. To this solution is added 1 mg of human VEGF dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses, each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 24 hours. Then the reaction is blocked by the addition of final 0.1M glycine for 1 hour at room temperature. The mixture is finally dialyzed under the same conditions as the previously performed dialysis.

Example 3

Preparation of Murine KLH-IL4 Heterocomplex 0.841 mg of KLH protein is dissolved in 0,8 ml of 10 mM phosphate buffer, pH 8.5. To this solution is added 1 mg of murine IL4 dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses, each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 24 hours. Then the reaction is blocked by the addition of final 0.1 M glycine for 1 hour at room temperature. The mixture is finally dialyzed under the same conditions as the previously performed dialysis.

Example 4

Preparation of a Human KLH-IL4 Heterocomplex

Such a heterocomplex is the active ingredient of a vaccine able to mainly induce in the vaccine the production of antibodies neutralizing the human IL4.

1 mg of KLH protein is dissolved in 1 ml of 10 mM phosphate buffer, pH 8.5. To this solution is added 1 mg of murine IL4 protein dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 24 hours. Then the reaction is blocked by the addition of final 0.1 M glycine for 1 hour at room temperature. The mixture is finally dialyzed under the same conditions as the previously performed dialysis.

Example 5

Preparation of a KLH-IFNα Complex

Such a conjugate is the active ingredient of a vaccine able to mainly induce in the vaccine the production of antibodies neutralizing the human IFNα.

0.625 mg of KLH protein is dissolved in 0,6 ml of 10 mM phosphate buffer, pH 8.5. To this solution is added 1 mg of human IFNα protein dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses, each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 48 hours. Then the reaction is blocked by the addition of final 0.1 M glycine for 1 hour at room temperature. The mixture is finally dialyzed under the same conditions as the previously performed dialysis.

Example 6

Preparation of a gp160-IFNa Complex

Such a heterocomplex is the active ingredient of a vaccine able to induce in the vaccine the production of antibodies neutralizing both the gp160 structure protein of the HIV-1 virus and the immunosuppressive IFNα cytokin protein. Moreover, such a heterocomplex should be able to induce a cell reaction (chemiokins, auxiliary T, CTL) raised against the infected cells expressing the gp160.

0.380 mg of gp160 protein is dissolved in 0,380 ml of 10 mM phosphate buffer, pH 8.5. To this solution is added 1 mg of human IFNα protein dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 48 hours. Then the reaction is blocked by the addition of final 0.1 M glycine for 1 hour at room temperature. The mixture is finally dialyzed under the same conditions as the previously performed dialysis.

Example 7

Preparation of a gp160-Toxoid Tat Heterocomplex (The Tat Protein is Biochemically Inactivated)

Such a heterocomplex is the active ingredient of a vaccine able to induce in the vaccine the production of antibodies neutralizing both the gp160 structure protein of the HIV-1 virus and the extracellular Tat protein of V1H-1. Moreover, such a complex should be able to induce a cell reaction (chemiokins, auxiliary T, CTL) raised against the infected cells expressing the gp160.

0.550 mg of gp120 protein is dissolved in 0.550 ml of 10 mM phosphate buffer, pH 8.5. To this solution is added 1 mg of toxoid Tat protein dissolved in 1 ml of the same buffer.

The thus obtained protein mixture is treated using glutaraldehyde in the final concentration of 0.026 M for 30 minutes at room temperature.

Then the reaction is blocked by the addition of final 0.1 M glycine for 1 hour at room temperature. The excess glycine is then removed by 3 successive 2 hour dialyses each performed in a dialysis tube with a 3 kDa cutoff threshold, at 4° C. against 200 ml of phosphate buffer, pH 7.6, 10 mM.

Example 8

Preparation of a gp160-GM Tat Heterocomplex (The Tat Protein is Genetically Inactivated)

Such a heterocomplex is the active ingredient of a vaccine able to induce in the vaccinee the production of antibodies neutralizing both the gp160 structure protein of the HIV-1 virus and the Tat protein regulating the VIH-1. Moreover, such a heterocomplex should be able to induce a cell reaction (chemokines, auxiliary T, CTL) raised against the infected cells expressing the gp160.

0.550 mg of gp160 protein is dissolved in 0.550 ml of 10 mM phosphate buffer, pH 8.5. To this solution is added 1 mg of GM Tat protein dissolved in 1 ml of the same buffer.

The thus obtained protein mixture is treated using glutaraldehyde in the final concentration of 0.026 M for 30 minutes at room temperature.

Then the reaction is blocked by the addition of final 0.1M glycine for 1 hour at room temperature. The excess glycine is then removed by 3 successive 2 hour dialyses each performed in a dialysis tube with a cutoff threshold being 3 kDa, at 4° C., against 200 ml of phosphate buffer, pH 7.6 10 mM.

Example 9

Preparation of Murine KLH-TNFa Heterocomplex

Such a conjugate is the active ingredient of a vaccine able to mainly induce in the vaccine the production of antibodies neutralizing the murine TNFα.

0.625 mg of KLH protein is dissolved in 0.6 ml of 10 mM borate buffer, pH 8.8, 150 mM NaCl. To this solution is added 1 mg of human IFNα protein dissolved in 1 ml of the same buffer.

The thus obtained protein mixture is treated using glutaraldehyde in the final concentration of 0.026 M for 45 minutes at room temperature.

The excess glutaraldehyde is then removed by 3 successive 4-hour dialyses each performed in a dialysis tube with a cutoff threshold being 3 kDa, at 4° C., against 200 ml of phosphate buffer, pH 7.6 10 mM 150 mM NaCl.

The mixture is then treated using formaldehyde at the final concentration of 33 mM for 48 hours. Then the reaction is blocked by the addition of final 0.1M glycine for 1 hour at room temperature. The mixture is finally dialyzed under the same conditions as the previously performed dialysis.

Example 10

Preparation of a Tat Peptide Heterocomplex (19-50)-$_h$IgE

The Tat peptide (19-50) brings auxiliary helper epitopes.
Sequence of the Tat peptide to be used:
Lys-Thr-Ala-Cys-Thr-Asn-Cys-Tyr-Cys-Lys-Lys-Cys-Cys-Phe-His-Cys-Gln-Val-Cys-Phe-Ile-Thr-Lys-Ala-Leu-Gly-Ile-Ser-Tyr-Gly-Arg-Lys Such a conjugate is the active ingredient of a vaccine able to mainly induce in the vaccine the formation of (human) anti-IgE antibodies.

0.1 mg of Tat peptide (19-50) ($4.06 \times 10^{-8}$ mole) are dissolved in 0.2 ml of 10 mM borate buffer, pH 8.5. To this solution is added 1 mg of human IgE ($6.6 \times 10^{-9}$ mole) dissolved in 1 ml of the same buffer.

The thus prepared mixture is then treated using formaldehyde at the final concentration of 0.026 M for 30 minutes at room temperature.

The excess glutaraldehyde is then removed by 2 successive 4 hour dialyses and a final 16 hour dialysis against a large volume of phosphate buffer, 10 mM, pH 7.4 containing 0.8% of NaCl (PBS), at 4° C., using a dialysis bag with a cutoff threshold being at 10 kDa. (IgE peptide ratio=50:1)

Example 11

Preparation of a Heterocomplex Against the Ricin Fragment

Such a heterocomplex is the active ingredient of a vaccine able to induce in the vaccine the formation of neutralizing antibodies directed against the fragment involved in the binding of the ricin molecule, thereby preventing it from exerting its toxic activity.

To 0.5 mg of KLH ($1.1 \times 10^{-3}$ mole) dissolved in 0.5 ml of 10 mM phosphate buffer, pH 8.2, is added 1 mg ($3.3 \times 10^{-8}$ mole) of a fragment of ricin dissolved in 1 ml of the same buffer. The thus prepared mixture is treated using formaldehyde at the final concentration of 0.026 M for 30 minutes at room temperature.

The excess glutaraldehyde is then removed by 2 successive 4 hour each dialyses and a 16-hour dialysis against a large volume of phosphate buffer, 10 mM, containing 0.8% of NaCl (PBS), using a dialysis bag with a cutoff threshold being 3 kDa. (KLH:Ricin-a ratio=1:30).

Examples of Biochemical Characterizations of Heterocomplexes

A. Material and Methods of Examples 12 to 23

The biochemical characterizations of heterocomplexes are performed by means of the following techniques:

1. Antigenicity Test

The study of antigenicity of a heterocomplex compared to the antigenicity of proteins making it up is performed by a conventional indirect ELISA. Such a technique allows for a protein to be quantitatively measured through the specific recognition of an antibody raised against an antigen. Such a test comprises depositing sample dilutions containing the sought protein in wells of a microtiter plate. A specific polyclonal antibody reacts with the immobilized protein. A second antibody, conjugated with horseradish peroxydase, specific to the first one is then added. The formed complex is revealed through incubation with OPD. The resulting yellow color is directly proportional to the amount of bound proteins. The absorbance (DO) of each well is measured by means of a microplate reader. The amount of protein present in the sample is then determined by means of a calibrating range.

2. Isoelectrofocusing in Agarose Gel Followed by a Western Blot

The isoelectrofocusing in agarose gel allows to separate molecules depending on their isoelectric point (Ip) under non denaturing conditions, allowing to study heterocomplexes without destroying the weak bonds existing within such complexes.

The isofocusing is followed by an emergence through a Western blot. After electrophoretic separation, the molecules are transferred on a nitrocellulose membrane through capillarity. Such molecules are then characterized by immunochemistry.

3. Measurement of the Percentage of Molecules of the Antigen of Interest Covalently Linked to the Carrier Protein Molecule (First Method)

Estimating the percentage of molecules of the antigen of interest covalently linked to carrier protein molecules in an immunogenic product occurs, for example, through molecular sieving on a column containing Superdex 200, under denaturing (8 M urea) and reducing (5% beta-mercaptoethanol) conditions.

The % of covalently linked molecules of the antigen of interest is deducted from the amount of antigen of interest (determined by a conventional indirect ELISA) present in the exclusion volume of the column. Indeed, the carrier protein molecule, such as KLH, having a molecular mass much higher than the highest fractionating limit of the column being used (200 kDa in this case), exists in the exclusion volume of such a column. Thus, under denaturing and reducing conditions, only the antigens of interest covalently linked to the carrier protein molecule exist in the exclusion volume.

4. Measurement of the Percentage of Molecules of the Antigen of Interest Covalently Linked to the Carrier Protein Molecule (Second Method)

The percentage of cytokin fixed on the carrier protein (KLH) was determined by a double sandwich ELISA, by means of a capture antibody specifically directed against the carrier protein.

100 µl of horse polyclonal antibodies raised against KLH (1 mg/ml) diluted in a 10 mM phosphate buffer, pH 7.3 NaCl 150 mM (PBS) are bound in wells of a microtiter plate (high-binding Costar) for 2 hours at 37° C. After 3 washes in PBS/0.1% Tween 20 (PBST), the wells are saturated with PBS containing 2% of BCS.

After 1.30 hour of saturation, the wells are washed three times with PBST, then heterocomplex 2 by 2 dilutions (10, 5, 2.5, 1.25, 0.625, 0.312 and 0.156 µg/ml) made in duplicate, are added in the wells (100 µl/well).

After 2 hours of incubation, the wells are washed three times with PBST. The Tween, a dissociating agent, present in the washing buffer, allows to remove all the molecules which are not covalently linked to the KLH being, itself, specifically bound on the capture antibody.

Then, both heterocomplex dilutions are treated in two different ways:

a) the first set is incubated with an antibody raised against KLH b) the second set is incubated with an antibody raised against cytokin.

After 1.30 hour of incubation at 37° C., the wells are washed as previously indicated then incubated with a secondary antibody coupled to the peroxydase, directed against the origin species of the first antibody. After 1.30 hour of incubation at 37° C., the antibodies are washed again. Then, the addition of the peroxydase substrate, O-PhenyleneDiamine (OPD) allows for the reevaluation of the presence of the KLH bound by the capture antibody and cytokins covalently bound on the KLH.

The amount of KLH bound by the capture antibody and then the amount of cytokin molecules covalently bound on the KLH are calculated by means of calibrating curves done by ELISA.

The percentage of cytokin covalently bound to the KLH is then determined.

Example 12

Biochemical Characterization of the KLH-Murine VEGF Heterocomplex

1. Antigenicity
The KLH-murine VEGF heterocomplex has an antigenicity identical to the antigenicity of murine VEGF.
2. Isoelectrofocusing in Agarose Gel Followed by a Western Blot
FIG. 1 shows that the KLH-murine VEGF heterocomplex migrates under the form of a single strip with a Ip different from the native molecules making it

Example 13

Biochemical Characterization of the KLH-Human VEGF Heterocomplex

Figure 2:
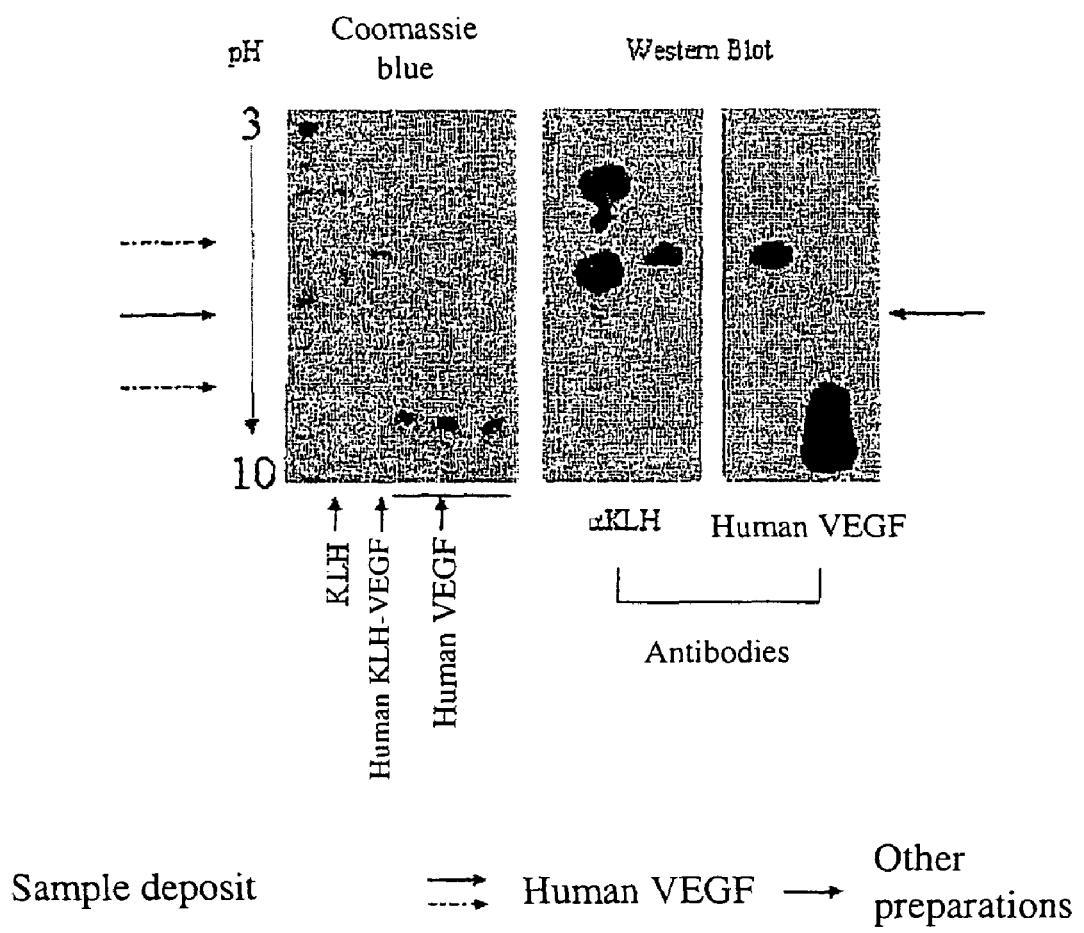
FIG. 2 illustrates the characterization of the immunogenic product comprising human KLH-VEGF heterocomplexes through isoelectrofocusing through a coloration with Coomassie blue, followed by an immunoblotting ("Western Blot"). The isoelectrofocusing gel is represented at the left of the figure. The immunoblotting gels using anti-KLH (left) or human anti-VEGF (right) antibodies are illustrated on the right of the figure.

1. Antigenicity
The KLH-human VEGF heterocomplex has an antigenicity identical to the antigenicity of human VEGF.
2. Isoelectrofocusing Followed by a Western Blot
FIG. 2 shows that the KLH-human VEGF heterocomplex migrates under the form of a single strip with a Ip different from the native molecules making it up. The human VEGF sample was deposited at three different locations in order to show that it still migrates at the same location.

Example 14

Biochemical Characterization of KLH-Murine IL4 Heterocomplex

1. Antigenicity
The KLH-murine IL4 heterocomplex has an antigenicity identical to the antigenicity of murine IL4.

Example 15

Biochemical Characterization of the KLH-Human IL4 Heterocomplex

Figure 3:
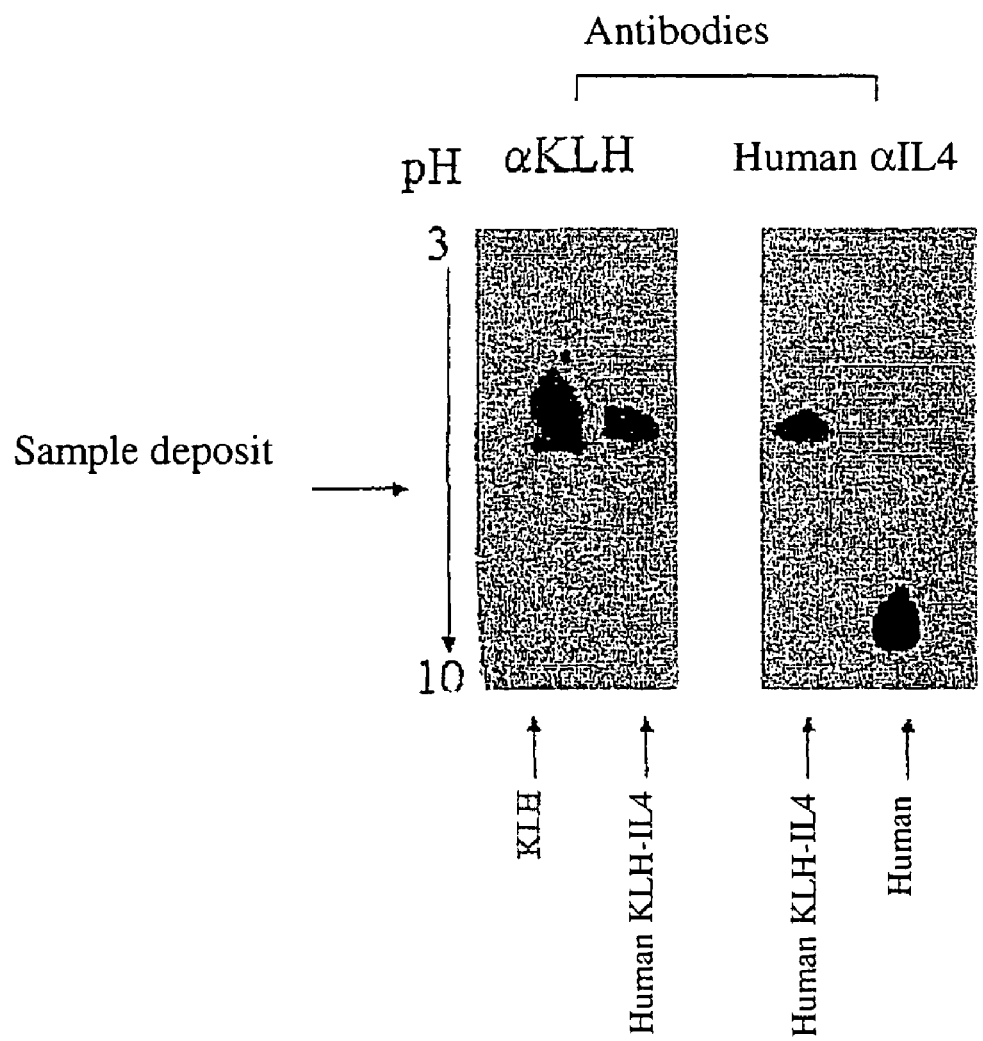
FIG. 3 illustrates the characterization of the immunogenic product comprising human KLH-IL4 heterocomplexes through isoelectrofocusing in an agarose gel followed by the emergence of proteins through immunoblotting ("Western Blot").

1. Antigenicity
The human KLH-IL4 complex has an antigenicity equal to the antigenicity of the human IL4 protein.
2. Isoelectrofocusing Followed by a Western Blot
FIG. 3 shows that the human KLH-IL4 heterocomplex migrates under the form of a single strip with a Ip different from the native molecules making it up.

Example 16

Biochemical Characterization of the KLH-IFNa Heterocomplex

1. Antigenicity
The human KLH-IFNα complex has an antigenicity identical to the antigenicity of the human IFNα.
2. Estimation of the Percentage of Molecules of the Antigen of Interest Covalently Linked to the Carrier Protein Molecule
The KLH-IFNα preparation is passed on a superdex S200 column following the above described conditions. The apparent peak in the exclusion volume was collected, dialyzed then freeze-dried. The concentration in antigen of interest was determined by the indirect ELISA technique. The IFNα amount present in the excluded volume is 30 µg while 1000 µg of IFN were used for preparing the immunogenic product, without any measurable loss of antigen during the preparing method. The percentage of molecules of the antigen of interest covalently linked to the KLH molecule in the immunogenic product comprising KLH-IFNα heterocomplexes can therefore be estimated to approximately 3%.

Example 17

Biochemical Characterization of the gp160-IFNa Heterocomplex

Figure 4:
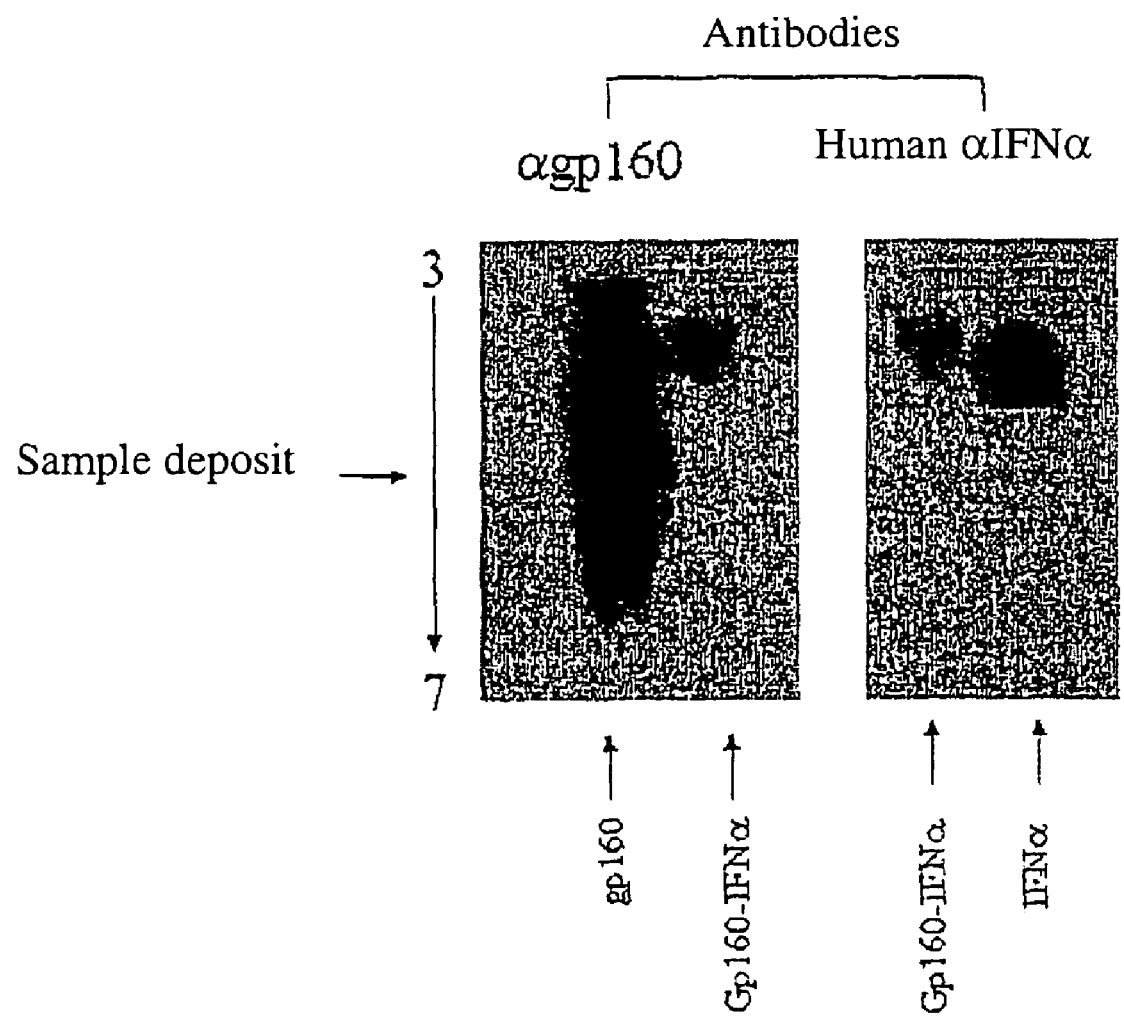
FIG. 4 illustrates the characterization of the immunogenic product comprising gp 160-IFNα complexes through isoelectrofocusing in an agarose gel followed by the mergence of proteins through immunoblotting ("Western Blot").

1. Antigenicity
The human gp160-IFNα complex has an antigenicity identical to the antigenicity of the gp160 protein as well as to that of human IFNα.
2. Isoelectrofocusing Followed by a Western Blot
FIG. 4 shows that the human gp160-IFNα heterocomplex migrates under the form of one single strip at a Ip being quite different from the Ip of the gp160 protein recombining the component. The Ip of such a heterocomplex is slightly lower than that of IFNα.

Example 18

Biochemical Characterization of the gp160-Toxoid Tat Heterocomplex

1. Antigenicity
The gp160-toxoid Tat complex has an antigenicity identical to the antigenicity of the gp160 protein and to that of the Tat protein.

Example 19

Biochemical Characterization of the gp160-GM Tat Heterocomplex

1. Antigenicity
The gp160-GM Tat complex has an antigenicity identical to the antigenicity of the gp160 protein and to that of the Tat protein.

Example 20

Biochemical Characterization of the KLH-Murine IL4 Heterocomplex

1. Antigenicity
The murine KLH-IL4 heterocomplex has an antigenicity identical to the antigenicity of murine IL4.
2. Estimation of the % of Antigen Molecules of Interest Covalently Bound to the Carrier Protein Molecule
11% of molecules of murine IL4 are covalently fixed to the KLH.

Example 21

Biochemical Characterization of the KLH-IFNα Heterocomplex

1. Antigenicity
The KLH-human IFNα complex has an antigenicity identical to the antigenicity of the human IFNα.
2. Estimation of the % of Antigen Molecules of Interest Covalently Fixed to the Carrier Protein Molecule 8% of molecules of human IFNα are covalently bound to the KLH.

Example 22

Biochemical Characterization of the Tat-$_h$IgE Peptide Heterocomplex

1. Antigenicity
The Tat-$_h$IgE peptide complex has an antigenicity comparable to that of human IgE.

Example 23

Biochemical Characterization of the KLH-β Ricin-Heterocomplex

1. Antigenicity
The KLH-β Ricin complex has an antigenicity comparable to that of the β ricin fragment.
2. Isoelectrofocusing Followed by a Western Blot
The complex migrates under the form of a single strip and the presence of the P fragment is enhanced by Western Blot.

Examples of Immunogenic Activity of Heterocomplexes

Example 24

Immunogenic Activity of the KLH-Murine VEGF Heterocomplex

Figure 5:
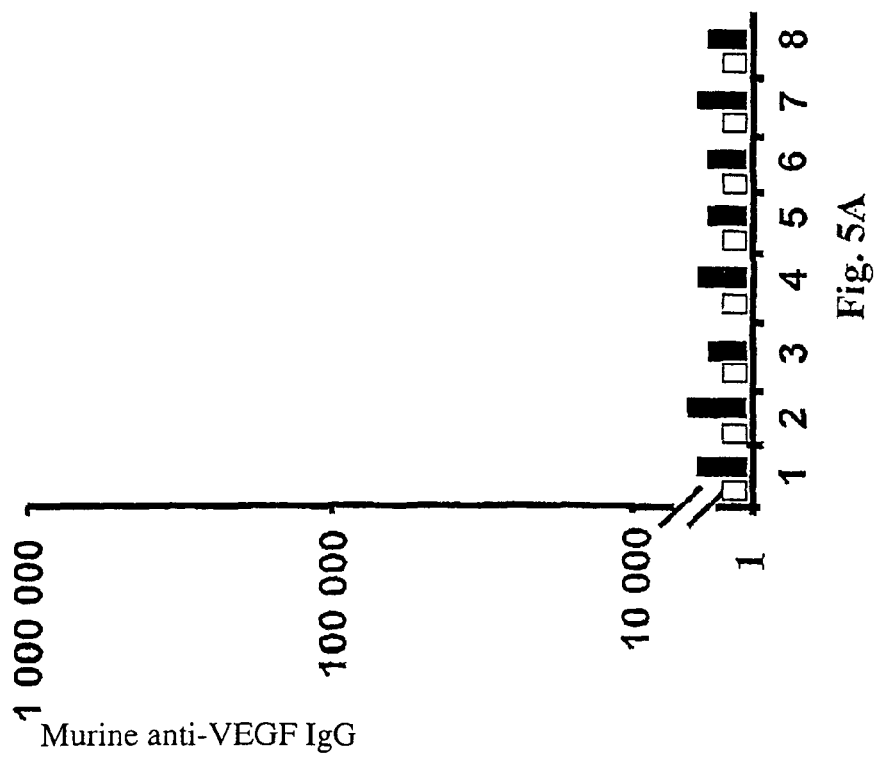
FIG. 5 illustrates the immunogenic (humoral) activity of the murine KLH-VEGF immunogenic product through determination of the title antibody obtained after an immunization of mice.
Figure 6:
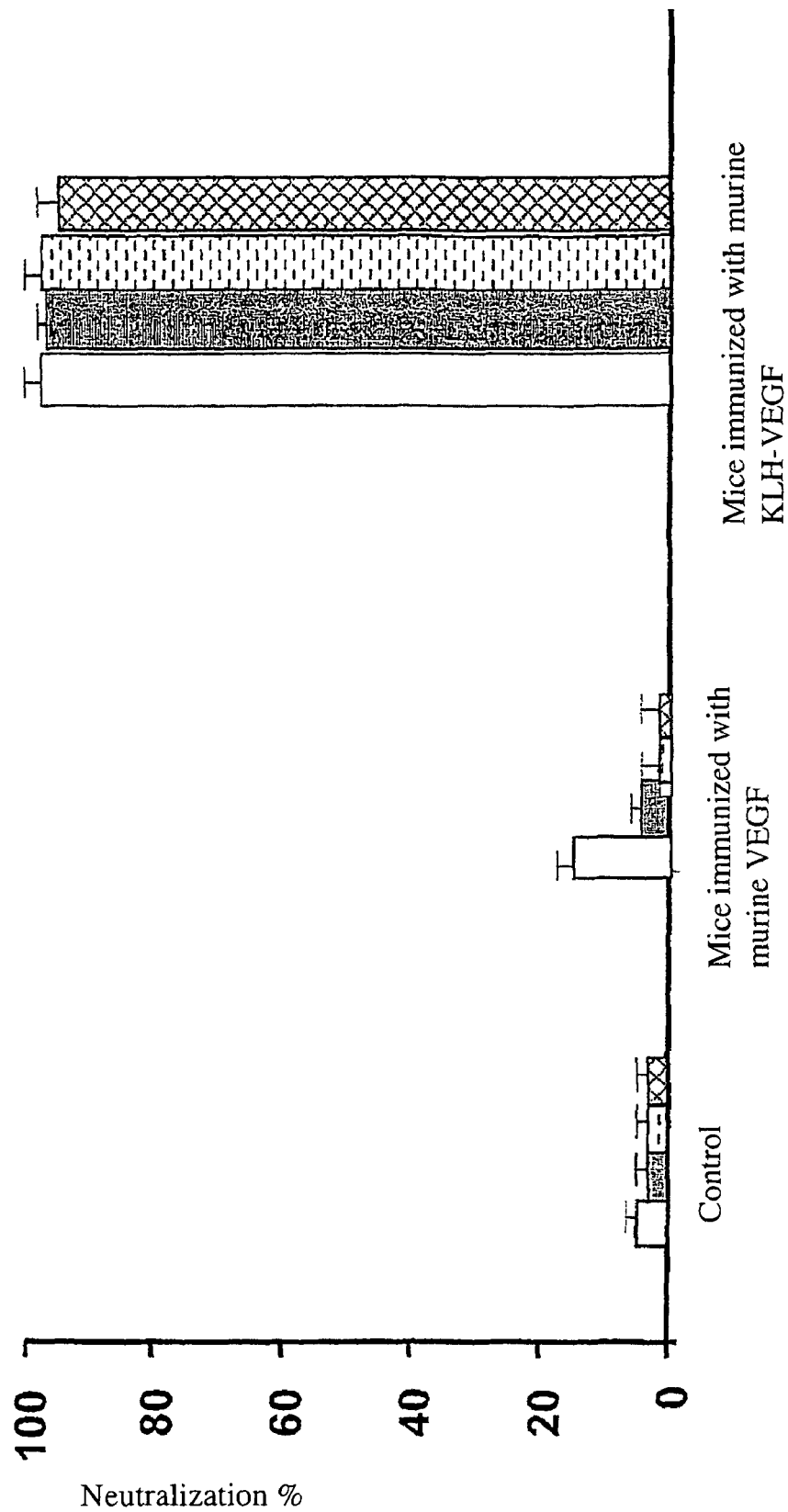
FIG. 6 shows the immunogenic (humoral) activity of the murine KLH-VEGF immunogenic product, through determination of the neutralizing power of antibodies obtained after immunization, towards the angiogenic activity of the VEGF protein.

A. Material and Methods
The immunogenic (humoral) of the KLH-murine VEGF preparation compared to that of the murine VEGF was studied in 18 to 20 g BALB c mouse.
1—Immunization
At days 0, 7, 14, 21, a group of 8 mice receives a 0.1 ml (10 µg) injection of an AIF emulsion through the intramuscular route. A 5 µg booster injection in AIF is given at D60.
A blood sample at the retro-orbital level is taken from each mouse before the first injection at d-2.
3 control mice receive the same preparations without any immunogen.
The mice are sacrificed 12 days after the last immunization.
2—Toxicity
The abnormal toxicity is studied in 3 mice receiving one human dose (50 µg) according to the pharmacopeia.
The lack of immunotoxicity of the heterocomplex is evaluated in vitro by cell proliferation test conducted on PBMCs cultivated in the presence of the complex and stimulated by PPD or toxoid tetanos.
B. Results
1. Lack of Toxicity of the Heterocomplex in Vivo and in Vitro
The mice immunized both with the KLH-murine VEGF preparation and the murine VEGF only do not show any clinical sign and no anatomic wound. The immunosuppression test shows that doses of 100 ng/ml to 1 µg/ml of KLH-murine VEGF do not reduce the proliferation of lymphocytes.
None of the three mice immunized with 50 µg of the heterocomplex show any sign of toxicity (temperature, cutaneous disorders, systemic or regional signs) during the 7 days following the injection.
2—Humoral Response
The humoral response is measured by the presence in the serum of antibodies of the IgG type directed against the murine VEGF, determined by ELISA and expressed in titer (opposite of the dilution giving an optical density higher than 0.3). FIG. 5 shows the resulting antibody titers.
The mice immunized with the KLH-murine VEGF preparation show higher antibody titers of the IgG type than those of mice immunized with the murine VEGF only.
The neutralizing activity of such antibodies was measured by means of the biological activity test of VEGF, selective growth factor of endothelial cells. Endothelial cells (HU-VECs) are cultivated in flat bottom wells of a microculture plate at a level of 3,000 cells per well. The sera of each group of mice were pooled. Different dilutions of such serum pools (1/100-1/800) taken at D-2 and D72 were pre-incubated for 2 hours with 20 ng/ml of murine VEGF then deposited on such endothelial cells. The cell culture continued at 37° C. in a humid atmosphere loaded with 5% of $CO_2$ for 3 days. 18 hours before the end of the incubation, 0.5 µCi of titered thymidine/well were added. The neutralizing sera prevent the murine VEGF from inducing the proliferation of endothelial cells, while non-neutralizing sera allow for the proliferation of such cells. The results are expressed in neutralization percentage. FIG. 6 shows the obtained results.
The antibodies induced by the complex have a higher neutralizing power than that induced by the murine VEGF.

Example 25

Immunogenic Activity of the KLH-Human VEGF Heterocomplex

Figure 7:
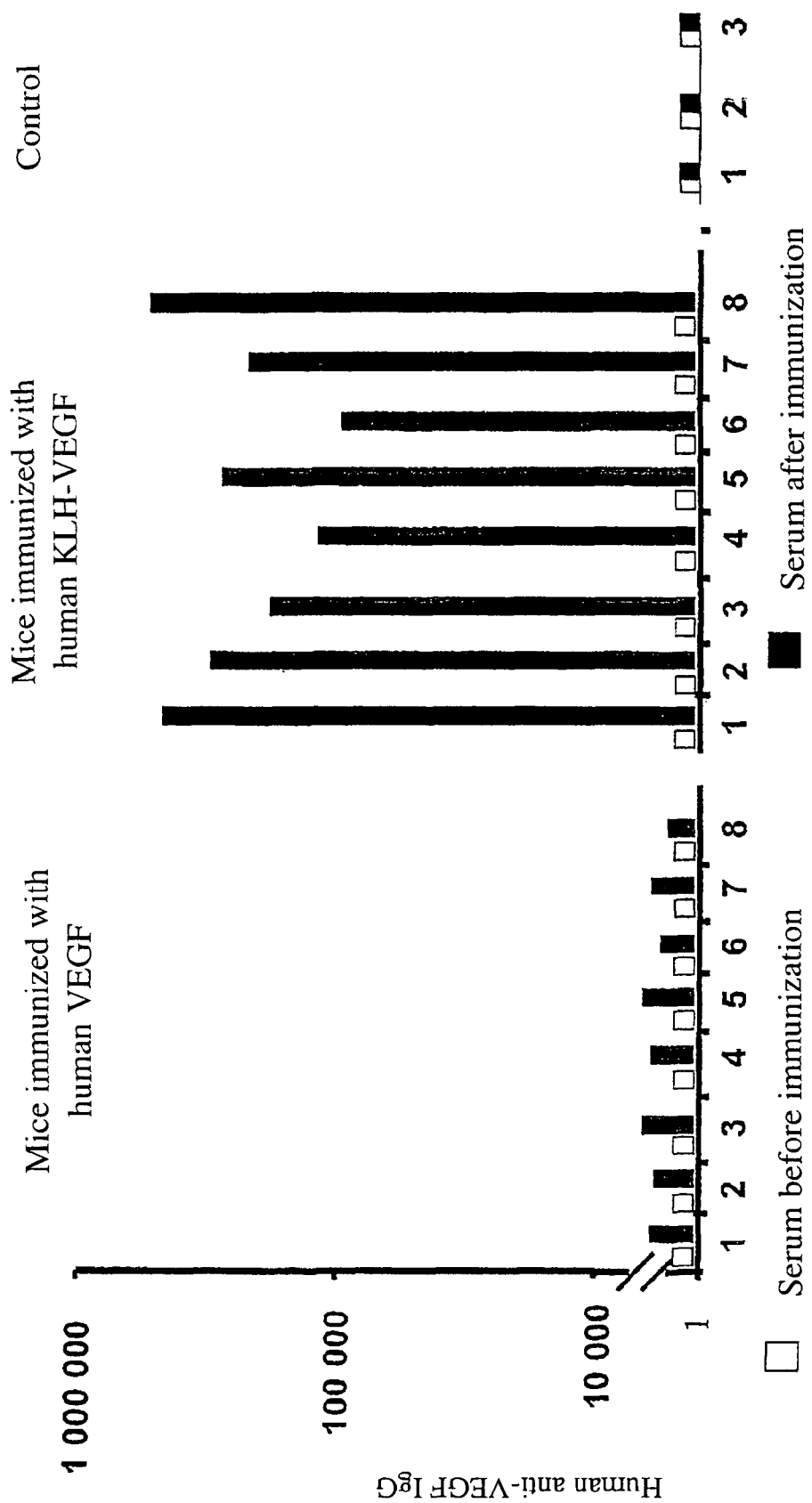
FIG. 7 illustrates the immunogenic (humoral) activity of the human KLH-VEGF immunogenic product, through determination of the antibody title obtained after immunization of mice.

A. Material and Methods
The immunogenic (humoral) of the KLH-human VEGF preparation compared to that of the human VEGF was studied in 18 to 20 g BALB c mouse.
1—Immunization
At days 0, 7, 14, 21, a group of 8 mice receives a 0.1 ml (10 µg) injection of an AIF emulsion through the intramuscular route. A 5 µg booster injection in AIF is given at D60.
A blood sample at the retro-orbital level is taken from each mouse before the first injection at d-2.
3 control mice receive the same preparations without an immunogen.
The mice are sacrificed 12 days after the last immunization.
2—Toxicity
The abnormal toxicity is sought in 3 mice receiving one human dose (50 µg) according to the pharmacopeia.
The lack of immunotoxicity of the heterocomplex is evaluated in vitro by a cell proliferation test conducted on PBMCs cultivated in the presence of the complex and stimulated by PPD or toxoid tetanos.
B. Results
1—Lack of Toxicity of the Heterocomplex in Vivo and in Vitro
The mice immunized both with the murine KLH-VEGF preparation and the murine VEGF only do not show any clinical sign and no anatomic wound. The immunosuppression test shows that doses of 100 ng/ml to 1 µg/ml of KLH-human VEGF do not reduce the proliferation of lymphocytes.
None of the three mice immunized with 50 µg of the heterocomplex show any sign of toxicity (temperature, cutaneous disorders, systemic or regional signs) during the 7 days following the injection.
2—Humoral Response
The humoral response is measured by the presence in the serum of antibodies of the IgG type raised against the human VEGF, determined by ELISA and expressed in titer (opposite of the dilution giving an optical density higher than 0.3). FIG. 7 shows the resulting antibody titers.

The mice immunized with the KLH-human VEGF preparation show higher antibody titers of the IgG type than those of mice immunized with the human VEGF only.

Figure 8:
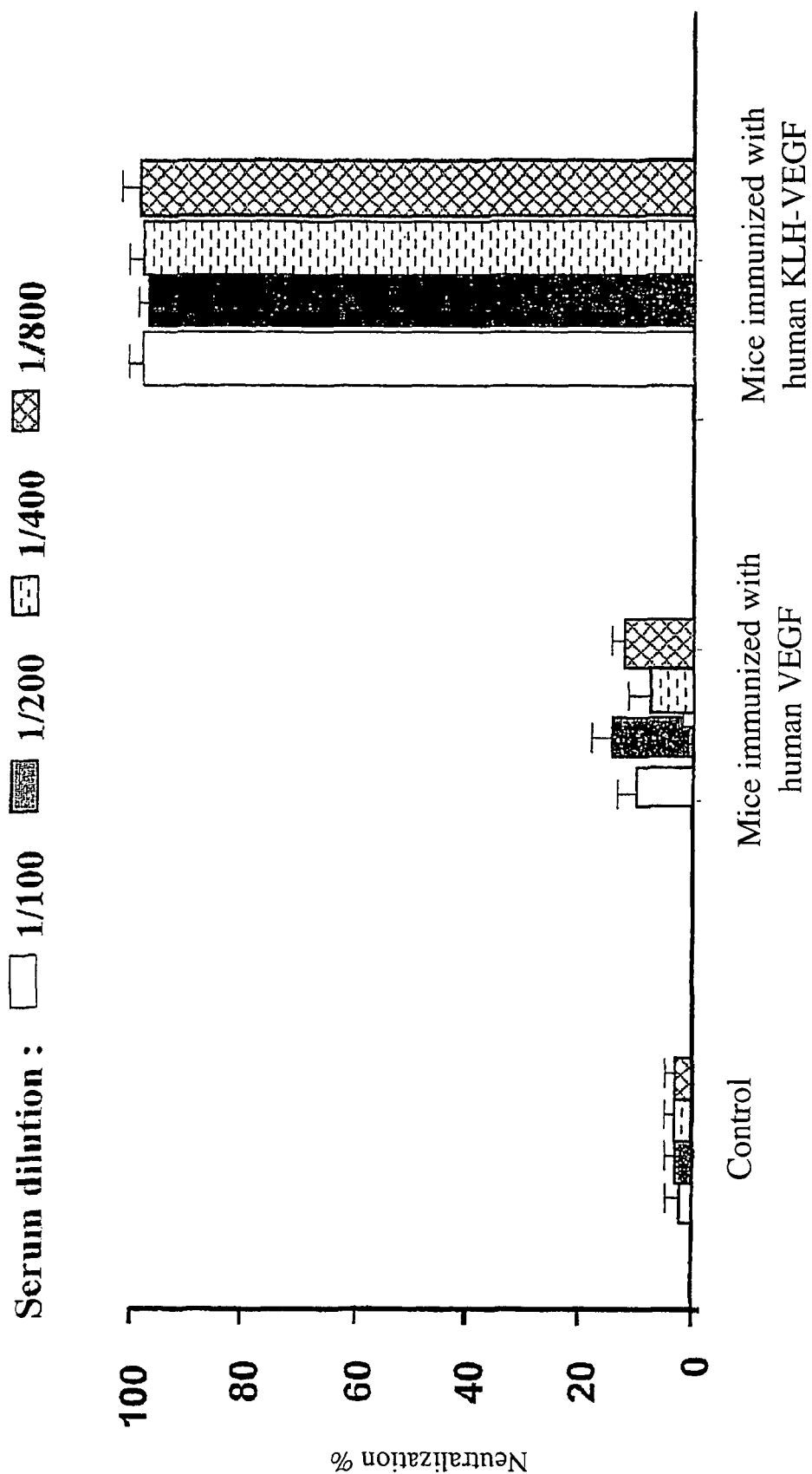
FIG. 8 illustrates the immunogenic (humoral) activity of the human KLH-VEGF immunogenic product, through determination of the neutralizing power of antibodies obtained after immunization, towards the angiogenic activity of the VEGF protein, measured through the proliferation of endothelial cells.

The neutralizing activity of such antibodies was measured by means of the biological activity test of VEGF, selective growth factor of endothelial cells. Endothelial cells (HU-VECs) are cultivated in flat bottom wells of a microculture plate at a level of 3,000 cells per well. The sera of each group of mice were pooled. Different dilutions of such serum pools (1/100-1/800) taken at D-2 and D72 were pre-incubated for 2 hours with 20 ng/ml of human VEGF then deposited on such endothelial cells. The cell culture is continued at 37° C. in a humid atmosphere loaded with 5% of $CO_2$ for 3 days. 18 hours before the end of the incubation, 0.5 µCi of titered thymidine/well were added. The neutralizing sera prevent the human VEGF from inducing the proliferation of endothelial cells, while non-neutralizing sera allow for the proliferation of such cells. The results are expressed in neutralization percentage. FIG. 8 shows the obtained results.

The antibodies induced by the complex have a higher neutralizing power than that induced by the human VEGF.

Example 26

Immunogenic Activity of the KLH-Murine IL4 Heterocomplex

A. Material and Methods

The immunogenic (humoral) activity of the murine KLH-IL4 preparation compared to that of the murine IL4 was studied in 18 to 20 g BALB c mouse.

1—Immunization

At days 0, 7, 14, 21, a group of 8 mice receives a 0.1 ml (10 µg) injection of an AIF emulsion through the intramuscular route. A 5 µg booster injection in AIF is given at D60.

A blood sample at the retro-orbital level is taken from each mouse before the first injection at D-2 and D72.

3 control mice receive the same preparations without an immunogen.

14 days after the last immunization, the control mice and the mice immunized with the KLH-murine IL4 were challenged with birch-tree pollen in the presence of alum (100 µg/mice) through the subcutaneous route at D74, D95 and D109. Blood samples are regularly taken in order to follow the occurrence of class G and E antibodies raised against Bet v 1, a major allergen of the birch-tree pollen.

2—Toxicity

The abnormal toxicity is sought in 3 mice receiving one human dose (50 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

1. Lack of Toxicity of the Heterocomplex in Vivo and in Vitro

The mice both immunized with the KLH-murine IL4 preparation and the murine IL4 only do not show any clinical sign and no anatomic wound. The immunosuppression test shows that doses of 100 ng/ml to 1 µg/ml of KLH-murine IL4 do not reduce the proliferation of lymphocytes.

None of the three mice immunized with 50 µg of the heterocomplex show any sign of toxicity (temperature, cutaneous disorders, systemic or regional signs) during the 7 days following the injection.

2—Humoral Response

Figure 9:
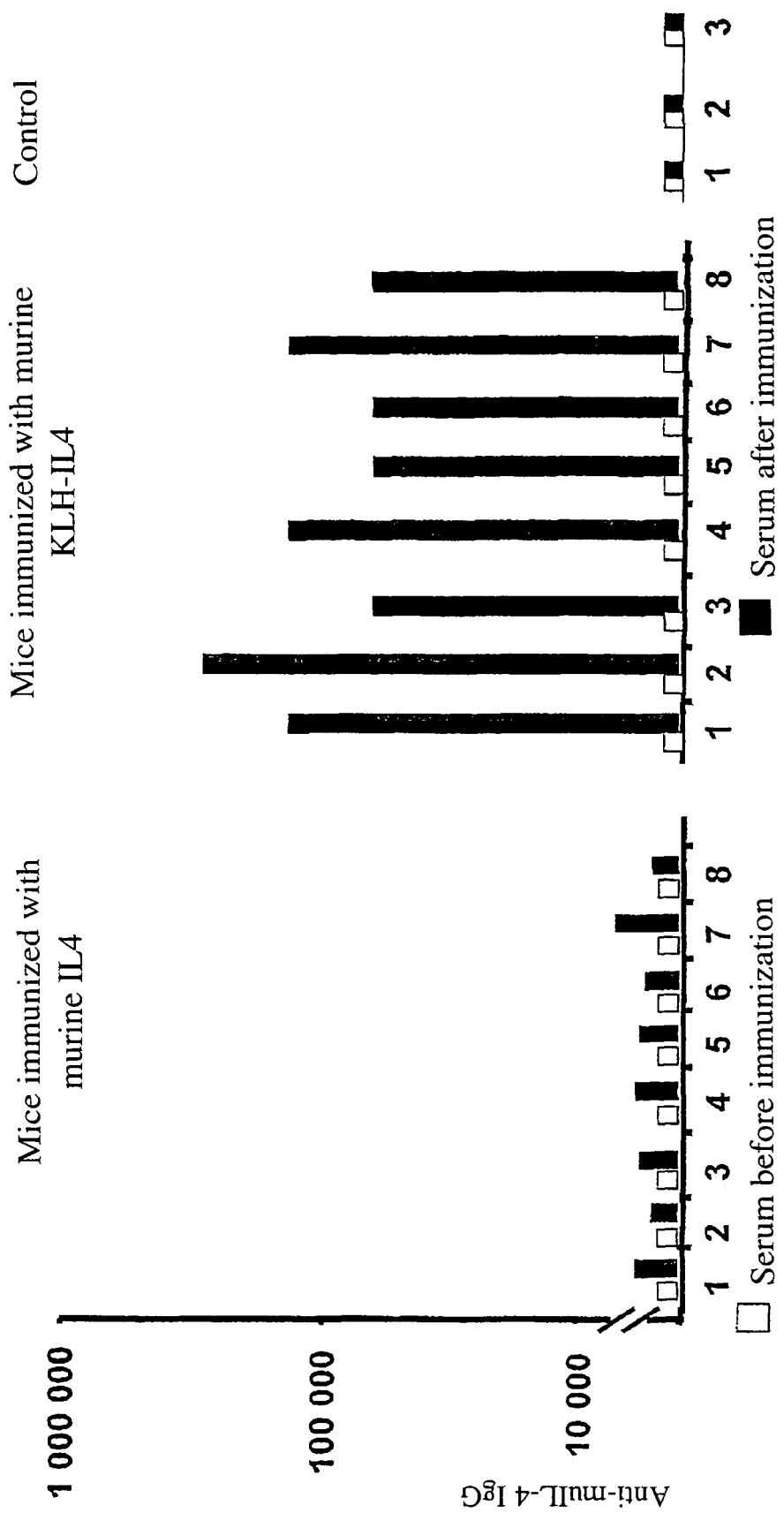
FIG. 9 illustrates the immunogenic (humoral) activity of the murine KLH-IL4 immunogenic product, through determination of the title antibody obtained after immunization.

The humoral response is measured by the presence in the serum of antibodies of the IgG type raised against the murine VEGF, determined by ELISA and expressed in titer (opposite of the dilution giving an optical density higher than 0.3). FIG. 9 shows the resulting antibody titers.

The mice immunized with the KLH-murine IL4 preparation show higher antibody titers of the IgG type than those of mice immunized with the murine IL4 only.

Figure 10:
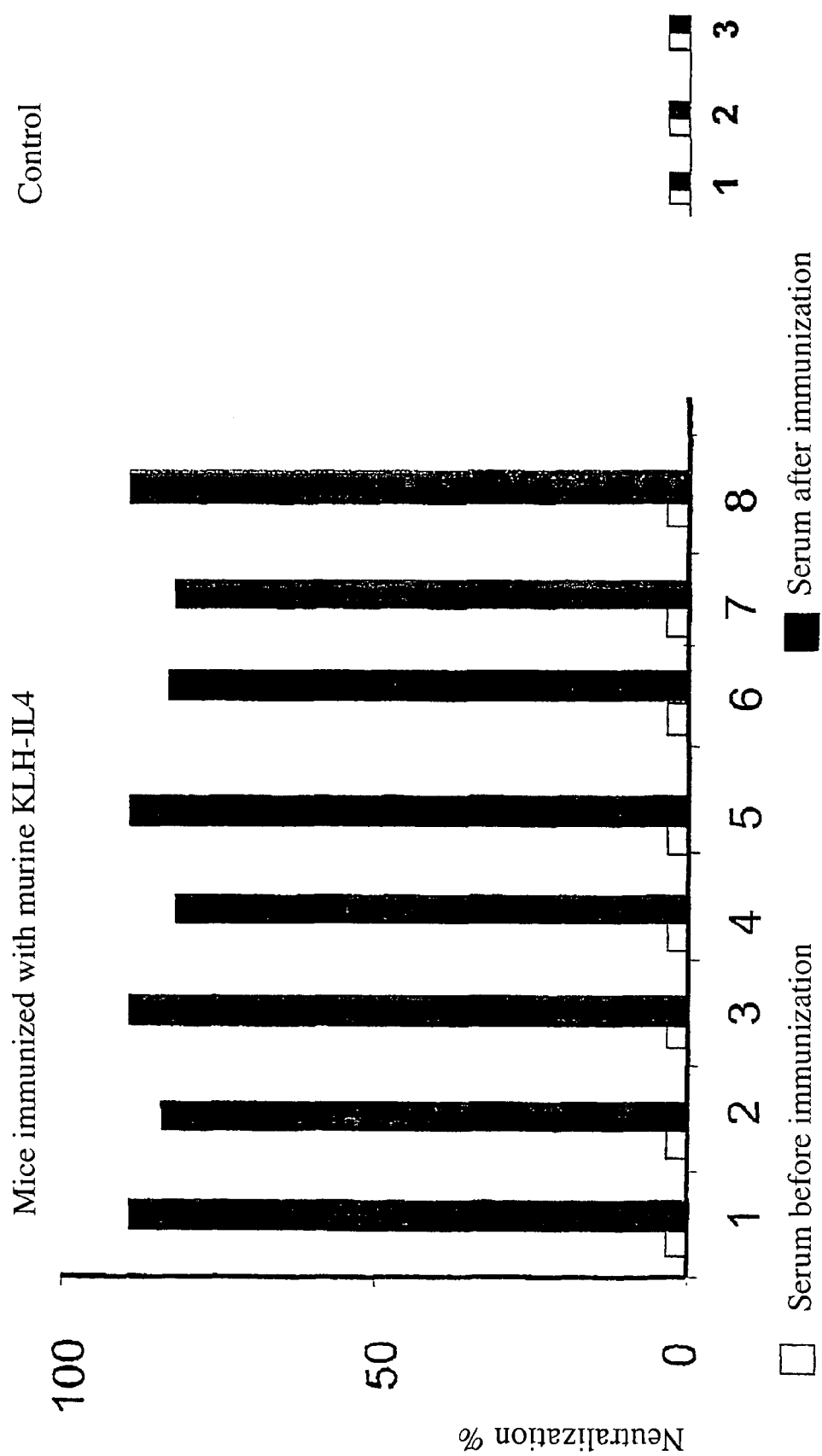
FIG. 10 illustrates the immunogenic (humoral) activity of the murine KLH-IL4 immunogenic product, through determination of the neutralizing power of antibodies obtained after immunization, towards the inducing activity of the proliferation of HT-2 cells by the IL4.

The neutralizing activity of those antibodies present in mice immunized with the KLH-murine IL4 preparation was measured by means of the biological activity test of the murine IL4. This test uses HT-2 cells, murine cell lineages the growth of which is IL4 murine-dependent (Watson, J. 1979. J. Exp. Med. 150:1510.). Endothelial cells HT-2 are cultivated in round bottom wells of a microculture plate at a level of 10,000 cells per well. Sera diluted at 1/50 taken at D-2 and D72 are pre-incubated for 2 hours with 50 ng/ml of murine H4 then deposited on HT-2 cells. The cell culture is continued at 37° C. in a humid atmosphere loaded with 5% of $CO_2$ for 3 days. 4 hours before the end of the incubation, 0.5 µCi of titered thymidine/well were added. The neutralizing sera prevent the murine IL4 from inducing the proliferation of HT-2 cells, while non-neutralizing sera allow for the proliferation of such cells. The results are expressed in neutralization percentage. FIG. 10 shows the obtained results.

The antibodies induced by the complex are neutralizing.

Figure 11:
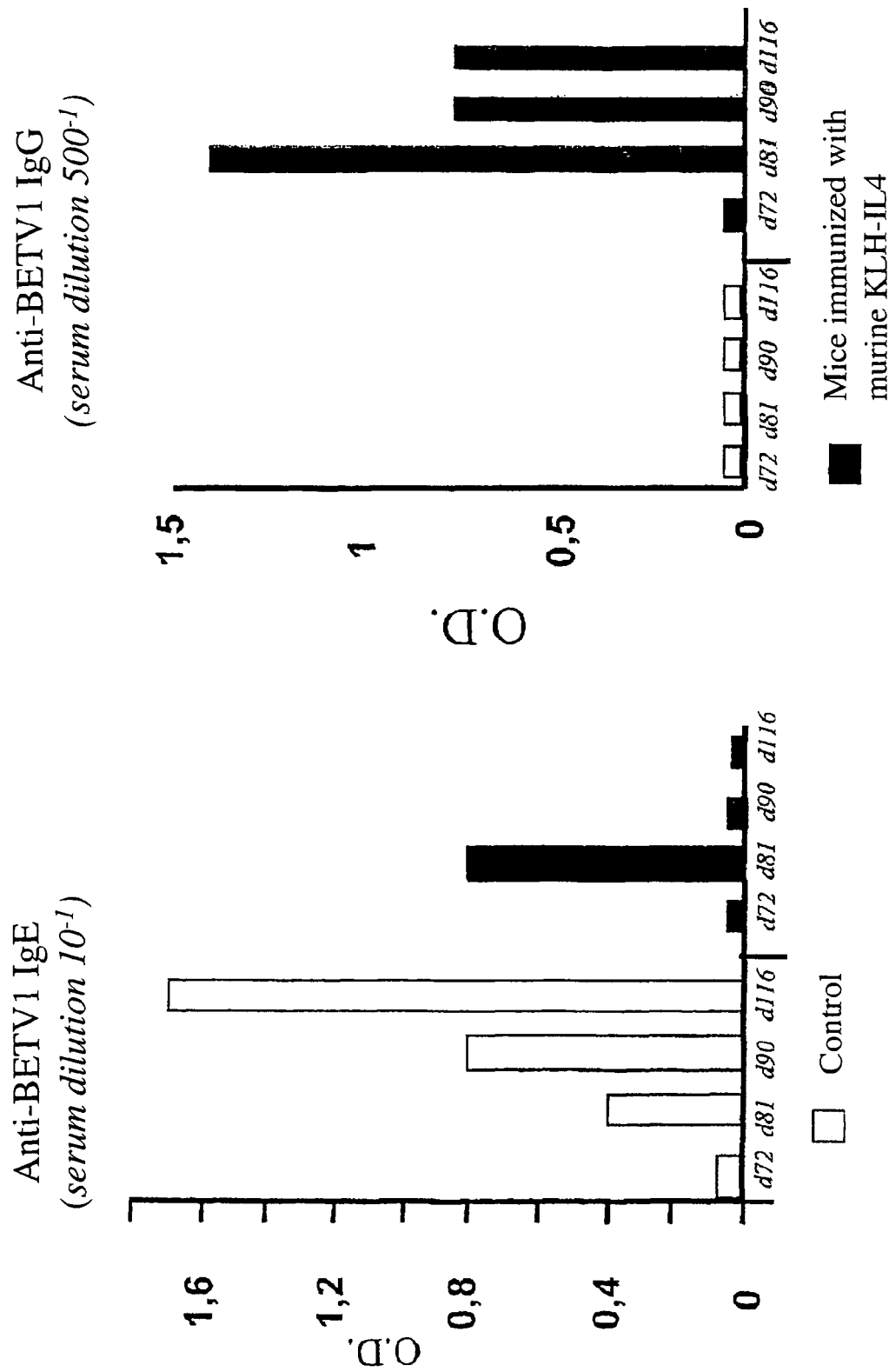
FIG. 11 illustrates the results of the production of the IgG and IgE class antibodies raised against Bet v 1, after the injection of birch-tree pollen, to mice preliminarily immunized with an immunogenic product according to the invention comprising KLH-IL4 complexes.

Moreover, such neutralizing antibodies raised against murine IL4 prevent the production, by those mice, of antibodies of the IgE type raised against Bet v 1, when the latter are challenged with birch-tree pollen. FIG. 11 indeed shows that mice immunized with KLH-murine IL4 have neutralizing IgGs raised against murine NL4 blocking the production of IgE raised against Bet v 1 and start to produce antibodies of the IgG type directed against Bet v 1. On the other hand, mice which did not receive any murine KLH-IL4 and therefore not having any antibodies of the IgG type directed against IL4, only produce antibodies of the IgE type directed against Bet v 1.

Example 27

Immunogenic Activity of the KLH-Human IL4 Heterocomplex

A. Material and Methods

The immunogenic (humoral) of the KLH-human IL4 preparation compared to that of the human IL4 was studied in 18 to 20 g BALB c mouse.

1—Immunization

At days 0, 7, 14, 21, a group of 3 mice receives a 0.1 ml (10 µg) injection of an AIF emulsion through the intramuscular route. A 5 µg booster injection in AIF is given at D60.

A blood sample at the retro-orbital level is taken from each mouse before the first injection at d-2.

3 control mice receive the same preparations without an immunogen.

The mice are sacrificed 12 days after the last immunization.

2—Toxicity

The abnormal toxicity is sought in 3 mice receiving one human dose (50 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

1. Lack of Toxicity of the Heterocomplex in Vivo and in Vitro

The mice both immunized with the KLH-human ILA preparation and the human IL4 only do not show any clinical sign and no anatomic wound. The immunosuppression test shows that doses of 100 ng/ml to 1 µg/ml of KLH-human IL4 do not reduce the proliferation of lymphocytes.

None of the three mice immunized with 50 µg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the human IL4, determined by ELISA and expressed in titer (opposite of the dilution giving an optical density higher than 0.3).

TABLE 1

| | Titer | |
|---|---|---|
| | D-2 | D72 |
| Control mice: | | |
| Control mouse 1 | $<500^{-1}$ | $<500^{-1}$ |
| Control mouse 2 | $<500^{-1}$ | $<500^{-1}$ |
| Control mouse 3 | $<500^{-1}$ | $<500^{-1}$ |
| Mice immunized with human IL4: | | |
| mouse 4 | $<500^{-1}$ | $32,000^{-1}$ |
| mouse 5 | $<500^{-1}$ | $48,000^{-1}$ |
| mouse 6 | $<500^{-1}$ | $16,000^{-1}$ |
| Mice immunized with the KLH-human IL4 complex: | | |
| mouse 7 | $<500^{-1}$ | $256,000^{-1}$ |
| mouse 8 | $<500^{-1}$ | $128,000^{-1}$ |
| mouse 9 | $<500^{-1}$ | $128,000^{-1}$ |

The mice immunized with the KLH-human IL4 preparation show higher antibody titers of the IgG type than those of mice immunized with the human IL4 only.

Figure 12:
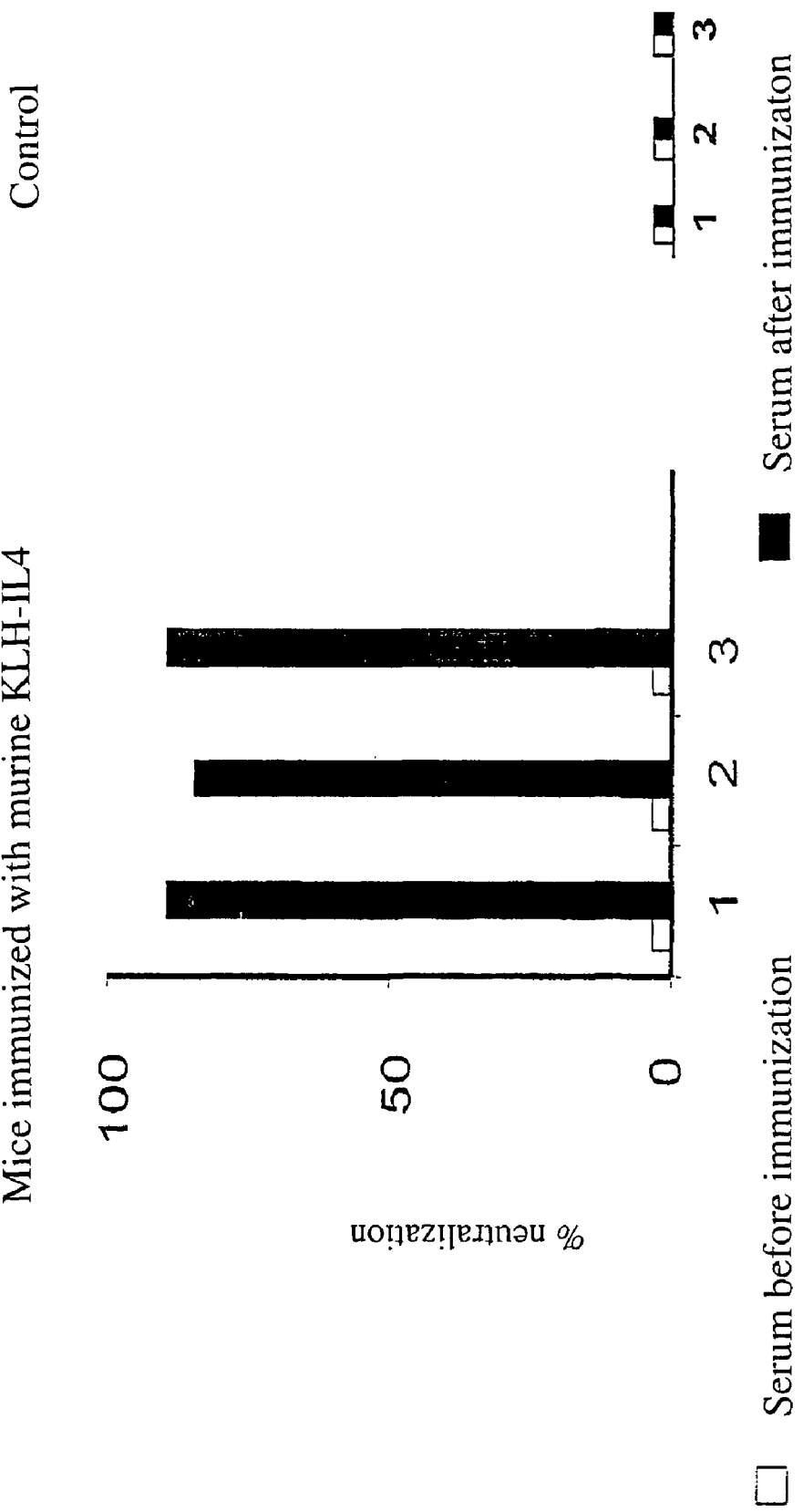
FIG. 12 illustrates the immunogenic (humoral) activity of the human KLH-IL4 immunogenic product through determination of the neutralizing power of antibodies obtained after immunization, towards the inducing activity of the proliferation of HT-2 cells by the IL4.
Figure 13:
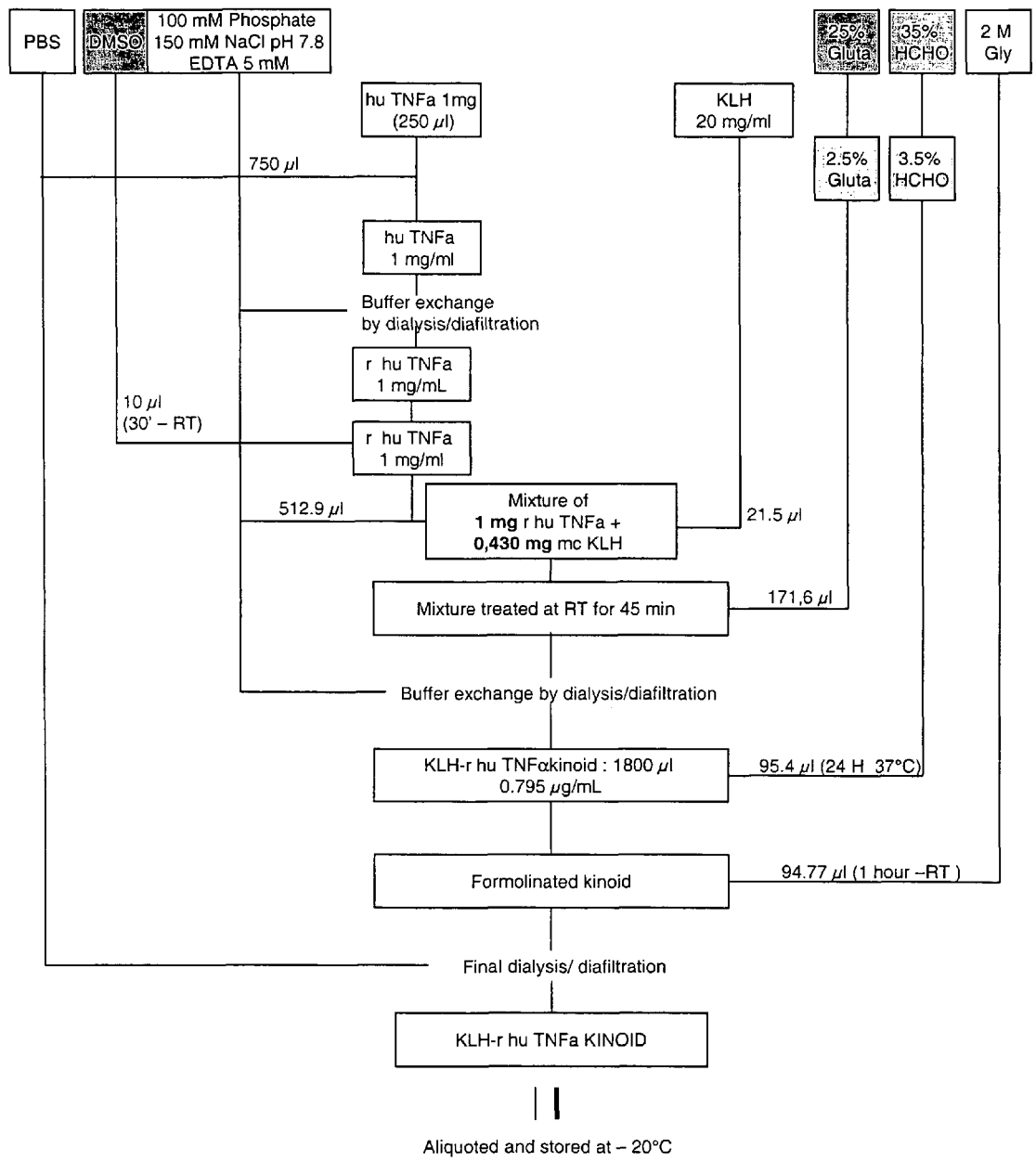
FIG. 13 consists of a scheme that illustrates the general procedure for manufacturing a stable immunogenic product according to the invention.
Figure 18A:
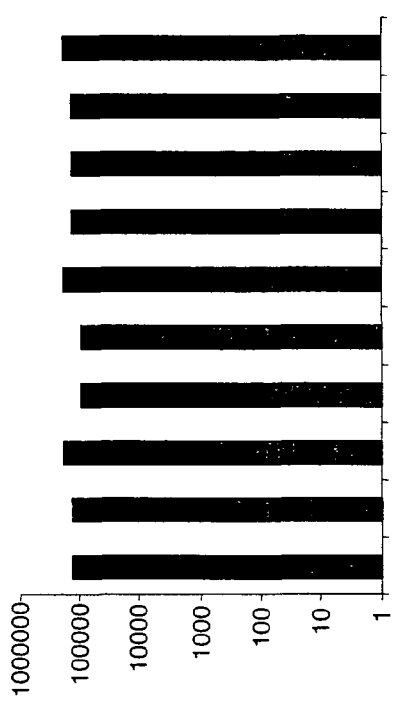
FIGS. 18A, 18B, and 18C illustrate the humoral response of transgenic huTNFa B6.SJL-Tg(TNF) N2 mice immunized respectively with (A) Control PBS buffer, (B) KLH alone, (C) of a stable immunogenic product manufactured as disclosed in Example 35 and (D) of a stable immunogenic product manufactured as disclosed in Example 35 combined with methotrexate. Abscissa: individuals; Ordinate: IgG anti-TNFa antibody titers.
Figure 18B:
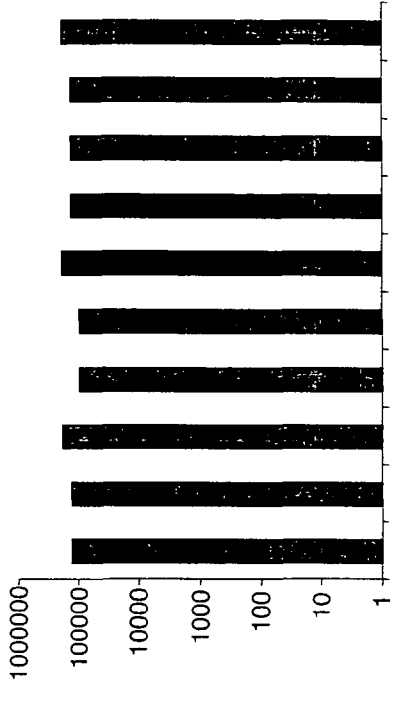
Figure 18C:
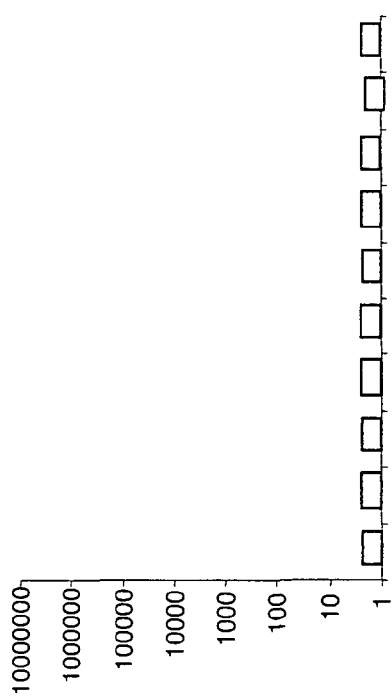
Figure 18D:
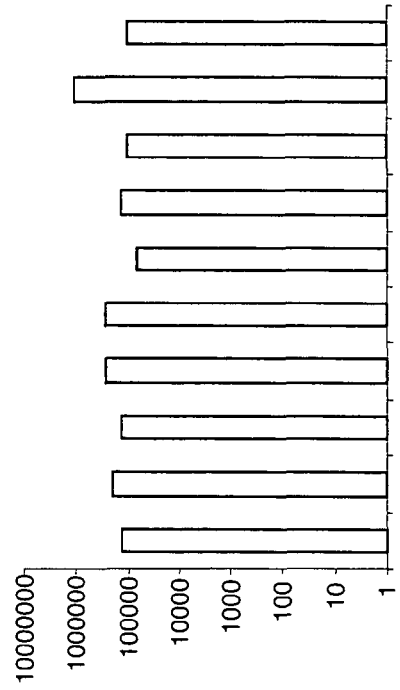

The neutralizing activity of such antibodies induced by the human KLH-IL4 preparation was measured by means of the biological activity test of human IL4. This test uses TF-1 cells, human cell lineage the growth of which is IL4 human-dependent (Kitamura, T. et al., 1989. J. Cell Physiol. 140:323-34). TF-1 cells are cultivated in round bottom wells of a microculture plate at a level of 10,000 cells per well. Sera diluted at 1/50 taken at D-2 and D72 preincubated for 2 hours with 50 ng/ml of human IL4 were then deposited on the TF-1 cells. The cell culture is continued at 37° C. in a humid atmosphere loaded with 5% of $CO_2$ for 3 days. 4 hours before the end of the incubation, 0.5 µCi of titered thymidine/well were added. The neutralizing sera prevent the human IL4 from inducing the proliferation of TF-1 cells, while non-neutralizing sera allow for proliferation of such cells. The results are expressed in neutralization percentage. FIG. 12 shows the obtained results.

The antibodies induced by the complex are neutralizing.

Example 28

Immunogenic Activity of the KLH-IFNα Heterocomplex

A. Material and Methods

The immunogenic (humoral) activity of the KLH-human IFNα preparation compared to that of the human IFNα was studied in 18 to 20 g BALB c mouse.

1—Immunization

At days 0, 7, 14, 21, a group of 3 mice receives a 0.1 ml (10 µg) injection of an AIF emulsion through the intramuscular route. A 5 µg booster injection in AIF is given at D60.

A blood sample at the retro-orbital level is taken from each mouse before the first injection at D-2.

3 control mice receive the same preparations without an immunogen.

The mice are sacrificed 12 days after the last immunization.

2—Toxicity

The abnormal toxicity is sought in 3 mice receiving one human dose (50 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

1—Lack of Toxicity of the Heterocomplex in Vivo and in Vitro

The mice both immunized with the KLH-human IFNα preparation and the human IFNα only do not show any clinical sign and no anatomic wound. The immunosuppression test shows that doses of 100 ng/ml to 1 µg/ml of KLH-human IFNα do not reduce the proliferation of lymphocytes.

None of the three mice immunized with 100 µg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the human NFNA, determined by ELISA and expressed in titer (opposite of the dilution giving an optical density higher than 0.3). The table 2 shows the resulting antibody titers.

TABLE 2

| | Titer | |
|---|---|---|
| | D-2 | D72 |
| Control mice: | | |
| Control mouse 1 | $<500^{-1}$ | $<500^{-1}$ |
| Control mouse 2 | $<500^{-1}$ | $<500^{-1}$ |
| Control mouse 3 | $<500^{-1}$ | $<500^{-1}$ |
| Mice immunized with IFNα: | | |
| mouse 4 | $<500^{-1}$ | $96,000^{-1}$ |
| mouse 5 | $<500^{-1}$ | $128,000^{-1}$ |
| mouse 6 | $<500^{-1}$ | $96,000^{-1}$ |
| Mice immunized with the KHL-IFNα complex: | | |
| mouse 7 | $<500^{-1}$ | $96,000^{-1}$ |
| mouse 8 | $<500^{-1}$ | $96,000^{-1}$ |
| mouse 9 | $<500^{-1}$ | $128,000^{-1}$ |

The mice immunized with the KHL-human IFNα preparation show antibody titers of the IgG type equivalent to those of mice immunized with the human IFNα only.

The neutralizing activity of such antibodies was measured by means of the biological activity test of the human IFNα. (Rubinstein S, J Viral, 1981, 755-8). The aim of this test for measuring the antiviral effect is to evaluate the inhibition of the MDBK cell lysis by the VSV (Vesicular Stomatitis virus) in the presence of IFN. MDBK cells are cultivated in round bottom wells of a microculture plate at a level of 350,000 cells per well. Different dilutions of sera (1/100 at 1/800) taken at D-2 and D72 were pre-incubated for 2 hours with 5 ng/ml of human IFNa then deposited on MDBK cells. After 20 hours of cell culture performed at 37° C. in a humid atmosphere loaded with 5% of CO2, the diluted sera present in the wells are removed, the cells washed, then 100 μl containing 100 LD50 (50% lethal dose) of VSV virus are added. 18 hours after the addition of the virus the lytic effect of the virus is measured. The neutralizing sera allow the VSV to lyse cells, while non-neutralizing sera prevent such a lysis. The results are expressed in neutralization percentage.

TABLE 3

|  |  | 1/100 | 1/200 | 1/400 | 1/800 |
|---|---|---|---|---|---|
| Mice immunized with IFNα: | | | | | |
| mouse 4 | D-2 | 0 | 0 | 0 | 0 |
|  | D72 | 100 | 75 | 65 | 50 |
| mouse 5 | D-2 | 0 | 0 | 0 | 0 |
|  | D72 | 100 | 67 | 60 | 55 |
| mouse 6 | D-2 | 0 | 0 | 0 | 0 |
|  | D72 | 100 | 72 | 65 | 60 |
| Mice immunized with the KLH-IFNα conjugate | | | | | |
| mouse 7 | D-2 | 0 | 0 | 0 | 0 |
|  | D72 | 100 | 100 | 100 | 100 |
| mouse 8 | D-2 | 0 | 0 | 0 | 0 |
|  | D72 | 100 | 100 | 100 | 100 |
| mouse 9 | D-2 | 0 | 0 | 0 | 0 |
|  | D72 | 100 | 100 | 100 | 100 |

The antibodies induced by the complex have a higher neutralizing power than that induced by the human IFNα. The results are expressed in neutralization percentage.

Example 29

Immunogenic Activity of the gp160-IFNα Heterocomplex

A. Material and Methods

The immunogenic (humoral) activity of the human gp160-IFNα preparation compared to that of the human IFNα was studied in 18 to 20 g BALB c mouse.

1—Immunization

At days 0, 7, 14, 21, a group of 3 mice receives a 0.1 ml (10 μg) injection of an AIF emulsion through the intramuscular route. A 5 μg booster injection in AIF is given at D60.

A blood sample at the retro-orbital level is taken from each mouse before the first injection at D-2.

3 control mice receive the same preparations without an immunogen.

The mice are sacrificed 12 days after the last immunization.

2—Toxicity

The abnormal toxicity is sought in 3 mice receiving one human dose (100 μg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

1—Lack of Toxicity of the Heterocomplex in Vivo and in Vitro

The mice immunized both with the gp160-human IFNa preparation and the human IFNα only, do not show any clinical sign and no anatomic wound. The immunosuppression test shows that doses of 100 ng/ml to 1 μg/ml of gp160-human IFNα do not reduce the proliferation of lymphocytes.

None of the three mice immunized with 100 μg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the human IFN, determined by ELISA and expressed in titer (opposite of the dilution giving an optical density higher than 0.3).

TABLE 4

|  | Titer | |
|---|---|---|
|  | D-2 | D72 |
| Control mice: | | |
| Control mouse 1 | $<500^{-1}$ | $<500^{-1}$ |
| Control mouse 2 | $<500^{-1}$ | $<500^{-1}$ |
| Control mouse 3 | $<500^{-1}$ | $<500^{-1}$ |
| Mice immunized with IFNα: | | |
| mouse 4 | $<500^{-1}$ | $64,000^{-1}$ |
| mouse 5 | $<500^{-1}$ | $96,000^{-1}$ |
| mouse 6 | $<500^{-1}$ | $128,000^{-1}$ |
| Mice immunized with the gp160-IFNα complex: | | |
| mouse 7 | $<500^{-1}$ | $96,000^{-1}$ |
| mouse 8 | $<500^{-1}$ | $96,000^{-1}$ |
| mouse 9 | $<500^{-1}$ | $64,000^{-1}$ |

The mice immunized with the gp160-human IFNa preparation present IgG type antibody titers equivalent to those of mice immunized with the human IFNa only.

The neutralizing activity of such antibodies has been measured with the help of the human IFNa biological activity test described in the former example. Results are given in neutralization %.

TABLE 5

|  |  | 1/100 | 1/200 | 1/400 | 1/800 |
|---|---|---|---|---|---|
| Mice immunized with the IFNα: | | | | | |
| mouse 4 | D-2 | 0 | 0 | 0 | 0 |
|  | D72 | 100 | 80 | 70 | 53 |
| mouse 5 | D-2 | 0 | 0 | 0 | 0 |
|  | D72 | 100 | 70 | 65 | 50 |
| mouse 6 | D-2 | 0 | 0 | 0 | 0 |
|  | D72 | 100 | 65 | 60 | 57 |
| Mice immunized with the gp160-IFNα conjugate: | | | | | |
| mouse 7 | D-2 | 0 | 0 | 0 | 0 |
|  | D72 | 100 | 100 | 100 | 100 |
| mouse 8 | D-2 | 0 | 0 | 0 | 0 |
|  | D72 | 100 | 100 | 100 | 100 |
| mouse 9 | D-2 | 0 | 0 | 0 | 0 |
|  | D72 | 100 | 100 | 100 | 100 |

The antibodies induced by the complex have a higher neutralizing power than that induced by the human IFNα.

Example 30

Immunogenic Activity of the gp160-Toxoid Tat Heterocomplex

A. Material and Methods

The immunogenic (humoral and cellular) activity of the gp160-toxoid Tat preparation compared to that of the toxoid Tat was studied in 18 to 20 g BALB c mouse.

1—Immunization

At days 0, 7, 14, 21, a group of 3 mice receives a 0.1 ml (10 μg) injection of an AIF emulsion through the intramuscular route. A 5 μg booster injection in AIF is given at D-2.

A blood sample at the retro-orbital level is taken from each mouse before the first injection at d-2.

3 control mice receive the same preparations without an immunogen.

The mice are sacrificed 12 days after the last immunization.

2—Toxicity

The abnormal toxicity is sought in 3 mice receiving one human dose (100 μg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results:

1—Lack of Toxicity of the Heterocomplex in Vivo and in Vitro

The mice immunized both with the gp160-toxoid Tat preparation and the toxoid Tat only do not show any clinical sign and no anatomic wound. The immunosuppression test shows that doses of 100 ng/ml to 1 μg/ml of gp160-toxoid Tat do not reduce the proliferation of lymphocytes.

None of the three mice immunized with 100 μg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the Tat, determined by ELISA and expressed in titer (reciprocal of the dilution giving an optical density higher than 0.3). Table 6 shows the resulting antibody titers.

TABLE 6

| | Titer | |
|---|---|---|
| | D-2 | D72 |
| Control mice: | | |
| Control mouse 1 | <500⁻¹ | <500⁻¹ |
| Control mouse 2 | <500⁻¹ | <500⁻¹ |
| Control mouse 3 | <500⁻¹ | <500⁻¹ |
| Mice immunized with toxoid Tat: | | |
| mouse 4 | <500⁻¹ | 48,000⁻¹ |
| mouse 5 | <500⁻¹ | 64,000⁻¹ |
| mouse 6 | <500⁻¹ | 48,000⁻¹ |
| Mice immunized with gp160-toxoid Tat conjugate: | | |
| mouse 7 | <500⁻¹ | 64,000⁻¹ |
| mouse 8 | <500⁻¹ | 128,000⁻¹ |
| mouse 9 | <500⁻¹ | 64,000⁻¹ |

The mice immunized with the gp160-toxoid Tat preparation show higher antibody titers of the anti-Tat IgG type than those of mice immunized with the toxoid Tat only.

The neutralizing activity of such antibodies was measured by means of the Cat assay. Different dilutions of sera (1/100-1/800) taken at D-2 and D72 are incubated for 2 hours with 50 ng/ml of native Tat. Such dilutions are then deposited on HeLa cells, stably infected cells with a plasmid containing LTR of the VIH-1 as the promotor of the Chloramphenicol Acetyl transferase gene (CAT). After 24 hours of culture, the cells are lysed and the amount of CAT protein produced is measured by an ELISA test, the Cat assay (Boehringer Mannheim). Neutralizing sera prevent the Tat protein from inducing the expression of the CAT protein, while the non-neutralizing sera allow for the synthesis of such CAT protein. The results are expressed in neutralization %.

TABLE 7

| | | 1/100 | 1/200 | 1/400 | 1/800 |
|---|---|---|---|---|---|
| Mice immunized with toxoid Tat: | | | | | |
| mouse 4 | D-2 | 0 | 0 | 0 | 0 |
| | D72 | 60 | 50 | 25 | 20 |
| mouse 5 | D-2 | 0 | 0 | 0 | 0 |
| | D72 | 60 | 55 | 30 | 20 |
| mouse 6 | D-2 | 0 | 0 | 0 | 0 |
| | D72 | 65 | 50 | 30 | 30 |
| Mice immunized with gp16-toxoid Tat conjugate: | | | | | |
| mouse 7 | D-2 | 0 | 0 | 0 | 0 |
| | D72 | 100 | 100 | 100 | 100 |
| mouse 8 | D-2 | 0 | 0 | 0 | 0 |
| | D72 | 100 | 100 | 100 | 100 |
| mouse 9 | D-2 | 0 | 0 | 0 | 0 |
| | D72 | 100 | 100 | 100 | 100 |

The antibodies induced by the gp160-toxoid Tax conjugate have a higher neutralizing power than that induced by the toxoid Tat 2. Production of MIP1α

The production of MIP1α in culture supernatants of splenocytes. Splenocytes of immunized mice and control mice are isolated then cultivated in round bottom wells of a microculture plate at a level of 100,000 cells/well in the presence of 5 Mg/ml of p24, gp160, native Tat and a mixture of 5 μg/ml gp160 and 5 μg/ml of native Tat. The supernatants are taken after 24 hours of culture and the presence of MIP1 in the supernatants is measured by means of a R&D ELISA test. The results are expressed in μg/ml.

TABLE 8

| | | Gp160 | native Tat | Gp160 + native Tat | P24 |
|---|---|---|---|---|---|
| Control mice: | | | | | |
| mouse 1 D72 | MIP1α | 95 | 90 | 145 | 9 |
| mouse 2 D72 | Mip1α | 100 | 90 | 136 | 7 |
| mouse 3 D72 | MIP1α | 120 | 110 | 132 | 9 |
| Mice immunized with toxoid Tat: | | | | | |
| mouse 4 D72 | MIP1α | 145 | 130 | 190 | 7 |
| mouse 5 D72 | MIP1α | 128 | 145 | 225 | 9 |
| mouse 6 D72 | MIP1α | 150 | 230 | 295 | 10 |
| Mice immunized with gp160-toxoid Tat conjugate: | | | | | |
| mouse 7 D72 | MIP1α | 875 | 736 | 1725 | 9 |
| mouse 8 D72 | MIP1αα | 945 | 905 | 1900 | 7 |
| mouse 9 D72 | MIP1α | 1025 | 795 | 1755 | 8 |

Splenocytes of mice immunized with the gp160-toxoid Tat conjugate produce more MIP1α chemiokins than cells of mice immunized by the toxoid Tat only when they are activated, in vitro, by the immunogens used during the immunization.

4. Proliferation of Splenocytes of Immunized Mice (CMI test)

Splenocytes of immunized mice and of control mice are isolated then cultivated in round bottom wells of a microculture plate at a level of 100,000 cells/well in the presence of p24, gp160, native Tat and a mixture of gp160 and native Tat. The cell culture is continued at 37° C. in a humid atmosphere loaded with 5% of CO2 for 6 days. 18 hours before the end of the incubation, 0.5 μCi of titered thymidine/well were added. The intensity of the immune response is proportional to the proliferation index Ip.

Ip=spm (strokes per minute) for the given antigen/control spm

TABLE 9

|  | Gp160 | native Tat | Gp160 + native Tat | P24 |
|---|---|---|---|---|
| Control mice: | | | | |
| mouse 1 D72 | 1.1 | 1.1 | 1 | 1.2 |
| mouse 2 D72 | 1 | 1.1 | 1.1 | 1.1 |
| mouse 3 D72 | 1.2 | 1 | 1 | 1.1 |
| Mice immunized with toxoid Tat: | | | | |
| mouse 4 D72 | 1.2 | 8 | 10 | 1.1 |
| mouse 5 D72 | 1 | 9 | 9 | 1.2 |
| mouse 6 D72 | 1 | 10 | 9 | 1.2 |
| Mice immunized with gp160-toxoid Tat conjugate: | | | | |
| mouse 7 D72 | 9 | 11 | 8 | 1 |
| mouse 8 D72 | 10 | 9 | 7.5 | 1 |
| mouse 9 D72 | 10.5 | 9 | 8 | 1 |

Splenocytes of mice immunized with the gp160-toxoid Tat conjugate or the toxoid Tat, proliferate, when they are activated, in vitro, with the immunogens used during the immunization.

Example 31

Immunogenic Activity of the gp160-GMTat Heterocomplex

A. Material and Methods

The immunogenic (humoral and cellular) activity of the gp160-GM Tat preparation compared to that of the toxoid Tat was studied in 18 to 20 g BALB c mouse.

1—Immunization

At days 0, 7, 14, 21, a group of 3 mice receives a 0.1 ml (10 μg) injection of an emulsion in AIF through the intramuscular route. A 5 μg booster injection in AIF is given at D-2.

A blood sample at the retro-orbital level is taken from each mouse before the first injection at d-2.

3 control mice receive the same preparations without an immunogen.

The mice are sacrificed 12 days after the last immunization.

2—Toxicity

The abnormal toxicity is sought in 3 mice receiving one human dose (100 μg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

Lack of Toxicity of the Heterocomplex in Vivo and in Vitro

The mice immunized both with the gp160-GM Tat preparation and the toxoid Tat only, do not show any clinical sign and no anatomic wound. The immunosuppression test shows that doses of 100 ng/ml to 1 μg/ml of gp160-toxoid Tat do not reduce the proliferation of lymphocytes.

None of the three mice immunized with 100 μg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the Tat, determined by ELISA and expressed in titer (reciprocal of the dilution giving an optical density higher than 0.3). Table 10 shows the resulting antibody titers.

TABLE 10

|  | Titer | |
|---|---|---|
|  | D-2 | D72 |
| Control mice: | | |
| Control mouse 1 | $<500^{-1}$ | $<500^{-1}$ |
| Control mouse 2 | $<500^{-1}$ | $<500^{-1}$ |
| Control mouse 3 | $<500^{-1}$ | $<500^{-1}$ |
| Mice immunized with GM Tat: | | |
| mouse 4 | $<500^{-1}$ | $64,000^{-1}$ |
| mouse 5 | $<500^{-1}$ | $64,000^{-1}$ |
| mouse 6 | $<500^{-1}$ | $48,000^{-1}$ |
| Mice immunized with the gp160-GM Tat conjugate: | | |
| mouse 7 | $<500^{-1}$ | $128,000^{-1}$ |
| mouse 8 | $<500^{-1}$ | $128,000^{-1}$ |
| mouse 9 | $<500^{-1}$ | $64,000^{-1}$ |

The mice immunized with the gp160-GM Tat preparation show higher antibody titers of the anti-Tat IgG type than those of mice immunized with the GM Tat only.

Example 32

Immunogenic Activity of the KLH-Murine TNFα Heterocomplex

A. Material and Methods

The immunogenic (humoral) activity of the KLH-murine TNFα preparation compared to that of the murine TNFα was studied in 18 to 20 g BALB/c mouse.

At day 0, a group of 3 mice (group A) receives a 0.1 ml injection of an AIF emulsion through the intramuscular route containing 60 μg of the KLH-TNFa complex. A booster injection of 30 μg and 15 μg in AIF is given respectively at D21 and D60. 3 control mice receive a dose equivalent in murine TNFα according to the same protocol. (group B)

At day 0, a group of 3 mice (group C) receives a 0.1 ml injection in AIF through intramuscular route containing 60 μg of KLH-murine TNFα heterocomplex and 30 μg of the phosphorothioate oligodeoxynucleotide 5'-TCCATGACGTTC-CTGACGTT-3' (CpG ADN: 1826). A booster injection of 30 μg and of 15 μg of the KKL-murine TNFa heterocomplex in AIF is given respectively at D21 and D60. 3 control mice receive a dose equivalent in murine TNFα according to the same protocol. (group D)

A blood sample at the retro-orbital level is taken from each mouse before the first injection at d-2.

The mice are sacrificed 12 days after the last immunization.

2—Toxicity

The abnormal toxicity is sought in 3 mice receiving one human dose (50 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

Lack of Toxicity of the Heterocomplex in Vivo and in Vitro

The mice both immunized with the murine KLH-TNFα preparation and the murine TNFa only do not show any clinical sign and no anatomic wound. The immunosuppression test shows that doses of 100 ng/ml to 1 µg/ml of KLH-murine TFNα do not reduce the proliferation of lymphocytes.

None of the three mice immunized with 50 µg of the heterocomplex with or without the DNA CPG 1826 show any sign of toxicity (temperature, cutaneous disorders, systemic or regional signs) during the 7 days following the injection.

2—Humoral Response

The humoral response is measured by the presence in the serum of antibodies of the IgG type raised against the murine TNFα, determined by ELISA and expressed in titer. The presence of antibodies of the IgA type directed against the murine TNFa in vaginal secretions was also determined by ELISA and expressed in titer. The titer represents the opposite of the dilution giving an optical density higher than 0.3. The following table shows the resulting antibody titers.

TABLE 11

|   | D-2 | D72 | Vaginal IgA D-2 | D72 |
|---|---|---|---|---|
| Mice immunized with KLH-murine TNFα (group A) | | | | |
| 1 | $<500^{-1}$ | $64,000^{-1}$ | $<10^{-1}$ | $20^{-1}$ |
| 2 | | $48,000^{-1}$ | | $20^{-1}$ |
| 3 | | $64,000^{-1}$ | | $40^{-1}$ |
| Mice immunized with the Murine TNFα (group B) | | | | |
| 4 | $<500^{-1}$ | $750^{-1}$ | $<10^{-1}$ | $10^{-1}$ |
| 5 | | $1,000^{-1}$ | | $20^{-1}$ |
| 6 | | $750^{-1}$ | | $10^{-1}$ |
| Mice immunized with KLH-murine TNFα in the presence of CPG (group C) | | | | |
| 7 | $<500^{-1}$ | $128,000^{-1}$ | $<10^{-1}$ | $160^{-1}$ |
| 8 | | $256,000^{-1}$ | | $80^{-1}$ |
| 9 | | $256,000^{-1}$ | | $320^{-1}$ |
| Mice immunized with murine TNFα: in the presence of CpG (group D) | | | | |
| 7 | $<500^{-1}$ | $2000^{-1}$ | $<10^{-1}$ | $20^{-1}$ |
| 8 | | $4,000^{-1}$ | | $40^{-1}$ |
| 9 | | $3,000^{-1}$ | | $40^{-1}$ |

Example 33

Immunogenic Activity of the Tat Peptide-$_h$IgE Heterocomplex

A. Material and Methods

The immunogenic (humoral) activity of the KLH-human IgE preparation compared to that of the human IgE was studied in 18 to 20 g BALB c mouse.

1—Immunization

At days 0, 7, 14, 21, a group of 3 mice receives a 0.1 ml (10 µg) injection of an AIF emulsion through the intramuscular route. A 5 µg booster injection in AIF is given at D60.

A blood sample at the retro-orbital level is taken from each mouse before the first injection at D-2.

3 control mice receive the same preparations without an immunogen.

The mice are sacrificed 12 days after the last immunization.

2—Toxicity

The abnormal toxicity is sought in 3 mice receiving one human dose (50 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

2—Lack of Toxicity of the Heterocomplex in Vivo and in Vitro

The mice both immunized with the KLH-human IgE preparation and the human IgE only, do not show any clinical sign and no anatomic wound. The immunosupression test shows that doses of 100 ng/ml to 1 µg/ml of KLH-human IgE do not reduce the proliferation of lymphocytes.

None of the three mice immunized with 50 µg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the human IgE, determined by ELISA and expressed in titer (reciprocal of the dilution giving an optical density higher than 0.3). The following table shows the resulting antibody titers.

TABLE 12

|   | D-2 | D72 |
|---|---|---|
| Control mice: | | |
| 1 | $<500^{-1}$ | $<500^{-1}$ |
| 2 | | |
| 3 | | |
| Mice immunized with $_h$IgE | | |
| 4 | $<500^{-1}$ | $64,000^{-1}$ |
| 5 | | $128,000^{-1}$ |
| 6 | | $128,000^{-1}$ |
| Mice immunized with KLH-$_h$IgE: | | |
| 7 | $<500^{-1}$ | $256,000^{-1}$ |
| 8 | | $128,000^{-1}$ |
| 9 | | $256,000^{-1}$ |

The mice immunized with the KHL-$_h$IgF preparation show antibody titers of the IgG type slightly higher than those of mice immunized with the higE preparation only.

Example 34

Immunogenic Activity of the KLH-Ricin-β Heterocomplex

A. Material and Methods

The immunogenic (humoral) activity of the KLH-Ricin-β preparation compared to that of the ricin β fragment was studied in 18 to 20 g BALB/c mouse.

1—Immunization

At days 0, 7, 14, 21, a group of 3 mice receives a 0.1 ml (10 μg) injection of an AIF emulsion through the intramuscular route. A 5 μg booster injection in AIF is given at D60.

A blood sample at the retro-orbital level is taken from each mouse before the first injection at D-2.

3 control mice receive the same preparations without an immunogen.

The mice are sacrificed 12 days after the last immunization.

2—Toxicity

The abnormal toxicity is sought in 3 mice receiving one human dose (50 μg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

3—Lack of Toxicity of the Heterocomplex in Vivo and in Vitro

The mice both immunized with the human KLH-Ricin-preparation and the ricin β-fragment only do not show any clinical sign and no anatomic wound. The immunosuppression test shows that doses of 100 ng/ml to 1 μg/ml of KLH-ricin β do not reduce the proliferation of lymphocytes.

None of the three mice immunized with 50 μg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the β fragment of ricin, determined by ELISA and expressed in titer (reciprocal of the dilution giving an optical density higher than 0.3). The following table shows the resulting antibody titers.

TABLE 13

| | Titer | |
|---|---|---|
| | D-2 | D72 |
| Control mice: | | |
| 1 | $<500^{-1}$ | $<500^{-1}$ |
| 2 | | |
| 3 | | |
| Mice immunized with ricin-β | | |
| 4 | $<500^{-1}$ | $256,000^{-1}$ |
| 5 | | $512,000^{-1}$ |
| 6 | | $256,000^{-1}$ |
| Mice immunized with KLH-Ricin-β | | |
| 7 | $<500^{-1}$ | $256,000^{-1}$ |
| 8 | | $256,000^{-1}$ |
| 9 | | $128,000^{-1}$ |

The neutralizing activity of such antibodies was checked by the injection f mixtures of anti-Ricin-β and ricin serum which did not cause the animal's y to what was observed during the administration to the mouse of ricin and mixtures.

Example 35

Method of Manufacturing a Stable Immunogenic Product According to the Invention

A. Materials

TABLE 14

Chemicals and Reagents

| Reagent | Grade | Supplier | Details | Application |
|---|---|---|---|---|
| Glutaraldehyde 25% | Grade 1 | Sigma | G5882 10 × 1 mL | PD & GMP |
| Formaldehyde 37% | — | Sigma | F-1635 25 mL | PD |
| Formaldehyde 37% | EP | Sigma | 15513 | GMP |
| Di-sodium hydrogen phosphate (anhydrous) | Analar | BDH | 10249 | PD |
| Di-sodium hydrogen phosphate (anhydrous) | USP | Merck | 1.06585 5 kg | GMP |
| EDTA | Analar | BDH | 10093 | PD |
| EDTA | USP | Merck | 108421 1 kg | GMP |
| Glycine | Analar | BDH | 10119 | PD |
| Glycine | USP | Merck | 500190 1 kg | GMP |
| Sodium chloride | Analar | BDH | 10241 | PD |
| Sodium chloride | BP | Merck | 116224 | GMP |
| DMSO | 99.5% | Sigma | D5879 | PD |
| DMSO | USP | Sigma | D2438 10 mL | GMP |
| DPBS | — | Sigma | D8537 | PD |
| DPBS | tbc | tbc | tbc | GMP |

TABLE 15

Consumables

| Description | Supplier | Application |
|---|---|---|
| Slide-a-Lyzer ® cassettes 7 kDa MWCO (0.5-3 mL) | Perbio; 66370 | Dialysis |
| Pellicon XL PES membranes (5 or 10 kDa MWCO) | Millipore; PXB010A50 | Tangential flow filtration |
| 50 mL tubes | Nunc; 362696 | Sample container |
| Wide mouth polypropylene bottle (150 mL) | VWR; 215-0520 | Sample container |
| Wide mouth polypropylene bottle (250 mL) | VWR; 215-5683 | Sample container |
| Cryovials (3.5 mL & 2 mL) | Sigma; V1138; V9637 | Sample container |
| Labscale TFF unit with 500 mL acrylic reservoir | Millipore; XX42LSS13 | Tangential flow filtration |

B. Description of the Method

Step a)

Take 30.05 mL of TNFa (at 4.2 mg/ml) and allow to thaw at 4° C. overnight (NB: 126.21 mg of TNFa required).

Step b) (or step b1) in Certain Embodiments of the Method)

Add 90.15 mL of "dilution buffer" to obtain the "working buffer" solution and TNFa at 1 mg/mL (±10%).

Dilution buffer=130 mM di-sodium hydrogen phosphate, 133 mM NaCl, 6.6 mM EDTA, pH 7.8.

Working buffer=100 mM di-sodium hydrogen phosphate, 150 mM NaCl, 5 mM EDTA, pH 7.8.

Step b2)

To the remaining 120 mL of the TNFa at 1 mg/mL (±10%) and add 1.2 mL of DMSO. Hold the mixture at RT for 30 minutes. Mix by agitation every 10 minutes and attempt to avoid foam formation.

Add 61.34 mL of "working buffer" to the mixture. Mix gently by inverting the container and attempt to avoid foam formation.

Step c)

Add 51.6 mg of KLH. Note: for a 9.81 mg/mL solution of KLH add 5.26 mL. Mix gently by inverting the container. The total volume at this point is 187.8 mL.

Step d)

Dilute the 25% stock of glutaraldehyde to 2.5% using the "working buffer". This is done immediately prior to use.

Add 20.86 mL of the diluted 2.5% solution of glutaraldehyde. Note that the total volume at this point is 208.56 mL. Mix gently by inverting the container.

Close the bottle and incubate for 45 min at RT. Gentle turn the bottle over every 15 min.

Step e)

Diafilter the solution using TFF against the working buffer dialysis three times against 20 volumes of phosphate buffer at pH 7.6 10 mM, 150 mM NaCl.

Volume 1=2 hours
Volume 2=2 hours
Volume 3=overnight

Step f)

Dilute stock solution of formaldehyde (at 37%) 10-fold with "working buffer" to give a 3.7% solution. This is done immediately prior to use.

Add diluted 3.7% formaldehyde to the TNFa-KLH solution to give a final concentration of 0.2%.

For example, if the volume recovered is 200 mL, then the amount of 3.7% formaldehyde to be added will be 11.43 mL).

Seal the bottle and incubate for 6 days at 37° C. The bottle is overturned once a day.

Step g)—Addition of Glycine

After the 6 days, add 2M glycine (made up in WFI) to a final concentration of 0.1M). Incubate for 1 hr at room temperature during which time period the bottle is gently overturned.

Step h)

Check the pH of the DPBS (Sigma) to be used for diafiltration and adjust if required to a final pH of 7.3±0.2 using 0.1M NaOH. No need for pH adjustment is normally expected.

Diafilter the solution using TFF against DPBS.

2×5 kDa MWCO TFF membranes will be used

A 500 mL (acrylic) reservoir on the Labscale TFF system will be used.

Material is recovered from the membrane by draining the concentrate (ultrafiltration retentate) into a pre-weight polypropylene bottle.

The process disclosed in this example illustrates an embodiment of the method according to the invention for manufacturing a stable immunogenic product comprising antigenic heterocomplexes of TNFa and KLH.

Further, the method which is detailed hereunder is designed for manufacturing a batch of 120 mg of the stable immunogenic product.

Example 36

Test Procedures for the Stable Immunogenic Product Obtained by the Method According to the Invention The test procedures disclosed in Example 36 may be referred to by one skilled in the art. However, the one skilled in the art may also perform test procedures according to any one of the test procedures that are disclosed in the examples 37 to 40 herein.

2.1. Total Protein Content Determination by Colorimetry: Example of the Bradford Test The protein content is determined using the Bradford technique (Bradford, M. Anal. Biochem. 1976.72, 248-254).

Briefly, a calibration curve is established with bovine serum albumin (BSA) by pipetting in a series of test tubes 0, 10, 20, 30, 40 µL of a 0.2 mg/mL BSA solution in PBS. Subsequently, the volume of each tube is completed to 500 µL by adding the corresponding volume of DI water. To each tube is then added 500 µL of Bradford reagent. Two blanks are prepared with 200 µL PBS. After 5 min. reaction at room temperature, the content of each tube is vortexed and read at 595 nm.

Two hundred µL of an appropriate dilution of the test protein solution are reacted with the Bradford reagent as described above.

TNFa Protein Content in KLH-TNFa: ELISA

Four samples of KLH-TNFa taken from 4 vials are diluted in Phosphate Buffered Saline pH 7.2 (PBS) at 5 µg/mL. These dilutions are used for coating microtiter plates (Costar 3590), 100 µL per well. After allowing coating to occur overnight at 4° C., the plates are washed with PBS containing 0.1% Tween 20 and the wells are saturated with 2% Fetal Calf Serum (FCS) solution in 100 µL PBS-Tween for 2 hr at 37° C. After washing the plates with PBS-Tween, 100 µL of serial dilutions of an anti-TNFa serum are pipetted into each well and the plates are incubated for 2 hr at 37° C., after which they are thoroughly washed and again incubated for 2 hr at 37° C., after adding to each well 100 µL of a HRP-labeled anti-IgG antiserum.

Following incubation, the plates are washed and 100 µL of ortho-phenylenediamine (OPD) solution are added to each well. Three minutes later, 100 µL of 2N sulphuric acid are added to each well and the plates are read at 490 nm in a multiscan photometer.

2.2. Purity Grade of KLH-TNFa Immunogen: IEF+Western Blot

The purity grade of the immunogen is assessed by isoelectric focusing (IEF) by allowing the KLH-TNFa immunogen to migrate aside KLH alone and TNFa alone on a 1% agarose plate in a 3 to 10 pH gradient. After applying an appropriate dilution of each sample at 250 µg/mL, the migration is carried out using a Phast system apparatus (Amersham Pharmacia) under the following conditions:

1st step (pre-migration): 500 V, 2.5 mA, 2.5 W, 15° C., 5 aVh $2^{nd}$ step (application): 200 V, 2.5 mA, 2.5 W, 15° C., 5 aVh $3^{rd}$ step (migration): 1500 V, 2.5 mA, 2.5 W, 15° C., 450 aVh Following migration, the proteins are transferred by microcapillarity to a PVDF membrane and the proteins are revealed by Western Blot.

Western Blot Detection

The nitrocellulose membrane is saturated by dipping it overnight in 5% milk-TBS Tween 20 at room temperature, after which it is incubated for 1 hr with either the primary polyclonal anti-TNFa (hu) or anti-KLH antibody diluted in 10% milk-TBS Tween 20 at room temperature. Subsequently, the membrane is washed 4 times during 5 min with TBS-Tween 20 before being incubated for 1 hr with the secondary HRP-labeled antibody diluted with 10% milk-TBS Tween 20 at room temperature. Again, the membrane is washed 4 times with TBS-Tween 20 and the spots are revealed by chemoluminescence using an ECL Plus Kit (Amersham Pharmacia).

3. Percentage of CYT-KLH Covalent Bonds in a CYT Kinoid 3.1. Method No 1: Size Exclusion Chromatography in Denaturing and Reducing Conditions.

The test kinoid solution is submitted to denaturing (urea 8M final concentration) and reducing (beta-mercaptoethanol 5% final concentration) conditions that will lead to a dissociation of noncovalent bonds. The resulting solution is eluted through a size-exclusion column packed with Superdex 200™ (Pharmacia), chosen for its 200 kDa fraction limit, far below the molecular weight of KLH and covalent KLH-TNFa constructs. Only those cytokine molecules covalently linked to KLH will be present in the exclusion volume. The latter is assayed for TNFa (specific TNFa antigens) using a sandwich-ELISA technique with anti-TNFa Abs that have no cross-immune reaction with KLH. The result is expressed as a percentage of TNFa titer in the starting solution, which is measured by the same ELISA technique. This percentage is equal to the % TNFa-KLH covalent bonds in the TNFa kinoid.

3.2 Method No 2: Double-Sandwich ELISA with Tween Washing

A 1 mg/mL solution of anti-KLH polyclonal Abs in PBS (10 mM pH 7.3 NaCl 150 mM) is used for coating a microtiter plate (Costar, high-binding), 100 µL per well, for 2 hr at 37° C. After 3 washing cycles with PBST (PBS with Tween 20 0.1% v/v), the wells are saturated for 1 h30 with PBS containing 2% FCS. The wells are again washed 3 times with PBST.

Two identical series of dilutions of the test kinoid (10, 5, . . . , 0.156 µg/mL) are then added in the wells and incubated for 2 hr. The wells are washed 3 times with PBST, the dissociation action of which (via Tween 20) eliminates all molecules non-covalently bound to KLH, the latter KLH being fixed to the support-coated capture Abs. The first series of test dilutions is incubated with anti-KLH Abs while the second series is incubated with anti-TNFa Abs. After incubating for 1 h30 at 37° C., wells are washed as described above, then incubated with specific peroxidase-coupled secondary Abs.

The addition of OPD, the peroxidase substrate, allows a quantitative calorimetric detection of the fixed anti-TNFa Abs, for the first series, and fixed anti-KLH Abs, for the second series. The ratio of fixed Abs between the two series gives the percentage of TNFa covalently bound to KLH in the kinoid.

4. Immunological Activity of KLH-TNFa Kinoids

Antigenicity Test: ELISA

This test is intended for measuring the capacity of an immunogen (either an antigen derivative, or an antigen bound to a carrier protein) to combine with a specific antibody with respect to that of the native antigen. This test essentially consists in a reverse ELISA.

A series of increasing dilutions of the immunogen under test are distributed into wells of a polystyrene microtiter plate. A specific polyclonal antibody directed to the protein to be tested is allowed to react with the immunogen immobilized in the wells. After removing the excess of antibody unreacted by washing the plate, the Ab immobilized by the immunogen in the wells is quantitatively revealed by having it reacted with a HRP-labeled Ab directed to the first Ab, the yellow color that develops by adding an appropriate substrate is directly proportional to the amount of immobilized protein. The optical density (OD) of each well is measured with an absorbance microplate reader. The protein content in the test sample is determined from a calibration curve.

5. Immunogenicity of Kinoids

The immunogenicity of an immunogenic preparation is:
1—its capacity level to induce the formation of specific anti-TNFa polyclonal Abs (measured in vivo); and
2—the neutralization capacity thereof. The latter is measured in vitro by quantifying the capacity of the antiserum, sampled from the immunized mice, to inhibit the specific biological activity of TNFa
1—For this, groups of 20 7-week-old BALB/c mice, 18-20 g body weight, housed in separate cages of 5 animals, fed with standard diet in pellets with food and water ad libitum are immunized on day 0, 7, 14 and 21 by intramuscular administration of 0.1 mL (10 µg) of the test immunogen in ISA 51 (1:1 v/v emulsion in ISA 51). A booster injection of 5 µg of the immunogen is given as 0.1 ml of a 1:1 emulsion in ISA 51 on day 60. A blood sample is taken 2 days before initiating the immunization by retro-orbital puncture and again 12 days after the last injection for antibody level determination by ELISA. Three control mice receive a 1:1 v/v emulsion of PBS in IFA.

Serum Ab titers are expressed as the inverse of the dilution that gives an OD>0.3.

2—Neutralization capacity: [ACOMPLETER]

The results show the high neutralizing capacity of the sera antibodies of mice immunized with a stable immunogenic product of the invention comprising TNFa and KLH.

6. Immunotoxicity—In Vitro

Test of proliferation (by incorporation of 3H-thymidine) of T cells stimulated by PPD/TT antigens and treated with various kinoid doses.

PBMC's are freshly isolated from healthy donors by blood separation by Ficoll gradient centrifugation. Cells are introduced in round-bottom 96-well plates, 15,000 cells/well in RPMIc medium with 10% FCS. The kinoid is added at concentration 1 µg/mL to 100 ng/mL, then PPD or TT at 0.16%. Plates are allowed to incubate at 37° C. 5% CO2 for 6 days. Tritiated thymidine is added 18 hr prior to incubation end, 0.5 µCi/well. Cell proliferation is analyzed with a β scintillation counter.

7. Biological Characteristics of KLH-TNFa Kinoids

TNF-α Bio-Assay:

Cytolysis of Murine L929 Cells in the Presence of Actinomycin D

Materials

L929 mouse fibroblast line (ATCC Cat. No. CCL-1) KLH-TNFα (murine or human) kinoid in PBS (standard), NEOVACS Recombinant murine TNFα Peprotech (315-01A) or human TNFα Peprotech (300-01A) Culture Medium (RPMI supplemented with 10% FCS (Foetal Calf Serum) 2 mM glutamine, 100 U/ml penicillin-streptomycin Assay Medium (RPMI supplemented with 2% FCS 2 mM glutamine, 100 U/ml penicillin-streptomycin)

Pre-incubation medium: HL1 supplemented with 2 mM glutamine, 100 U/ml penicillin-streptomycin 96-well flat-bottom culture plate (Costar, 3595)

Actinomycin D, 1000 µg/mL stored at 4° C. (protected from light)

MTT solution (Sigma, M5655) 5 mg/mL stock in PBS stock aliquot kept at minus −20° C. (protected from light)

DMSO (SIGMA, 471267)

Experiment Duration 24-hour incubation 1 hour assay preparation

Method

1. Dilute KLH-TNFα murine or human kinoid and standard in a series of two-fold dilutions in the Assay Medium in 50 μL/well in 96-wells plate from row 2 to 11, starting at thr proper dilution Leave row 1 as blank.
2. Prepare L929 cell suspension at a density of 7.5 105/mL in Assay Medium supplemented with actinomycin D at 1 μg/mL (protected from light). Add 50 μl/well of the cell suspension to the same plate, from row 1 to 12.
3. Incubate plate for 24 h at 37° C. 5% CO2 in a humidified incubator.
4. Rinse 2 times with PBS without Ca2+ Mg2+
5. Add 50 μl/well MTT solution at 40% in Assay Medium and incubate for 4 hours at 37° C. 5% CO2 in a humidified incubator.
6. Empty plates and add 50 μL of DMSO to each well.
7. Read plate at 550-630 nm
8. Analyze data Example 37

Comparative Study of the Various Preparation of KLH-TNFα (Human) Kinoids

Various preparation of a human TNF-α kinoid consisting of human TNF-α complexed to the specific carrier protein KLH have been performed.

More precisely, various preparations of KLH-TNFα (human) have been produced by the same general process that is disclosed in example 35 but with variations in (i) the percentage of DMSO, (ii) glutaraldehyde concentration (2.5 or 22.5 mM) as well as (iii) the time period of incubation of the intermediate product with formaldehyde (from 0.2 to 6 days incubation time period).

Then, the loss of the biological activity of the human TNF-α has been assayed. Also, the preservation of the conformational B-epitopes in the final kinoid product has been tested through (i) the cytotoxicity assay of human TNFα on the L929 cell line, as well as (ii) through the immunogenicity assays disclosed herein in this example.

A. Materials and Methods

A.1 Assays for the Absence of TNFα Biological Activity in the KLH-TNFα (Human) Kinoids.

Human TNFα, in the presence of D actinomycin, possesses a cytotoxic activity on the murine fibroblast cells of the L929 cell line, which cytotoxic activity is assessed by the cell viability test using MTT(3-[4,5-dimethylthiazol-2-yl]-2,5-diphenyl-tetrazolium bromide. This assay is based on the MTT reduction by the mitochondrial NADPH reductase of the living cells towards the reduced product formazan which has a purple-blue color.

In this assay, the metabolic activity of the cells allows the evaluation of their viability.

The assessment of the biological activity of the KLH TNF-α kinoid consists of incubating the L929 cells in the presence of decreasing amounts of said kinoid product (50 ng/ml to 0 ng/ml) in combination with D actynomycin (1 μg/ml) in flat-bottomed wells of a microculture plate.

The cell culture is then performed at 37° C. in a wet atmosphere containing 5% CO2 during a time period of 24 hours.

After a 24 hours culture time period, the cell culture supernatants are discarded and replaced by the MTT assay solution.

After 4 hours time period incubation at 37° C. with MTT, MTT solution is removed and DMSO is added.

After homogenization, the optical density of the cell culture supernatant is analyzed with a spectrophotometer at a wavelength of 570 nm.

The results are expressed as optical density (O.D.) at 570 nm. In parallel, cell cultures incubated with a range of TNFα from 0 to 10 ng/ml is performed, as a control.

The final results are expressed as lethal dose 50, also termed LD50, which is the dose that induces the lysis of 50% of the cultured L929 cells.

A.2 Assay for the Preservation of the Conformational B-Epitopes of Human TNFα in the Final KLH-TNFα (Human) Kinoid, After the Chemical Treatments with Glutaraldehyde and Formaldehyde: Immunogenicity Assay.

The study of the preservation of the conformational of B epitopes of the human TNFα in the final KLH-TNFα (human) kinoid, after the chemical treatments, is performed by a test of the immunogenic activity in C57Bl/6 weighing 18-20 g.

At Day 0, a group of tree mice is injected with 0.2 ml (50 μg) of an emulsion in Complete Freund Adjuvant (CFA) by the intramuscular route.

A second injection of 25 μg of the kinoid product in incomplete Freund adjuvant is administered at Day 21.

Retro-orbital blood sampling is performed on each mouse before the first injection and also at Day 28. Sera from each group of mice are gathered.

The humoral response is measured through detection of IgG isotype antibodies directed against human-TNFα in the sera of the immunized mice. The humoral response is determined by an ELISA assay and is expressed in antibody titers (dilution-1 giving an optical density greater than 0.3).

The neutralizing capacity of the sera from mice immunized with the KLH-TNFα (human) kinoid has been measured through the TNFα cytotoxicity assay on L929 cells, as described hereafter.

L929 cells are treated with various dilutions from pools of sera (dilutions from 1/100 to 1/12800) that have been sampled at Day −2 and Day 28 and then have been incubated during 40 minutes at room temperature, and then 20 minutes at 4° C. with 20 ng/ml of human TNFα.

The cell culture is pursued at 37° C. in wet atmosphere, 5% CO2, during 24 hours.

After a 24 hours cell culture time period, the cell culture supernatants are removed and replaced by MTT solution.

After a 4-hour incubation at 37° C., MTT is removed and DMSO is added.

After homogenization, the optical density of the cell culture supernatant is analyzed with a spectrophotometer at the wavelength of 570 nm.

The results are expressed as optical density (O.D.) of the cell culture supernatants. A cell cultures incubated with a range of TNFα from 0 to 10 ng/ml is performed in parallel, as a control.

The sera that neutralize the cytotoxic activity of TNFα prevent to exert its cytotoxic activity on the L929 cells.

The results are expressed as the neutralizing capacity 50%, or NC50, which corresponds to the sera dilution that neutralizes 50% of the cytotoxic activity of the human TNFα.

B: Results

Table 16 hereunder discloses the results obtained with the final KLH TNFα (human) kinoid prepared according to various chemical treatments.

TABLE 16

| Code | Glutaraldehyde (mM) | Formaldehyde (day) | EDTA | DMSO (%) | LD$_{50}$ (ng/ml) | Antibody titer | NC$_{50}$ |
|---|---|---|---|---|---|---|---|
| K1 | 2.5 | 2 | 5 mM | 0 | 12.5 | >64000 | 1/650 |
| K2 | 2.5 | 2 | 5 mM | 2 | 20 | >64000 | 1/600 |
| K3 | 22.5 | 0 | 5 mM | 1 | 0.15 | >64000 | 1/600 |
| K4 | 22.5 | 2 | 5 mM | 1 | 200 | >64000 | 1/750 |
| K5 | 22.5 | 2 | 5 mM | 2 | 225 | >64000 | 1/400 |
| K6 | 22.5 | 2 | 5 mM | 5 | 250 | >64000 | 1/700 |
| K7 | 22.5 | 6 | 5 mM | 1 | >400 | >64000 | 1/1200 |
| K8 | 22.5 | 6 | 5 mM | 2 | >400 | >64000 | 1/300 |
| K9 | 22.5 | 6 | 5 mM | 5 | >400 | >64000 | 1/350 |
| K10 | 22.5 | 2 | 0 mM | 0 | 15 | >64000 | 1/700 |

As shown in Table 16 above, the best results are obtained with a process of manufacturing KLH TNFα (human) kinoid involving a chemical treatment (i) with DMSO at the concentration of 1% and (ii) with glutaraldehyde at the concentration of 22.5 mM, then (iii) with a chemical treatment with formaldehyde during the period of time of 6 days. The resulting final KLH-TNFα (human) product is devoid of the cytotoxicity activity of human TNFα and induces the production of polyclonal antibodies that neutralize the biological activity of the native human TNFα.

Thus, the manufacturing process according to the condition disclosed in K7 of table 16 above allows the inactivation of the human TNFα cytokine contained therein why preserving the conformational B-epitopes.

The KLH-TNFα (human) final product prepared according to the conditions named "k7" in Table 16 above is the same as the one which is manufactured according to example 35 above.

This best TNFα kinoid product is the one which has been studied in the following examples, notably in a transgenic mice model, in view of studying its ability to induce polyclonal antibodies that neutralize native TNFα in an autologous system.

Example 4

Study of the Acute Toxicity of the KLH-TNFα (Human) Kinoid in Mice

The goal of the study was to define the characteristic properties of a vaccine composition comprising a KLH-TNFα (human) kinoid according to the invention, to be used as a broad spectrum therapeutic vaccine for use in the treatment of cancerous cachexia and/or various auto-immune diseases (e.g. rheumatoid arthritis, Crohn's disease and psoriasis).

Particularly, the vaccine composition properties as regards tolerance and absence of risk have been studied.

Consequently, a first toxicity study has been performed in SWISS mice.

A. Material and Methods

Forty six (46) female SWISS mice have been distributed in (i) one group of four non-treated animals and (ii) three groups of fourteen animals that have received, respectively:

a) Control Group (Adjuvant Vehicle): n=14

An intramuscular route injection (IM) located in the thigh of phosphate buffer saline (PBS);

The control group was used to assess the local and systemic reactivity of the adjuvant use in the formulation.

b) Treated Group (First Dose: 2,000 Times the Single Therapeutic Human Dose, STHD°/N+14.

An intramuscular route injection (IM) located in the thigh of KLH-TNFα (human) kinoid at 50 µg/mouse in a phosphate buffer saline (PBS);

c) Treated Group (Second Dose: 4000 Times the Single Therapeutic Human Dose, STHD): n=14

An intramuscular root injection (IN) located in the thigh of the KLH-TNFα (human) kinoid at the dose of 100 µg/mouse in a phosphate buffer saline (PBS).

d) Group of Naïve Mice, Non-Treated, that were Included in this Study (n=4).

The computation of the dose concerns the single dose for human use, which is 80 µg/injection/individual: 1 SHTD (single therapeutic human dose), thus, 1.15 µg/kg.

The injections of the KLH-TNFα (human) kinoid have been performed at Day 5 (D 5) of the experimentation.

The response of animals to the treatment above has been tested according to the following parameters:

a—The eventual number of death, immediate, short time period and long time period (observation period of 10 days after administration).

b—Local or systemic reactivity to the treatment.

c—Curve showing the general status and the weight of the animals until 10 days following administration of the KLH-TNFα (human) kinoid (D 15).

Five (5) days after the observation period (D20), the surviving animals have been sacrificed and the following controls have been performed.

d—Microscopic anatomo-pathologic examination of the muscle at the location of the injection site, for evaluating the local tolerance.

d—Determination of the weight of lungs, heart, liver, and spleen, as an index value of the organ response to the administration of the immunostimulating substances.

B. Results

When administered to mice at highly elevated doses (about 4000 times the single human therapeutic dose in each mouse), the KLH-TNFα (human) kinoid has not led to any adverse effect, during the whole observation period of 10 days, and for each of the tested groups, as it is illustrated by:

1) No occurrence of an immediate or medium term death;

2) No local reaction at the site of injection, nor any systemic reaction;

3) No effect on the growth curves of the mice, in any of the tested groups.

Further, the macroscopic examination of the organs from the animals sacrificed at the end of the test (D20) has shown no organ alteration nor any increase in the volume from the spleen and the liver.

Further, the weight of the heart, the lungs, the liver and the spleen have varied in a similar manner for the whole groups of animals tested.

Example 5

Study of the Immunogenicity of the KLH-TNFα (Human) Kinoid in a Transgenic Mice Model Suited for Human TNF The immunogenic activity (humoral) of the KLH-TNFα kinoid preparation, as compared with the immunogenic activity of the KLH, has been studied in mice B6.SJL-Tg (TNF) N2 of 5 weeks (group of 10 mice). These mice have been provided by Taconic Company (USA) and consist of mice which are transgenic for the human TNFα gene (hemizygote).

A. Material and Methods

At Day 0 and at Day 7, mice (group of 10 mice) have received an injection of 0.2 ml (30 µg) of an emulsion in ISA51 by the intramuscular root. A second injection of 25 µg in ISA51 was given at Day 28. Then, a retro-orbital blood sampling is performed in each mouse at Day 35.

B. Results

1. Humoral Response

The humoral response is measured by the presence in the sera of the immunized mice of IgG type antibodies directed against human TNFα; The humoral response is determined by an ELISA assay and is expressed at the antibody titer (dilution-1 giving an optical density greater than 0.3). FIGS. 14A-14B illustrate the antibody titer that was obtained.

The sera from mice immunized with the KLH-TNFα (human) final product obtained according to example 35 possess high level of IgG type antibody titers, whereas the sera from mice immunized with KLH are devoid of these antibodies.

The neutralizing activity of these antibodies has been measured with the TNFα cytotoxicity assay on L929 cells. The results are presented in FIGS. 15A-15B.

The antibodies induced by the KLH-TNFα (human) kinoid preparation have a high level of neutralizing activity.

Example 6

Study of the Immunogenicity of the KLH-TNFα (Human) Kinoid in the Rhesus Macaque The humoral immunogenic activity of the KLH-TNFα (human) kinoid, as compared with the immunogenic activity of KLH alone, has been studied in rhesus macaque provided by MDS pharma (Lyon-France). It is to be noticed that the TNFα that is naturally produced by the macaque rhesus shares 98.1% amino acid homology with human TNFα.

A—Material and Methods

At Day 0, Day 21 and Day 49, macaques have received an injection of 0.5 ml of an emulsion of the kinoid in ISA51 by the intramuscular route, containing (i) either 80 or 20 µg of the KLH-TNFα (human) kinoid preparation, or (ii) KLH alone. A blood sampling has been performed on each animal at Day 28, Day 56, and Day 68.

B—Results

1—Humoral Response:

The humoral response has been measured by detecting the presence of IgG isotype antibodies directed against human TNFα in the sera of the immunized macaques. The humoral response has been determined with an ELISA assay and is expressed as antibody titers (dilution-1 giving an optical density greater than 0.3). The results of the antibody titers obtained are reported in FIGS. 16A-16C.

The sera from the macaques immunized with the KLH-TNFα (human) kinoid preparation have anti-TNFα IgG isotype antibody titers, whereas sera from the macaques immunized with KLH alone is devoid of these antibodies.

The anti-TNFα antibody titers are more important in the serum of the macaques that have received 80 µg of the KLH-TNFα (human) kinoid.

The neutralizing activities of the antibodies have been measured with the TNFα cytotoxicity assay on L929 cells. The results of these assays are reported in FIGS. 17A-17C.

The antibodies induced by the KLH-TNFα (human) have a very high neutralizing activity.

Example 7

Assessment of the Therapeutic Efficiency of the Active Immunization Against TNFα in huTNFα Transgenic Mice The assessment of the therapeutic efficiency of the active immunization strategy against TNFα using the KLH-TNFα (human) kinoid preparation as the active ingredient have been performed in transgenic mice huTNFα B6.SJL-Tg (TNF) N2 of 5 weeks old, provided by Taconic Company (USA). These TNFα transgenic mice develop a spontaneous polyarthritis at the age of 4 to 5 weeks.

A—Material and Methods

1—Immunization.

Mice have received one injection of 0.2 ml of an emulsion in ISA51 by the intramuscular route at days D0, D7, and D28. Four groups of 10 mice have been treated as detailed hereunder:

Group A: PBS: 200 µl PBS
Group B: KLH: 200 µl KLH
Group C: KLH-TNF: 200 µl KLH-TNF
Group D: KLH-TNF+MTX: 200 µl KLH:TNF and methotrexate (1 mg/kg) three times a week, starting from immunization No 1 and until sacrifice (intraperitoneal injection of 200 µl per injection).

Mice have received (i) at Day 0 and Day 7: 30 µg of the KLH-TNFα (human) kinoid preparation and (ii) at Day 28: 15 µg of the same preparation.

A retro-orbital blood sampling was performed on each mouse at Day 35. At Day 57, at the time the mice are sacrificed, a blood sampling has also been performed.

2—Clinical Examination and Quantitative Assessment of Arthritis:

A clinical examination has been performed, yet at the starting time of the experiment, and then twice a week.

The assessments were performed by an observer having no knowledge of the treatment that was applied. The clinical severity of arthritis at each joint (fingers, tarsus, ankle, carpe) was quantified by attribution of a score varying from 0 to 4 wherein: 0=normal; 1) erythema; 2=swelling; 3=deformation; and 4=major deformation or necrosis. A sum of these scores was performed in order to obtain an arthritis score for each animal, every day. A mean for each group was calculated for every day of treatment.

3—Histological Examination and Quantitative Evaluation of the Arthritis.

The animals were all sacrificed 57 days after the starting of the experiment. The posterior paws has been removed, fixed in formol, decalcified, then dehydrated and then included in paraffin blocks. Then, 5 µm thick histological slices were performed with a microtome. At least for serial sections were performed for each paw in order to ensure a correct spatial assessment of the joint affections. The slides preparations were then stained by hematoxylin and eosin and then observed under optical microscope. The lesions were quantitatively assessed on each section according to a three points scale (0=normal; 3=severe). This histological score may be divided into two parameters: destruction of the cartilage and of the bone (thickness of the cartilage and of the bone, irregularities and presence of erosions) on one hand, and on the other hand, inflammation (synovial proliferation, cell inflammatory infiltration).

4—Statistics:

The results values are given as mean and standard deviation from the mean (SDM). A student's t test as well as a variance analysis (ANOVA) have been performed.

B—Results:

1—Humoral Response:

The humoral response is measured by detecting the presence of IgG isotype antibodies directed against human TNFα in the sera of the immunized macaques. The humoral response is determined by an ELISA assay and the results are expressed as the antibody titer (dilution-1 giving an optical density greater than 0.3).

The results of the antibody titers that were obtained are reported in FIGS. 18A-18D.

2—Clinical Examination and Quantitative Assessment of the Arthritis. Evolution of the Clinical Score with Time.

Figure 19:
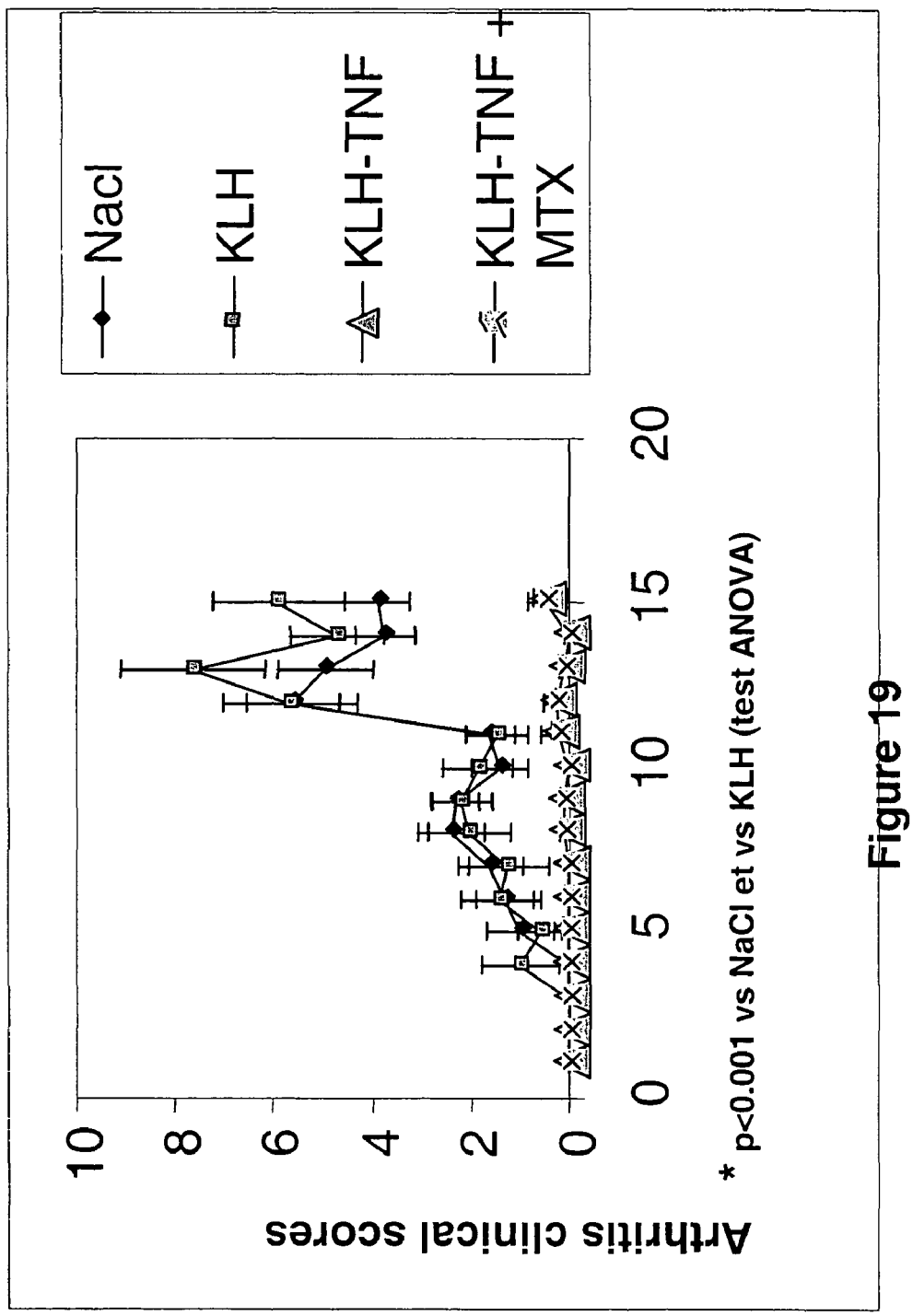
FIG. 19 illustrates the arthritis clinical scores determined in transgenic huTNFa B6.SJL-Tg(TNF) N2 injected with
  NaCl [♦];
  KLH alone [■];
  a stable immunogenic product manufactured as disclosed in Example 35 [▲]; and
  a stable immunogenic product manufactured as disclosed in Example 1 combined with methotrexate [■]
  Abscissa: Days after first injection; Ordinate: arthritis clinical scores.

The evolution of the clinical score with time is reported in FIG. 19.

Treatment of the macaques (i) with KLH-TNF (human) kinoid or (ii) with KLH-TNF (human) kinoid combined with MTX induces a major statistically significant decrease of the arthritis scores that were assessed by clinical examination. By comparison, the arthritis scores determined for the control animals treated with KLH or with PBS buffer were far lower.

Assessment of the Disease Occurrence and Severity Occurrence Parameters

The assessment of the disease occurrence and disease severity is reported in table 4 hereunder.

The day of occurrence of the disease has been determined, for each animal, through a clinical examination. The animals that had never developed the disease were not taken into account The score "A MAX" corresponds to the maximal score reached by each animal during the experiment. The score "A MAX" represents a parameter of disease severity.

The incidence means the number of animals having developed arthritis before the end oft the experiment, it being taken into account the total number of animals in each group.

TABLE 17

| Treatment | Day of disease occurrence (sick animals only) | Amax Scores ± sted dev. | Incidence |
|---|---|---|---|
| PBS | 24.4 ± 2.5 | 11.5 ± 4.2 | 10/10 |
| KLH | 25.9 ± 2.5 | 9.0 ± 1.4 | 10/10 |
| KLH/TNF | 45 ± 2.3**/## | 0.9 ± 0.5**/# | 3/10 |
| KLH/TNF | 43.5 ± 3.3*/## | 1.0 ± 0.32**/# | 6/10 |

*p < 0.01 vs KLH
**p < 0.001 vs KLH
p < 0.02 vs PBS
p < 0.001 vs PBS (test t of Student)

The results show that the treatment by KLH-TNFα and by KLH-TNFα+MTX induces, in a statistically significant manner:

a delay in the occurrence of the arthritis, as compared with the control animals treated by KLH alone or by PBS.

a decrease in the severity of the arthritis; and a decrease in the number of sick animals.

3—Histological Examination and Quantitative Assessment of the Arthritis.

The results are reported in table 18 hereunder.

TABLE 18

| Treatment | Inflammation Scores ± sem | Destruction Scores ± sem |
|---|---|---|
| PBS | 1.30 ± 0.09 | 0.71 ± 0.11 |
| KLH | 1.53 ± 0.21 | 1.10 ± 0.23 |
| KLH/TNF | 0.16 ± 0,.09** | 0.08 ± 0,.03** |
| KLH/TNF | 0.24 ± 0.09** | 0.21 ± 0.12* |

*p < 0.01 vs KLH et vs PBS
**p < 0.001 vs KLH et vs PBS (Student's t test)

Treatment with KLH-TNF and with KLH-TNF+MTX induces, in a statistically significant manner, a decrease in the histological alterations (destruction and joint inflammation parameter).

C—Conclusion

Vaccination of the huTNFa transgenic mice with KLH-TNFα (human) kinoid preparation according to example 1 clearly protects the animals from inflammation and joint destruction, as it is shown by the results of the clinical and histological analysis.

The groups of animals treated with KLH-TNFα (human) kinoid preparation, as regards the joint protection, cannot be distinguished from the groups of animals treated with KLH-TNFα (human) kinoid preparation combined with MTX; These results may be explained by the fact that the major efficiency of the KLH-TNFα (human) kinoid alone masks, in these experimental conditions, the eventual beneficial effect of MTX.

The groups of animals treated by KLH cannot be distinguished from the groups of animals treated by PBS buffer.

References

Adler H L, McCurdy M A, Kattan M W, Timme T L, Scardino P T, Thompson T C. Elevated levels of circulating interleukin-6 and transforming growth factor-beta 1 in patients with metastatic prostate carcinoma. J Urol 1999; 161:182-7

Aucouturier J et al., Adjuvants designed for veterinary and human vaccines. Vaccine 2001 19:2666-72

Baras B. et al., Single-dose mucosal immunization with biodegradable microparticles containing a *Schistosoma mansoni* antigen. Infect Immun. (1999) 67:2643-8) Basak A, Boudreault A, Chen A, Chretien M, Seidah N G, Lazure C, Application of the multiple antigenic peptides (MAP) strategy to the production of prohormone convertases antibodies: synthesis, characterization and use of 8-branched immunogenic peptides: J Pept Sci 1995 November-December; 1(6):385-95

Cowan et al, Induction of TNF alpha in human neuronal cells by extracellular human T-cell lymphotropic virus Type 1 Taxi, Journal of virology, 1997, 6982-6989

Ferreira F K et al, 1993, Purification and characterization of recombinant Bet v1, the major Birch pollen allergen: immunological equivalence to natural Bet v1; J. Biol. Chem., 268: 19574.

Fouts T R, Tuskan R, Godfrey K, Reitz M, Hone D, Lewis G K, DeVico A L. Expression and characterization of a single-chain polypeptide analogue of the human immunodeficiency virus type 1 gp120-CD4 receptor complex. J. Virol. 2000 December, 74(24): 11427-36.

Fouts T. Godfrey K, Bobb K, Montefiori D, Hanson C V, Kalyanaraman V S, DeVico A, Pal R. Cross-linked HIV-1 envelop-CD4 receptor complexes elicit broadly cross-reactive neutralizing antibodies in rhesus macaques. Proc. Natl. Acad. Sci. USA 2002, Sep. 3; 99(18): 11842-7. Epun 21 Aug. 2002

Le Buanec et al., HPV-16 E7 but not E6 oncogenic protein triggers both cellular immunosuppression and angiogenic processes. Biomed Pharmacother. 1999; 53: 424-31

Morgenstern J P et al., Amino acid sequence of Feld1, the major allergen of the domestic cat: protein sequence analysis and cDNA cloning, PNAS, 1991, 88:9690

Mori N et al., Interleukine-10 gene expression in adult t-cell leukemia, Blood, 1996, 1035-45

Sementchenko V I, Schweinfest C W, Papas T S, Watson D K., ETS2 function is required to maintain the transformed state of human prostate cancer cells. Oncogene 1998; 17:2883-8.

Tovey E R et al, Mite faeces are a major source of house dust allergens. Nature, 1981, 289:592-593.

Yoshiji H et al., Expression of vascular endothelial growth factor, its receptor, and other angiogenic factors in human breast cancer. Cancer Res 1996, 56:2013-6

Zagury D et al, Interferon alpha and Tat involvement in the immunosuppression of uninfected T cells and C-C chemokine decline in AIDS. Proc Natl Acad Sci USA 1998; 95: 3851-6.

Zusman I, Sandler B, Gurevich P, Zusman R, Smirnoff P, Tendler Y, Bass D, Shani A, Idelevich E, Pfefferman R, Davidovich B, Huszar M, Glick J. Comparative study of the role of serum levels of p53 antigen and its tumor cell concentration in colon cancer detection. Hum Antibodies Hybridomas. (1996)

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. A method for preparing a stable immunogenic product comprising antigenic heterocomplexes of TNFα and a Keyhole Limpet Haemocyanin(KLH) carrier protein, comprising the steps of:
   a) providing a liquid solution containing TNFα;
   b1) adding one or more antioxidant compounds to said liquid solution containing TNFα of step a); said antioxidant compound being selected from the group consisting of EDTA, acetyl cysteine, ascorbic acid, ascorbyl glucoside, calcium ascorbate, sodium ascorbate, disodium ascorbyl sulfate, magnesium ascorbate, magnesium ascorbyl phosphate, caffeic acid, and cysteine;
   b2) adding, to the liquid solution obtained at the end of step b1), one or more compounds that induce exposition to the solvent of the hydrophobic portions of TNFα;
   c) adding a carrier protein to the liquid solution obtained at the end of step b), so as to obtain a liquid measure of TNFα and said carrier protein; said carrier protein consisting of KLH;
   d) adding glutaraldehyde to the liquid mixture obtained at the end of step c), so as to partially covalently conjugate TNFα molecules to said carrier protein and obtain heterocomplexes between TNFα and said carrier protein;
   e) removing glutaraldehyde and free molecules of both TNFα and said carrier protein from the solution obtained at the end of step d), so as to obtain a liquid solution containing purified heterocomplexes between TNFα and said carrier protein;
   f) adding formaldehyde to the liquid solution obtained at the end of step e), and maintaining the presence of formaldehyde for a period of time ranging from 48 hours to 240 hours;
   g) adding glycine to the heterocomplexes between TNFα and said carrier protein obtained at the end of step f); and
   h) removing formaldehyde and glycine from the liquid solution obtained at the end of step g), so as to obtain a liquid solution containing stabilized heterocomplexes between TNFα and said carrier protein.

2. The method of claim 1, wherein step b2) comprises adding to the liquid solution obtained at the end of step b1) a compound that induces exposition to the solvent of the hydrophobic portions of TNFα and wherein said compound consists of DMSO.

3. The method of claim 1, wherein step d) comprises the following steps:
   d1) adding glutaraldehyde to the liquid mixture obtained at the end of step c), so as to partially covalently conjugate TNFα molecules to said carrier protein and obtain heterocomplexes between TNFα and said carrier protein; and
   d2) adding one or more antioxidant compounds to the heterocomplexes between TNFα and said carrier obtained at the end of step d1), said antioxidant compound being selected from the group consisting of EDTA, acetyl cysteine, ascorbic acid, ascorbyl glucoside, calcium ascorbate, sodium ascorbate, disodium ascorbyl sulfate, magnesium ascorbate, magnesium ascorbyl phosphate, caffeic acid, and cysteine.

4. The method of claim 1, wherein at step a) TNFα concentration ranges from 0.1 mg/mL to 50 mg/mL.

5. The method of claim 1, wherein at step a) TNFα concentration ranges from 0.5 mg/mL to 10 mg/mL.

6. The method of claim 1, wherein at step b), the antioxidant consists of EDTA.

7. The method of claim 6, wherein the final EDTA concentration ranges from 1 mM to 10 mM.

8. The method of claim 2, wherein at step b2) the final DMSO concentration ranges from 5% v/v to 20% v/v.

9. The method of claim 1, wherein at step c) the molar ratio of TNFα to said carrier protein ranges from 5: 1 to 100:1.

10. The method of claim 1, wherein at step d), the final glutaraldehyde concentration ranges from 0.05% w/w to 0.5% w/w.

11. The method of claim 3, wherein at step d2), when the antioxidant consists of EDTA, then the final EDTA concentration ranges from 1 mM to 10 mM.

12. The method of claim 1, wherein at step e) glutaraldehyde is removed by performing a dialysis or by performing an ultrafiltration with diafiltration.

13. The method of claim 1, wherein at step f), the final concentration of formaldehyde ranges from 1% w/w to 10% w/w.

14. The method of claim 1, wherein at step f), the final concentration of formaldehyde ranges from 2% w/w to 5% w/w.

15. The method of claim 1, wherein at step f) the presence of formaldehyde is maintained during a period of time ranging from 96 hours to 192 hours.

16. The method of claim 1, wherein at step f) the presence of formaldehyde is maintained during a period of time ranging from 120 hours to 168 hours.

17. The method of claim 1, wherein at step g) the final glycine concentration ranges from 0.01 M to 10 M.

18. The method of claim 1, wherein at step g) the final glycine concentration ranges from 0.05 M to 2 M.

19. The method of claim 1, wherein at step h) formaldehyde and glycine are removed by performing a dialysis, but performing an ultrafiltration with diafiltration, or by performing Tangential Flow Filtration (TFF).

20. A method of preparing a vaccine composition comprising the steps of:
- a) preparing a stable immunogenic product comprising antigenic heterocomplexes of TNFα by performing the method of claim 1; and
- b) combining said stable immunogenic product comprising antigenic heterocomplexes of TNFα prepared at step a) with one or more oil em